United States Patent [19]

Fukuda

[11] Patent Number: 5,880,267
[45] Date of Patent: Mar. 9, 1999

[54] TROPHININ AND TROPHININ-ASSISTING PROTEIN AGONISTS, ANTIBODIES AND ANTAGONISTS

[75] Inventor: Michiko N. Fukuda, San Diego, Calif.

[73] Assignee: La Jolla Cancer Research Foundation, La Jolla, Calif.

[21] Appl. No.: 738,975

[22] Filed: Oct. 24, 1996

Related U.S. Application Data

[63] Continuation of Ser. No. 439,818, May 12, 1995, Pat. No. 5,654,145, which is a continuation-in-part of Ser. No. 317, 522, Oct. 4, 1994, Pat. No. 5,599,918.

[51] Int. Cl.$^6$ .......................... C07K 15/28; C07K 16/00; A61K 39/395; A61K 39/40
[52] U.S. Cl. .................... 530/387.1; 530/388.1; 530/388.2; 530/389.1; 424/143.1; 424/152.1; 436/501; 514/2; 514/8; 514/12; 514/13
[58] Field of Search .............................. 530/387.1, 388.1, 530/388.2, 389.1, 350; 424/143.1, 152.1; 514/2, 8, 12, 13, 14, 15, 16, 17; 436/501

[56] References Cited

U.S. PATENT DOCUMENTS

| | | | |
|---|---|---|---|
| 3,678,076 | 7/1972 | Crenshaw . | |
| 4,732,763 | 3/1988 | Beck et al. . | |
| 5,227,292 | 7/1993 | White et al. ........................... | 435/69.1 |
| 5,240,922 | 8/1993 | O'Neil . | |
| 5,242,826 | 9/1993 | Tsilibary et al. . | |
| 5,279,941 | 1/1994 | Lessey . | |
| 5,279,966 | 1/1994 | Jessell et al. ........................ | 435/320.1 |
| 5,344,919 | 9/1994 | Quaranta et al. ....................... | 530/395 |
| 5,395,825 | 3/1995 | Feinberg et al. .......................... | 514/21 |
| 5,478,725 | 12/1995 | Lessey et al. . | |
| 5,521,067 | 5/1996 | Seshi ...................... | 435/7.24 |
| 5,578,306 | 11/1996 | Lessey ................. | 424/143.1 |
| 5,654,145 | 8/1997 | Fukuda et al. .............. | 435/6 |

OTHER PUBLICATIONS

Aplin, J., "Adhesion molecules in implantation", Reviews Reproduction 2(2):84–93, 1997.
Sigma Catalog, pp. 990–991, 1993.
Kebabian et al, "Compounds selective for dopamine receptor subtypes", Drug Discovery 2(8):333–340, 1997.
Denker, H.W.,"Implantation: A cell biological paradox." J. of Experimental Zoology, 266:541–558 (1993).
Flamigni et al., "Factors regulating interaction between trophoblast and human endometrium." Annals New York Academy of Sciences 622:177–187 (1991).
Carson et al., "Glycoconjugate synthesis during early pregnancy: Hyaluronate synthesis and function." Dev. Biol. 120:228–235 (1987).
Armant et al., "Fibronectin and laminin promote in vitro attachment and outgrowth of mouse blastocysts." Dev. Biol. 116:519–523 (1986).
Anderson et al., "Membrane composition of the endometrial epithelium: molecular marker of uterine receptivity to implantation." In: Human Reproduction (Int's Congress Ser., No. 768. R. Iizuka nd K. Semm. eds. Excerpta Medica Amsterdam 513–516 (1988).

Carson et al., "Uterine stromal cell chondroitin sulfate proteoglycans bind to collagen type I and inhibit embryo outgrowth in vitro." Dev. Biol. 149:307–316 (1992).
Carson et al., Glycoconjugate expression and interactions at the cell surface of mouse uterine epithelial cells and peri–implantation–stage embryos. In: Trophoblast Invasion and Endometrial Receptivity. Novel Aspects of the Cell Biology of Embryo Implantation. (Trophoblast Research. vol. 4.) H.W. Denker and J.D. Aplin eds. Plenum Medical Book Comp. New York, 211–241 (1990).
Hoffman et al., "Uterine receptivitiy to implantation to the Rabbit: Evidence for a 42kDa glycoprotein as a marker of receptivity." In: Trophoblast Invasion and Endometrial Receptivity. Novel Aspects of the Cell Biology of Embryo Implantation. (Trophoblast Research, vol. 4.) H.W. Denker and J.D. Aplin, eds. Plenum Medical Book Comp., New York, 243–258 (1990).
Lampelo et al., "Purification of rabbit endometrial plasma membranes from receptive and non–receptive uteri." J. Reprod. Fertil. 75:475–484 (1985).
Schlafke and Enders, "Cellular basis of interaction between trophoblast and uterus at implantation." Biol. of Reproduction 12:41–65 (1975).
Aplin, John D., "Implantation, trophoblast differentiation and haemochorial placentation: mechanistic evidence in vivo and in vitro." J. of Cell Science 99:681–692 (1991).
Pullman and Bodmer, "Cloning and characterization of a gene that regulates cell adhesion." Nature 356:529–532 (1992).
Harlow and Lane, "Antibodies, a laboratory manual." Cold Spring Harbor Laboratory pp. 53–77 and 139–155 (1988).
Maniatis et al., "Molecular cloning, a laboratory manual." Cold Spring Harbor Laboratory pp. 404–433 (1982).

(List continued on next page.)

Primary Examiner—Jeffrey Fredman
Attorney, Agent, or Firm—Campbell & Flores LLP

[57] ABSTRACT

The present invention provides substantially purified mammalian trophinin which can mediate cell adhesion. The invention also provides substantially purified trophinin-assisting proteins, which interact with trophinin to mediate cell adhesion. The invention further provides antibodies that are specifically reactive with trophinin or a trophinin-assisting protein. In addition, the invention provides active fragments of trophinin or trophinin-assisting proteins. The invention further provides a nucleic acid molecule encoding trophinin or a trophinin-assisting protein, vectors containing the nucleic acid molecules and host cells containing the vectors. The invention also provides a nucleotide sequence that can hybridize to a nucleic acid molecule encoding trophinin or a trophinin-assisting protein. The invention further provides methods to detect trophinin or a trophinin-assisting protein or a nucleic acid molecule encoding trophinin or a trophinin-assisting protein in a sample. The invention also provides methods of effecting cell adhesion by modifying cells to express trophinin or a trophinin-assisting protein. The invention further provides trophinin antagonists and methods to reduce or inhibit cell adhesion. The invention also provides methods to treat cells with trophinin agonists resulting in increased cell adhesion.

14 Claims, 15 Drawing Sheets

OTHER PUBLICATIONS

Carson et al., "Cell surface glycoconjugates as modulators of embryo attachment to uterine epithelial cells." *Int. J. Biochem.*, 26:1269–1277 (1994).

Svalander et al., Expression of cellCAM–105 in the apical surface of rat uterine epithelium is controlled by ovarian steriod hormones. *J. Reprod. Fert.*, 88:213–221 (1990).

Lindenberg, "Experimental studies on the initial trophoblast endometrial interaction." *Danish medical Bulletin*, 38(5): 371–380 (1991).

Diamandis, "Analytical methodology for immunoassays and DNA hybridization assays—current status and selected systems—critical review." *Clinica Chimica ACTA*, 194:19–50 (1990).

Matthews and Kricka, "Analytical stragegies for the use of DNA probes." *Analytical Biochem.*, 169:1–25 (1988).

Lichter et al., "Clustering of C2–H2 zinc finger motif sequences within telomeric and fragile site regions of human chromosomes." *Genomics* 13:999–1007 (1992).

Peterson et al., "Functional domains and upstream activation properties of cloned human TATA binding protein." *Science*, 248:1625–1630 (1990).

Vanderslice et al., "Human mast cell tryptase: Multiple cDNAs and genes reveal a multigene serine protease family." *Proc. Natl. Acad. Sci.*, 87:3811–3815 (1990).

Corness et al., "A human somatostatin receptor (SSTR3), located on chromosome 22, displays preferential affinity of somatostatin–14 like peptides." *Febs Letters*, 321:279–284 (1993).

Levesque et al., "DNA transfection in cos cells: A low cost serum–free method compared to lipofection." *Biotechniques*, 11(3):313–315, 317, 318 (1991).

Miki et al., "Simple colorimetric cell–cell adhesion assay using MTT stained leukemia cells." *J. Immunological Methods*, 164:255–261 (1993).

Shapiro et al., "Cloning and characterization of a unique elastolytic metalloproteinase produced by human alveolar macrophages." *J. Biol. Chem.*, 268:23824–23829 (1993).

Mulligan, "The basic science of gene therapy." *Science*, 260:926–930 (1993).

Morgan and Anderson, "Human gene therapy." *Ann. Rev. Biochem.*, 62:191–217 (1993).

Brown et al., "Gene therapy oversold by researchers, journalists." *The Washington Post*, ppA1 and A22 (Dec. 8, 1995).

Marshall, "Gene therapy's growing pains." *Science* 269:1050–1055 (1995).

Sato et al., "Trophoblast cell adhesion molecule: Trophonectin." Genbank accession #U04811, ID #HSP48110. (Submitted Dec. 30, 1993); available to public on Jun. 1, 1995.

Fukuda et al., "Trophinin and tastin, a novel cell adhesion molecular complex with potential involvement in embryo implantation." *Genes & Dev.*, 9:1199–1210. (1995).

Tabibzadeh and Babaknia, "The signals and molecular pathways involved in implantation, a symbiotic interaction between blastocyst and endometrium involving adhesion and tissue invasion." *Human Reprod.*, 10(6): 1579–1602 (1995).

Aplin et al., "The endometrial cell surface and implantation: expression of the polymorphic mucin MUC–1 and adhesion molecules during the endometrial cycle." *Ann. New York Acad. Sci.* 734:103–121 (1994).

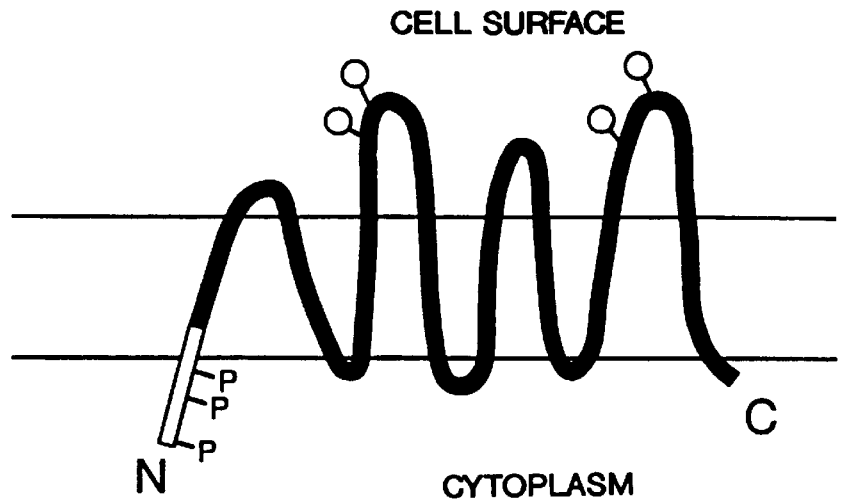

FIG. 5A

| 69 | |
|---|---|
| FSGGPGIT | FSGAPITNPG |
| FGVAPSTSAS | FGGAFSTSAG |
| FSNTASIS | FGGALSTAAD |
| FGGTLSTSSS | FGGTPSNSIG |
| FSSAASIS | FGAAPSTSVS |
| FGCAHSTSTS | FGGAHGTSLC |
| FSSEASIS | FGGAPSTSLC |
| FGGMPCTSAS | FGSASNTNLC |
| FSGGVSSS | FGGPPSTSAC |
| FSGPLSTSAT | FSGATSPS |
| FSGGASSG | FCDGPSTSTG |
| FGGTLSTTAG | FSFGNGLSTG |
| FSGVLSTSTS | FGGGLNTSAG |
| FGSAPTTSTV | FGGGLGTSAG |
| FSSALSTSTG | FSGGLSTSSG |
| FGGILSTSVC | FDGGLGTSAG |
| FGGSPSSSGS | FGGGPGTSTG |
| FGGTLSTSIC | FGGGLGTSAG |
| FGGSPCTSTG | FSGGLGTSAG |
| FGGTLSTSVS | FGGGLVTSDG |
| FGGSSSTSAN | FGGGLGTNAS |
| FGGTLSTSIC | FGSTLGTSAG |
| FDGSPSTGAG | FSGGLSTSDG |
| FGGALNTSAS | FGSRPNAS |
| FGSVLNTSTG | FDRGLSTIIG |
| FGGAMSTSAD | FGSGSNTSTG |
| FGGTLSTSVC | FTGEPSTSTG |
| FGGSPGTSVS | FSSGPSSIVG |
| FGSALNTNAG | FSGGPSTGG |
| YGGAVSTNTD | FCSGPSTSG |
| FGGTLSTSVC | FSGGPSTGAG |
| FGGSPSTSAG | FGGGPNTGAG |
| FGGALNTNAS | FGGGPSTSAG |
| FGCAVSTSAS | FGSGAASLGACG |
| FSGAVSTSAC | 745 |

```
1171  GTTGCCGTCCGGTGTTGTTGACCAGGAGAGTTGTATAAGGTCACTGGAGGGTTCTGGGAAACCACCGGTGGCCACTCCTTCTGGACCCCAC  1260
391    V  A  V  R  L  F  D  Q  E  S  C  I  R  S  L  E  G  S  G  K  P  P  V  A  T  P  S  G  P  H   420

1261  TCTAACAGAACCCCCAGCCTCCAGGAGGTGAAGATTCAACGCTATCCTGCAACAGCTGTTGAGACAGGAAGTAGAGGGGCTGGTA  1350
421    S  N  R  T  P  S  L  Q  E  V  K  I  Q  R  I  G  I  L  Q  Q  L  L  R  Q  E  V  E  G  L  V   450

1351  GGGGCCAGTGTGTCCCCTTAATGGAGGCTCTCTCTGGATATGTTGAACTTCAGCCCCTGCTGACTGAGATTTCTAGAACTCTGAAT  1440
451    G  G  Q  C  V  P  L  N  G  G  S  S  L  D  M  V  E  L  Q  P  L  L  T  E  I  S  R  T  L  N   480

1441  GCCACAGAGCATAACTCTGGGACTTCCCACCTTCCTGGACTGTTAAAACACTCAGGGCTGCCAAAGCCCTGCTTCCAGAGGAGTGCGGG  1530
481    A  T  E  H  N  S  G  T  S  H  L  P  G  L  L  K  H  S  G  L  P  K  P  C  L  P  E  E  C  G   510

1531  GAACCACAGCCCTGCCTCCGGCAGAGCCTGGGGCCCCAGGAGCCTGAGATACCAGAGCCCTCCCTCCAGGAA  1620
511    E  P  Q  P  C  P  P  A  E  P  P  G  P  P  E  A  F  C  R  S  E  P  E  I  P  E  P  S  L  Q  E   540

1621  CAGCTTGAAGTACCAGAGCCCTACCCTCCAGCAGAACCCAGGCCCCTCGAGAGTCCTACTGTAGGAGTGAGCCTGAGATTGAGCCTGAGATACCG  1710
541    Q  L  E  V  P  E  P  Y  P  P  A  E  P  R  P  L  E  S  C  C  R  S  E  P  E  I  P  E  S  S   570

1711  CGCCAGGAACAGCTTGAGGTACCTGAGCCTTGCCCTCCAGCAGAACCCGGCCCCTCAGCCCTGAGCCTACCCTGAGGAACCGAGTCT  1800
571    R  Q  E  Q  L  E  V  P  E  P  C  P  P  A  E  P  R  P  L  E  S  Y  C  R  I  E  P  E  I  P   600

1801  GAGTCCTCTCGCCAGGAACAGCTTGAGGTACCAGGTAGAGCTTGCCCTCCAGCCCCTGCACCCGAGAACATAGAAGTCTAGAGTCCAGTCTACCACCC  1890
601    E  S  S  R  Q  E  Q  L  E  V  P  E  P  C  P  P  A  E  P  G  P  L  Q  P  S  T  Q  G  Q  S   630

1891  GGACCCCCAGGGCCCTGCCCAGGTAGAGCTTGGGGCGCATCAGAGCCCTGAACATAGAAGTCTAGAGTCCAGTCCAGTCTACCACCC  1980
631    G  P  P  G  P  C  P  P  R  V  E  L  G  A  S  E  P  C  T  L  E  H  R  S  L  E  S  S  L  P  P   660

1981  TGCTGCAGTCAGTGGGCTCCAGCAACCTGATCTCTCTCTCAACACCCGCTTGTGCCAGCCCGCTTGTGCCAGCCCGGAGGAGGAGCCTCAAATCTGTTTAACC  2070
661    C  C  S  Q  W  A  P  A  T  T  S  L  I  F  S  S  Q  H  P  L  C  A  S  P  P  I  C  S  L  Q   690

2071  TCTTTGAGACCCCAGCCTGCTTCCACGAGGCTCGTCGGACGATGAGTGCCTTTTACACCAGGCCTGCCTTCAGCCCGAGCCTCCCCTCCTGAAACCCG  2160
691    S  L  R  P  P  A  G  Q  A  G  L  S  N  L  A  P  R  T  L  A  L  R  E  S  L  K  S  C  L  T   720

2161  GCCATCCACTGCTTCCACGAGGCTCGTCGGACGATGATGAGTGCCTTTTACACCAGGCCTGCCTTCAGCCCGAGCCTCCCCTCCTGC  2250
721    A  I  H  C  F  H  E  A  R  L  D  D  E  C  A  F  Y  T  S  R  A  S  P  S  G  P  T  R  V  C   750

2251  ACCAACCCTGTGGCTACATTACTCGAATGGCAGGATGCCCTGTGTTCATTCAGTTGTTCGGTCTGCCCATGGGACTCTCCATGATGA  2340
751    T  N  P  V  A  T  L  L  E  W  Q  D  A  L  C  F  I  P  V  G  S  A  A  P  Q  G  S  P  END   780

2341  GACAACCACTCCTGCCCTTTAGCCCTTATTATTGTCGGTCTGCCCATGGGAGCCGCCCACTTTTGTC  2430
2431  CTCAATAAAGTTTCTAAAGTAAAAAAAAAAAAAAAAAAAA
```

FIG. 6B

```
                    AATTCGGCTGCCATAGAGATGTTCATGAACAAGAACCCTCCTGCCAGGCGCACCCTGGCTGACATCATC                     -1
  1 ATGGAGAAGCTGACTGAGAAGCAGACAGAGGTTGAGACAGTCATGTCAGAGGTGTCGGGCTTCCCTATGCCCCAGCTGGACCCCCGGGTC           90
  1  M  E  K  L  T  E  K  Q  T  E  V  E  T  V  M  S  E  V  S  G  F  P  M  P  Q  L  D  P  R  V           30

91 CTAGAAGTGTACAGGGGGGTCCGGGAGGTTATTATCTAAGTACCGCAGTGGAAACTGCCCAAGGCATTTAAGATCATCCCTGCACTCTCC          180
 31  L  E  V  Y  R  G  V  R  E  V  L  S  K  Y  R  S  G  K  L  P  K  A  F  K  I  I  P  A  L  S           60

181 AACTGGGAGCAAATCCTCTACTGTCACAGAGCCTGGAGCTGCCATGTACCAGGCCACCAGGATTTTGCCTCTAACCTG                      270
 61  N  W  E  Q  I  L  Y  V  T  E  P  E  A  W  T  A  A  A  M  Y  Q  A  T  R  I  F  A  S  N  L           90

271 AAGGAACGCATGGCCCAGCGCTTCTACAACTTGTCCTCGTCCTCCTCGAGTACGACGTTGGTGAATACAAACGACTCAACTTCCAT               360
 91  K  E  R  M  A  Q  R  F  Y  N  L  V  L  L  P  R  V  R  D  D  V  G  E  Y  K  R  L  N  F  H          120

361 CTCTACATGGCTCTCAAGAAGGCCCTTTTCAAACCTGGAGCCTGGTTCAAAGGAATCCTGATTCCACTGTGCGAGTCTGGCACTTGTACC          450
121  L  Y  M  A  L  K  K  A  L  F  K  P  G  A  W  F  K  G  I  L  I  P  L  C  E  S  G  T  C  T          150

451 CTCCGGGAAGCCATCATTGTGGTAGCATCATCACCAAGTGCTCCATCCCTGTGTTGCACTCCAGTGCGCCATGCTGAAAATTGCTGAG            540
151  L  R  E  A  I  I  V  G  S  I  I  T  K  C  S  I  P  V  L  H  S  S  A  A  M  L  K  I  A  E          180

541 ATGGAATACAGCGGTGCCAACAGCATCTTCCTGCGACTGCTGGATAAGAAGTATGCACTGCCTTACCGGGTGCTGGATGCCCTAGTC             630
181  M  E  Y  S  G  A  N  S  I  F  L  R  L  L  D  K  K  Y  A  L  P  Y  R  V  L  D  A  L  V            210

631 TTCCACTTCCTGGGGTTCCGGACAGAGAAGAGGCCCTCTTAGAACTGCTCCAGCCCATCCACAGCTATCCCGAAATCAGGCGTGAGCTT           720
211  F  H  F  L  G  F  R  T  E  K  R  E  L  P  V  L  W  H  Q  C  L  T  L  V  Q  R  Y  K  A            240

721 GACTTGGCCACAGACCAGAAGGAAGCCCTGCTGGAGCTGCTTCGACACCGTGAGTGAAAACAGTCAGCTTGTCCTGGCCAAAGGGGTTTGGAAGG     810
241  D  L  A  T  D  Q  K  E  A  L  L  E  L  L  R  L  Q  P  H  P  Q  L  S  P  E  I  R  R  E  L          270

811 CAGAGTGCAGCCCCCGTGGAAGATGTTCCCATCACCGTGAGTGAGAAAACAGTCAGCTTGTCCTGGCCAAAGGGGTTTGGAAGG                 900
271  Q  S  A  A  P  A  C  G  R  C  S  H  H  R  G  V  R  K  T  V  S  L  S  W  P  K  G  F  G  R          300

901 ACACCAAGACCCCGTTGGTGACTGAAGATGACACTGAGCTTTAATGCTGAAGACCCAGATCAGGGCAGTGACCAGATCACAGGACATC            990
301  T  P  R  P  R  W  END

991 TGTGGCTCCCAGTCCAGGACAGGAAGGACTGAGGGTCTGGCTGTTCCCTCTTCCATTCTAGGCCCTTATCCCTGTTTAGTTCTGAGAGC         1080
1081 CAACTTGAGATACCATATGCTAGCATTCCCAGTGCCCCAGCTTGGTGTGAGTACTTTTCTATGCTATTGTGTCAGGTCACTGT               1170
1171 GGATAAAGGCAAAGACAGATATTTATTGAAAAAAAAAAAAAAAAAAAAAA
```

FIG. 7

```
                                                                                      -181
                              CACCTCTGTCGTTCCCA                                        -91
                                                                                        -1

-180 GTGTTCCACAAGAAGAAACCTTACGTCAGGCCCCTGCTGGACTCCCCGAGAAACTCTGTTCCAATCCGGTTCTTCCTCCCAAAGAA   -91
 -90 TTCCTTCTTGTCTCCCACCATTCCCCGTCCCCTCAAGCTCCCTGCCCCCAAACTTCCAGTGCTGCTCCTCCCAAGACAAGAGACTTCTGGCTGGATGCCAC   -1

1 ATGTGCTCCAGAAGGGACCCTCACTCCTGTGTTCTGCCGTTCTCTCCAGGCCCCTGGCCTTCCCAGAGGCCCCCTGGCTTCCCAGGAAGGA   90
   1  M  C  S  R  R  D  P  H  S  C  V  L  P  L  L  S  K  R  L  L  S  R  A  P  W  L  P  R  R  K  G   30

91 CCCAGTATCCACCCCCAGCTGGTGGTGAACAAGAAGCCTCCCTTCTCTCCCACCACCAGAAGCCCCGCTCACTCCCTG  180
  31  P  S  I  H  P  Q  L  V  V  N  K  K  P  P  F  S  P  T  T  R  K  P  P  L  T  P  L   60

181 AAGCTCCTGAGAAAGACCCCTGACCCTCCCCAACAGTTCCCAGAGCTGCTCCAGAGCCCGTTCCAAAAGGAC  270
  61  K  L  L  R  K  T  P  D  D  P  S  P  T  V  P  E  T  D  M  D  P  L  L  Q  S  P  V  S  Q  K  D   90

271 ACCCCTTTCCAGATCTCTTCTGGAGTCCAGAAGGAACAGCCGCTCCCCACGGGAGAGATCACCCGTTGGTGTGTGGGCTGCCGTCCAA  360
  91  T  P  F  Q  I  S  S  G  V  Q  K  E  Q  P  L  P  T  G  E  I  T  R  L  G  V  W  A  A  V  Q   120

361 GCAGTGGAGAGGAAGCTGGAGGCCCAGGCCCATGAGCGCAAGATAGCCGACTGC  450
 121  A  V  E  R  K  L  E  A  Q  A  M  R  L  L  T  L  E  G  R  T  G  T  N  E  K  K  I  A  D  C   150

451 GAGAAGACAGCCGTGGAGTTCGCGAACCATCTGGAGAGCAAGTGGGTCGTGTTGGGACCCTGCTGCAGGAGTATGGGCTGCAGAGG  540
 151  E  K  T  A  V  E  F  A  N  H  L  E  S  K  W  V  V  L  G  T  L  L  Q  E  Y  G  L  Q  Q  R   180

541 CGGCTGGAGAACATGGAGAACCTGCTGAAAAACAGAAATTTCTGGATCCTGCGGCCAGCAATGGAGAAGTTCCAAGGTC  630
 181  R  L  E  N  M  E  N  L  L  K  N  R  N  F  W  I  L  R  L  P  P  G  S  N  G  E  V  P  K  V   210

631 CCTGTCACATTTGATGATGTGCTGTGCACTTCTCGGAGCAGGAGTGGGAAACCTGTCTGAGTGGCAGAAGGAGCTCTACAAGAACGTG  720
 211  P  V  T  F  D  D  V  A  V  H  F  S  E  Q  E  W  G  N  L  S  E  W  Q  K  E  L  Y  K  N  V   240

721 ATGAGGGGCAACTACGAGTCCCTGGTTTCCATGGACTATGCAATTTCAAACCAGACCTCATGTCACAGATGAGCGCGGGAGCGGCCC  810
 241  M  R  G  N  Y  E  S  L  V  S  M  D  Y  A  I  S  K  P  D  L  M  S  Q  M  E  R  G  E  R  P   270
```

FIG. 8A

```
811  ACCATGCAGGAGCAGGAAGACTCTGAGGAGGAGGGCGAAACGCCCGACAGATCCCAGTGCTGCCGACGATGGATCGTGATTAAGATCGAGGTA   900
271   T  M  Q  E  Q  E  D  S  E  E  E  G  E  T  P  T  D  P  S  A  A  H  D  G  I  V  I  K  I  E  V   300

901  CAGACCAACGACGAGGGCTCAGAAAGTTTGGAGACACCTGAGCCCCTGATGGGACAGGTGGAAGAGCACGGCTTCCAGGACTCAGAGCTG    990
301   Q  T  N  D  E  G  S  E  S  L  E  T  P  E  P  L  M  G  Q  V  E  E  H  G  F  Q  D  S  E  L    330

991  GGTGACCCCTGTGGGGAACAGCCAGACCTGGACATGCAGGAGCCAGAGAACACGCTGGAGGAGTCCACGGAGGCTCCAGCGAGTTCAGC   1080
331   G  X  P  C  G  E  Q  P  D  L  D  M  Q  E  P  E  N  T  L  E  E  S  T  E  G  S  S  E  F  S    360

1081 GAACTGAAGCAGATGCTGGTGCAGCAGAGAAACTGCACGGAGGGGATCGTGATCAAGACAGAGGAACAAGAGGAACAAGAGGAAGAAGAGGAG   1170
361   E  L  K  Q  M  L  V  Q  Q  R  N  C  T  E  G  I  V  I  K  T  E  E  Q  D  E  E  E  E  E  E    390

1171 GAGGAGGATGAGCTGCCCCAGCACTTGCAATCCCTTGGGCAGCTGTCCGGAGATATGAGGCCAGTATGTACCAGACCCCGCTGCCCGGG    1260
391   E  E  D  E  L  P  Q  H  L  Q  S  L  G  Q  L  S  G  R  Y  E  A  S  M  Y  Q  T  P  L  P  G    420

1261 GAGATGTCCCCCGAGGGCGAGGAGGAGAGCCCCCCACCTCCAGTTGGAAACCCCGCAGTGAAAAGGCTGGCCCCTTCCGTGCACGGTGAG   1350
421   E  M  S  P  E  G  E  E  E  S  P  P  P  L  Q  V  G  N  P  A  V  K  R  L  A  P  S  V  H  G  E   450

1351 CGGGACCTGAGCGAGAACCGCGGGGGCTCGAGCCAGCAGAGTCGGGAACCGGCGGCCCTTCACATGGAGTGCGGCAAG    1440
451   R  D  L  S  E  N  R  G  G  S  S  Q  Q  S  G  N  R  R  G  E  R  P  F  T  C  M  E  C  G  K    480

1441 AGCTTCCGCCTGAAGATCAACCTCATCATCCACCAGCGCAACCAACATCAAGGAGGGGCCCTACGAGTGCGCGAATGTGAGATCA    1530
481   S  F  R  L  K  I  N  L  I  I  H  H  Q  R  N  Q  H  Q  G  G  P  T  S  A  P  N  V  R  S    510

1531 GCTTTCCGGCACAAGCAACAGCTGACGCACCAGCGCATCCACCGCGTGCGCGGAGGCTGCGTGTCCCACCGGAGCGGCCCACGTTC    1620
511   A  F  R  H  K  Q  Q  L  T  L  H  Q  R  I  H  R  V  R  G  G  C  V  S  P  E  R  G  P  T  F    540

1621 AACCCCAAGAACGCGCTCAAGCCGCGTCCCAAGTCACCCAGTCTCCAAGTCCTGTGCCCCTAAGCCCTACAAGTGCCCGAGTGC    1710
541   N  P  K  X  A  L  K  P  R  P  K  S  P  S  S  G  G  G  P  K  P  Y  K  C  P  E  C    570

1711 GACAGCAGCTTCAGCCACAAGTCCAGCCTGACTAAACACCAGATCACGCACACGGGTGAGCGGCCCTACACGTGCCCCGAGTGCAAGAAG   1800
571   D  S  S  F  S  H  K  S  S  L  T  K  H  Q  I  T  H  T  G  E  R  P  Y  T  C  P  E  C  K  K   600
```

FIG. 8B

1801 AGCTTCCGCCTGCACATCAGCTTGGTGATCCATCAGCGGGTGCACGGGCAAGCATGAGGTCTCCTTCATCTGCAGCCTGTGCGGCAAG 1890
601  S   F   R   L   H   I   S   L   V   I   H   Q   R   V   H   G   K   H   E   V   S   F   I   C   S   L   C   G   K   630

1891 AGCTTCAGCCGCCCCTCGCACCTGCGCCACCAGGGACTCACACAGGCCCCTTCAAGTGCCCCGAGTGCGAGAAGAGCTTC 1980
631  S   F   S   R   P   S   H   L   L   R   H   Q   R   T   H   T   G   E   R   P   F   K   C   P   E   C   E   K   S   F   660

1981 AGCGAGAAGTCCAAGCTCACCAACCACTGCCGCGTGCACTCGCGC
661  S   E   K   S   K   L   T   N   H   C   R   V   H   S   R

FIG. 8C

TROPHININ AND TROPHININ-ASSISTING PROTEIN AGONISTS, ANTIBODIES AND ANTAGONISTS

This application is a continuation of application Ser. No. 08/439,818, filed May 12, 1995, U.S. Pat. No. 5,654,145, which is a Continuation-In-Part of application Ser. No. 08/317,522, filed Oct. 4, 1994, U.S. Pat. No. 5,599,918, the entire contents of which are incorporated herein by reference.

This work was supported by grant number DK37016 awarded by the National Institutes of Health. The United States government has certain rights in this invention.

BACKGROUND OF THE INVENTION

FIELD OF THE INVENTION

This invention relates generally to the fields of biochemistry and molecular biology and more specifically to cell adhesion molecules.

BACKGROUND INFORMATION

The early stages of pregnancy involve fertilization of an egg by a sperm, followed by cell division and implantation of the embryo into the uterine cell wall. The inability of the embryo to properly implant in the uterus is a significant cause of pregnancy failure following in vivo or in vitro fertilization. The early events of implantation are characterized by an initial attachment of the embryo's external cell lining (trophoblast layer) to the cells lining the uterus (endometrial epithelium) followed by or in parallel with adhesion of these two cell types. The molecular events involved in the early steps in implantation are not well understood.

Embryo attachment and adhesion to the uterine endometrium is unusual in that cells from these two sources adhere at their apical surfaces. In contrast, most other epithelial cell interactions adhere at their basal and lateral cell surfaces. The unique ability of trophoblast and endometrial cells to adhere may result from apical display of adhesion molecules normally located at basal and lateral surfaces. Alternatively, adhesion of these cell types in implantation may be mediated by unique cell surface molecules.

Recent experiments suggest that certain endometrial tumor cell lines express characteristics associated with implantation-receptive endometrial tissue. In these experiments, trophoblast cells derived from germ cell tumors adhered to monolayers of endometrial adenocarcinoma cells via their apical cell surfaces. Morphological analysis of the adhering cell surfaces showed characteristics in common with early stage implantation. However, the molecules involved in the critical early adhesion step of embryo implantation were not identified. Thus, a need exists to identify the molecules responsible for adhesion of the embryo to the uterine lining. The present invention satisfies this need and provides related advantages as well.

SUMMARY OF THE INVENTION

The present invention provides substantially purified mammalian trophinin, which mediates adhesion of cells at their apical surfaces. In addition, the invention provides a family of substantially purified mammalian trophinin-assisting proteins, including tastin, bystin and lastin, which can be involved in trophinin-mediated cell adhesion. The invention also provides antibodies that specifically bind trophinin or a trophinin-assisting protein. Such antibodies can be useful, for example, to detect trophinin or a trophinin-assisting protein in a sample. In addition, the invention provides active fragments of trophinin and trophinin-assisting proteins.

The invention also provides nucleic acid molecules encoding trophinin or a trophinin-assisting protein, vectors containing the nucleic acid molecules and host cells containing the vectors. These nucleic acid molecules can be used to express trophinin or a trophinin-assisting protein in a cell that otherwise does not express trophinin or a trophinin-assisting protein or expresses an aberrant trophinin or trophinin-assisting protein. The invention further provides methods for adhering cells together. In addition, the invention provides methods to inhibit trophinin-mediated adhesion of cells by contacting cells with a trophinin antagonist. The invention also provides a method to increase or decrease the likelihood of embryo implantation in a subject.

BRIEF DESCRIPTION OF FIGURES

FIGS. 1A and 1B show binding of embryonic trophoblastic cells HT-H (1), endometrial adenocarcinoma cells SNG-M (2) and monkey kidney cells COS-1 (3) to a monolayer of SNG-M cells (FIG. 1A) or HT-H cells (FIG. 1B). After 20 minutes (min) at room temperature (RT), nonadherent cells were removed by washing with (+) or without (−) 1 mM EDTA. The x axis indicates the percentage of cells that bound to the monolayer.

FIG. 1C shows the binding of COS-1 cells transfected with vector alone (1), vector containing tastin cDNA (2), vector containing trophinin cDNA (3) and a mixture of vectors containing tastin cDNA and trophinin cDNA (4) to a monolayer of SNG-M cells. Non adherent cells were removed by washing with 1 mM EDTA.

FIG. 1D presents the effects of anti-trophinin antibodies on cell adhesion. HT-H cells (1) or SNG-M cells (2) were added to a monolayer of SNG-M cells previously treated with pre-immune serum (−) or with anti-trophinin antiserum anti-GST-553 (+). Non adherent cells were removed by washing with 1 mM EDTA.

FIG. 2A, 10 min post co-culture revealing microvilli at the lower side of an HT-H cell (H) facing the upper surface of the SNG-M cell (S). The basal surface of the HT-H cell is indicated by short arrows. Scale bar=5 $\mu$m.

FIG. 2B is a 4.4×higher magnification of the area indicated by the parentheses in FIG. 2A. Contact of the two cell types via microvilli is evident.

FIG. 2C, 6 hr post-culture shows a HT-H cell (H) adhered to an SNG-M cell (S). Contact between the two cell types is closer than observed at 10 min culture. The microvilli are flattened in both cells and extend directly from each cell to the plasma membrane of the other cell. The SNG-M cells at this stage of contact often show invagination activity (arrow). Scale bar=1 $\mu$M.

FIG. 2D, 4 days post co-culture shows a HT-H cell (H) adhered to a SNG-M cell (S). Microvilli are absent from the surfaces of both cells and contact primarily is focal, with occasional development of an adherent junction (arrow). Scale bar=0.5 μM.

FIG. 3 presents the complete nucleotide sequence (SEQ ID NO: 1) and deduced amino acid sequence (SEQ ID NO: 2) of trophinin. Single letter amino acid symbols are used. Areas of the protein are indicated as follows: transmembrane domains (underlined), cytoplasmic domains (italics) and cell surface domains (bolded). Potential sites for N-linked and O-linked glycosylation are underlined; potential sites for protein kinase phosphorylation are indicated by shadowed letters.

FIG. 4 is an autoradiograph of an SDS-polyacrylamide gel following electrophoresis of $^{35}$S-labeled proteins obtained by in vitro translation of trophinin (lane 1) and tastin (lane 2) cDNA. Numbers on the right indicate the migration of molecular weight markers.

FIGS. 5A and 5B show a schematic representation of the trophinin molecule in the cell membrane and identify a repeating decapeptide sequence in the molecule.

FIG. 5A shows the topology of a trophinin molecule within the cell membrane. Eight potential transmembrane domains are represented and the portion of trophinin containing the tandem decapeptide repeating sequence is filled-in. The amino terminus (N), the carboxy terminus (C), potential sites for protein kinase phosphorylation (P) and potential sites for N-linked glycosylation (circles) are indicated.

FIG. 5B shows the amino acid sequence of trophinin from position 69 to 745 (SEQ ID NO: 3) in a form that identifies the individual tandem decapeptide units.

FIG. 6 presents the complete nucleotide sequence (SEQ ID NO: 4) and deduced amino acid sequence (SEQ ID NO: 5) of the tastin cDNA clone. Single letter amino acid symbols are used. Potential sites for phosphorylation by protein kinase C (underlined bold), cAMP/cGMP dependent protein kinase (underlined), casein kinase II (bold) and MAP kinase (shadowed letters) are indicated. The location of 4 tandem repeat sequences that contain the majority of cysteines in the molecule are indicated by italics between residues 516 and 650.

FIG. 7 presents the complete nucleotide sequence (SEQ ID NO: 6) and deduced amino acid sequence (SEQ ID NO: 7) of bystin. Single letter amino acid symbols are used. Threonine and serine residues within potential sites for phosphorylation by protein kinase C (underlined) and casein kinase II (bolded) are indicated. Potential sites for phosphorylation of tyrosine residues by tyrosine kinase and potential sites for myristoylation of glycine residues are indicated in bold.

FIG. 8 presents a partial nucleotide sequence (SEQ ID NO: 8) and deduced amino acid sequence (SEQ ID NO: 9) of a portion of the lastin gene. The cDNA obtained for the lastin gene was missing the 3' end of the coding sequence and the poly-A tail. Single letter amino acid symbols are used. Potential threonine and serine within sites for phosphorylation by protein kinase C (underlined) and casein kinase II (bolded) are indicated. Potential sites for myristoylation of glycine residues are indicated in bold. Amino acid residues indicated by an X and nucleotides indicated by an N are unknown.

FIG. 9A (HT-H) and FIG. 9B (SNG-M) show staining for trophinin while FIG. 9C (HT-H) and FIG. 9D (SNG-M) show staining for tastin. Scale bars=10 μM.

FIGS. 10A and 10B present immunofluorescence micrographs of placental tissues from early pregnancy stained via anti-trophinin antibodies. FIG. 10A shows a region of trophinin staining of the chorionic villus of a placenta obtained at seven weeks pregnancy. Fewer than half the villi in this tissue were stained for trophinin. Staining of trophinin in the villus in FIG. 10A is observed at the apical plasma membranes of the syncytiotrophoblasts. FIG. 10B is a chorionic villus of placenta obtained at nine weeks pregnancy. Lysosomal vesicles of the syncytiotrophoblasts in some villi show staining for trophinin. Scale bars=10 μM.

FIGS. 10C and 10D display immunofluorescence micrographs of endometrial epithelium stained via anti-trophinin antibodies. FIG. 10C shows staining for trophinin at the apical membrane (arrowheads) of the surface epithelium from early secretory phase (approximately day 16/17 of the menstrual cycle). FIG. 10D shows staining for trophinin in mucinous materials (arrow; in glandular lumen) associated with endometrial tubular epithelium from middle secretory phase (approximately day 22 of the menstrual cycle). Scale bars=10 μM.

FIGS. 11A and 11B shows an expanded blastocyst (*zona pellucida* removed) from a rhesus monkey under phase microscopy (11A) and after immunofluorescence staining with an anti-trophinin antibody (11B). The long arrows indicate cell mass in FIG. 11A while arrowheads indicate the embryonic pole in FIG. 11B Strong staining for trophinin is associated with cells of the trophectoderm (11B). Staining of cells located at the embryonic pole (arrowheads) is stronger than staining of cells versus cells located at the mural pole (small arrows). Scale bars=25 μM.

FIG. 11C shows a tissue section taken from the site of implantation of a 15 day macaque monkey blastocyst. A light micrograph shows endometrium (E), trophoblast (T), cytotrophoblasts of blastocyst (short arrow), anchoring villi of trophoblasts penetrating the endothelial epithelium (long arrows) and plaque cells in hypertrophic endometrial epithelium (asterisks). The border between the embryo and the uterine epithelium is indicated by a line. Scale bar=200 μM.

FIG. 11D is an immunofluorescence micrograph of a higher magnification of the same tissue section described in FIG. 11C (site located in brackets) stained with anti-trophinin antibodies to the N-terminal region of trophinin (residue 23–31). Trophoblast layer (T) and endometrial epithelium (E) show strong staining of trophoblast cells (triangles) and endometrial cells (arrows) located at the interface between the two tissues. Scale bar=10 μM.

DETAILED DESCRIPTION OF THE INVENTION

The present invention provides novel proteins involved in embryo adhesion to the uterus during implantation. The invention provides trophinin, which is present in the cell membrane of trophoblast cells and uterine epithelial cells. The invention also provides a family of cytoplasmic trophinin-assisting proteins, including tastin, bystin and lastin, which can interact with trophinin to effect cell adhesion.

Although the precise morphological events of implantation vary from species to species, an essential feature is the formation of allogenic and heterotypic cell-to-cell contact between embryonic and maternal cells. The early events of implantation include an initial apposition of the trophoblast to the uterus and subsequent adhesion of the trophoblast to the endometrial epithelium (Enders, et al. In *Cellular and Molecular Aspects of Implantation* (Plenum Press, New York, 1981); Kaufman, In *Biology of the Trophoblast* (Elsevier Scientific 1985); Aplin, *J. Reprod. Fert.* 91:525–541 (1991); Ringler and Strauss, *Current. Opin. Cell Biol.* 2:703–708 (1990)). The initial attachment of the trophoblast to the endometrial epithelium is unusual in that this cell-to-cell contact occurs via their respective apical cell membranes.

In general, the basal and lateral surfaces of epithelial cells rather than their apical surfaces provide sites for adhesion between cells. The unique ability of trophoblast and endometrial cells to adhere at their apical surfaces can be due to apical display of adhesion molecules normally located at the basal and lateral surfaces of the cells. For example, atypical expression of heparan sulfate and integrins on the surface of the mouse blastocyst at peri-implantation stage has been observed (Farach et al., *Devel. Biol.* 123:401–410 (1987); Sutherland et al., *J. Cell Biol.* 106: 1331–1348 (1988) ; Leivo et al., *Devel. Biol.* 76:100–114 (1980); Armant et al., *Devel. Biol.* 116: 519–523 (1986)). Alternatively, unique apical adhesion of trophoblast with endometrial epithelium can be mediated by unique cell surface molecules (Kliman et al., In *Blastocyst Implantation,* (Adams Publishing 1989)). Attempts to identify molecules involved in embryo implantation have been conducted both in vivo and in vitro (Lindenberg et al., *Hum. Reprod.* 1:533–538 (1988); Armant et al., supra, 1986; Leivo et al., supra, 1980; Sutherland et al., supra, 1988; Farach et al., supra, 1987; Yamagata and Yamazaki, *Biochem. Biophys. Res. Commun.* 181:1004–1009 (1991); Romagnano and Babiarz, *In vitro. Devel. Biol.* 141:254–261 (1990)), however, none of these studies have identified adhesion molecules that are unique to embryo implantation.

Figure 1A:
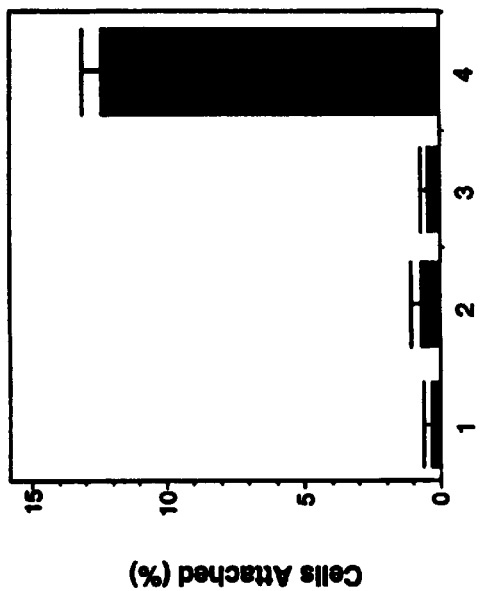
FIGS. 1A, 1B, 1C and 1D collectively show the results of in vitro adhesion cell assays evaluating the ability of cell lines to undergo trophinin-mediated cell adhesion.
Figure 1B:
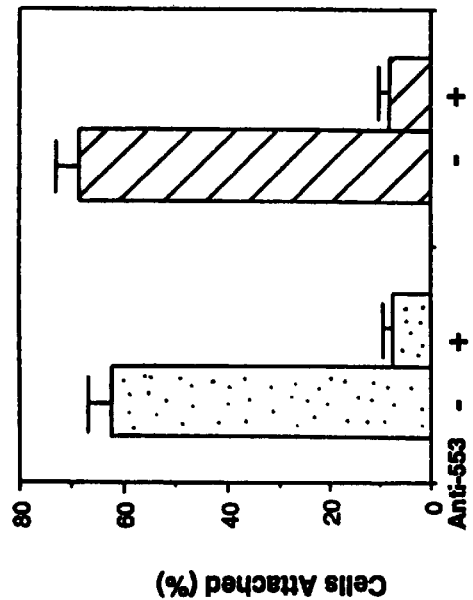

As disclosed herein, trophinin is involved in apical cell adhesion between cultured trophoblast HT-H cells and endometrial adenocarcinoma SNG-M cells (see FIG. 1A and 1B). Trophinin also mediates adhesion between HT-H and HT-H cells and between SNG-M and SNG-M cells (See Example I). In contrast, these two cell types do not adhere to other types of epithelial cells such as HeLa, A431, SW480 and HepG-2 cells (Table 1). Thus, adhesion between HT-H and SNG-M cells is cell-type specific.

Figure 3A:
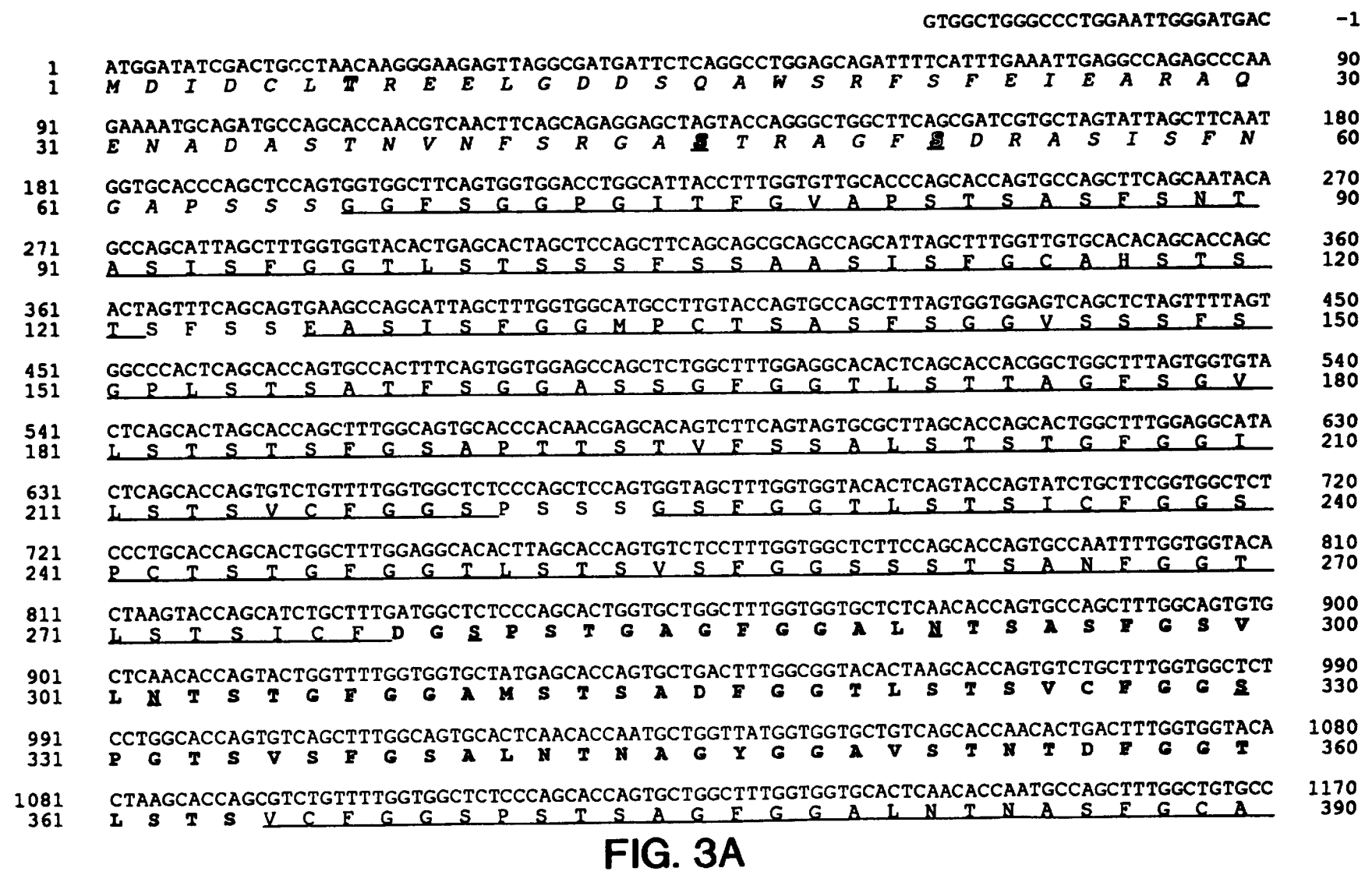
Figure 3B:
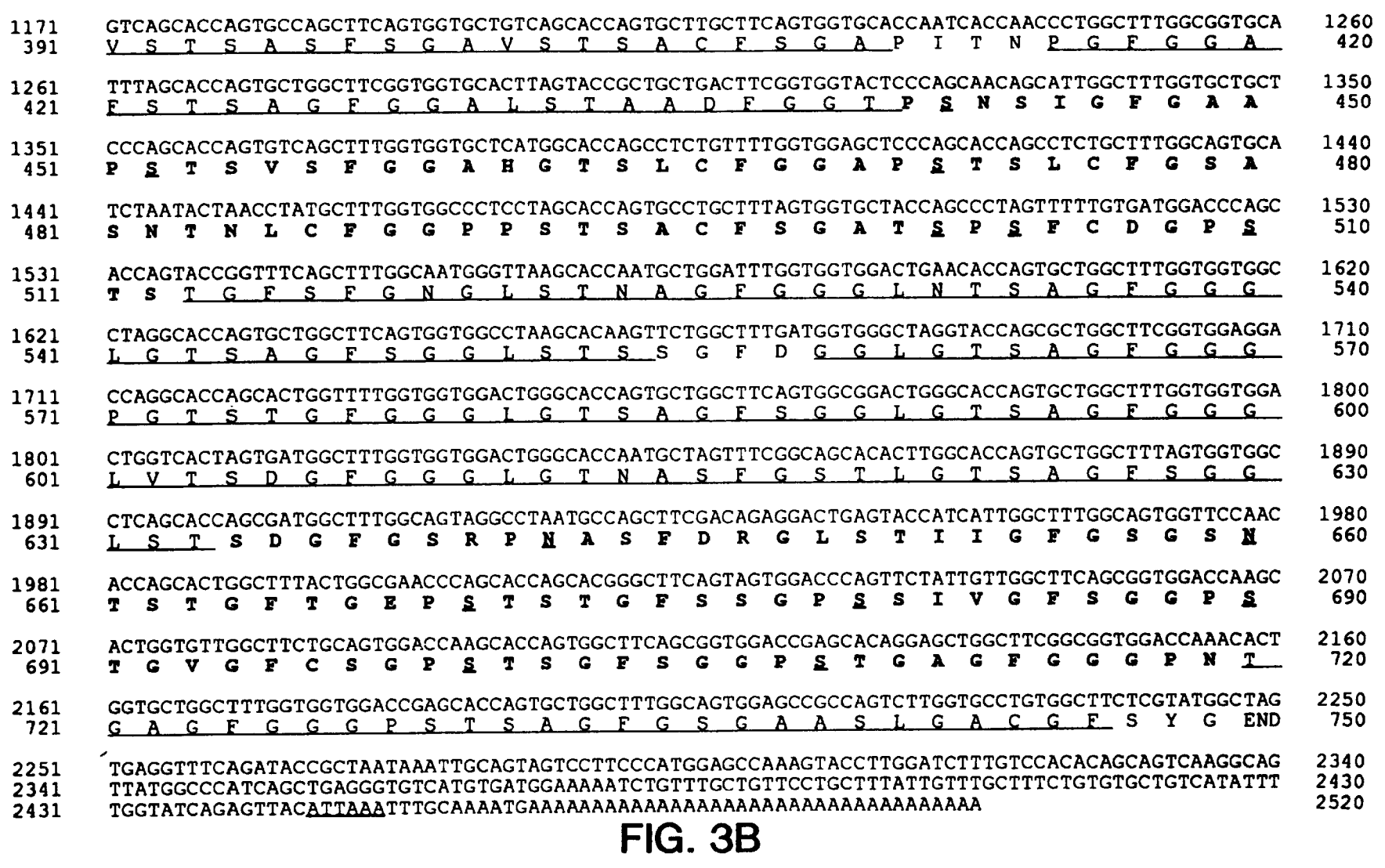

The invention provides a substantially purified mammalian trophinin having substantially the amino acid sequence of human trophinin shown in FIG. 3 (SEQ ID NO: 2). The amino acid sequence of trophinin was derived from the nucleotide sequence shown in FIG. 3 (SEQ ID NO: 1). As used herein, the term "substantially the amino acid sequence" means the amino acid sequence of human trophinin as shown in FIG. 3 (SEQ ID NO: 2), as well as amino acid sequences that are similar to SEQ ID NO: 2, but have one or more amino acid additions, deletions or substitutions that do not substantially alter the ability of the encoded protein to function like a trophinin and, for example, mediate cell adhesion or elicit trophinin specific antibodies. In general, an amino acid sequence having at least 65% sequence homology with the amino sequence of FIG. 3 (SEQ ID NO: 2) is considered substantially the same sequence. Thus, a mammalian trophinin is characterized, in part, by having a greater homology with other mammalian trophinins such as human trophinin as compared with other cell adhesion type molecules.

It is well recognized that various amino acids in a polypeptide can be replaced by other naturally- or non-naturally-occurring L- or D-amino acids having equivalent reactive side chains or by other chemical compounds without substantially changing the biological activity of the polypeptide. For example, a hydrophobic amino acid such as leucine can be replaced by another hydrophobic amino acid such as alanine without substantially changing the amino acid sequence or activity of a trophinin polypeptide. In addition, the N-terminus or C-terminus or a reactive side chain of an amino acid can be modified, for example, by acetylation or amidation, without substantially changing the activity of a trophinin polypeptide. Such modified proteins can have advantageous properties including, for example, increased stability in vivo or in vitro, and are considered to be within the meaning of the term "substantially the amino acid sequence."

As used herein, the term "substantially purified" means a protein that is in a form that is relatively free from contaminating lipids, proteins, nucleic acids or other material normally associated with a protein in a cell. Substantially purified trophinin can be obtained, for example, using well known biochemical methods of purification or by expressing a recombinant nucleic acid molecule encoding a trophinin such as the nucleic acid molecule shown in SEQ ID NO: 1. In addition, an amino acid sequence consisting of at least a portion of the amino acid sequence of SEQ ID NO: 2, can be chemically synthesized or can be produced by expressing a portion of the nucleotide sequence shown in SEQ ID NO: 1 (see Example V and VI).

As used herein, the terms "protein" or "polypeptide" are used in their broadest sense to mean a sequence of amino acids that can be encoded by a cellular gene or by a recombinant nucleic acid sequence or can be chemically synthesized. In some cases, the term "polypeptide" is used in referring to a portion of an amino acid sequence encoding a full length protein. An active fragment of trophinin as defined below can be an example of such a polypeptide. A protein can be a complete, full length gene product, which can be a core protein having no amino acid modifications or can be a post-translationally modified form of a protein such as a phosphoprotein, glycoprotein, proteoglycan, lipoprotein or nucleoprotein.

Trophinin is a cell membrane protein that is characterized primarily by its ability to effect cell adhesion. It is recognized that the ability of trophinin to effect cell adhesion can be due to a portion of the full length protein. For example, as discussed below, greater than 90% of trophinin is composed of a repeating decapeptide sequence that can be involved in binding to another trophinin molecule. Thus, a polypeptide that contains only a portion of the full length trophinin protein can be useful for mediating cell adhesion. As used herein, the term "trophinin" means the full length trophinin protein or an active fragment thereof. As used herein, the term "active fragment" means a portion of a full length protein, provided the portion retains at least one activity that is characteristic of the full length protein. For example, an active fragment of trophinin can be a portion of the full length trophinin protein that can effect cell adhesion or can elicit specific antibodies to trophinin. An active fragment of trophinin can be identified, for example, by expressing a portion of the trophinin protein in a cell and determining that the cell can adhere to a trophinin expressing cell (see Example I).

Figure 4:
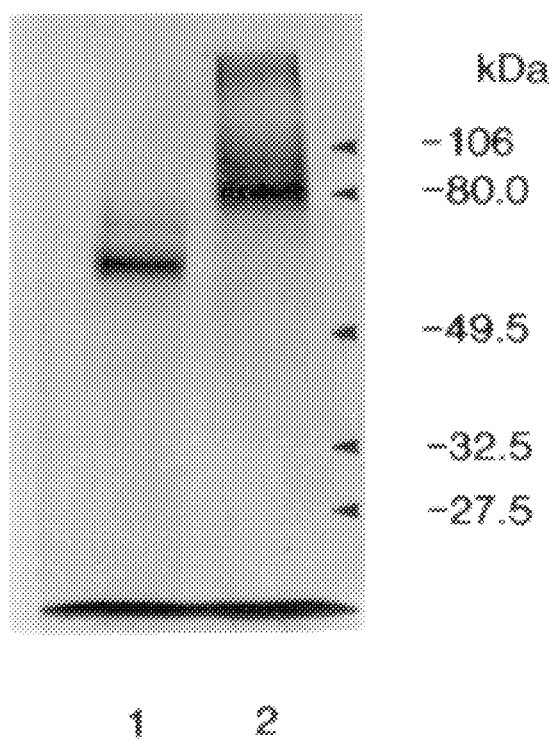

The complete amino acid sequence of human trophinin was deduced from the nucleotide sequence of a cDNA clone encoding human trophinin. The trophinin cDNA (SEQ ID NO: 1) contains an open reading frame coding for 749 amino acids (FIG. 3). Trophinin has no significant homology to sequences contained in protein and nucleic acid databases. In vitro translation of trophinin cDNA and analysis using sodium dodecyl sulfate polyacrylamide gel electrophoresis (SDS-PAGE) showed that trophinin is synthesized as a major product of 61 kiloDaltons (kDa) (FIG. 4). This experimentally determined molecular mass is in agreement with the predicted molecular mass of 69.29 kDa based on the cDNA open reading frame.

Hydropathy analysis (Kyte and Doolittle, *J. Mol. Biol.* 157:105–132 (1982)) of trophinin indicates trophinin is an intrinsic membrane protein having 8 separate transmembrane domains (FIG. 5A). The relative proportion of trophinin localized in the cytoplasm, in the membrane bilayer and on the cell surface is 10%, 56% and 34%, respectively. The amino terminal portion of trophinin is likely located in the cytoplasm because the first putative membrane spanning domain (amino acids 66 to 120) follows an arginine residue at position 54, which can function as a stop transfer signal during translocation into the endoplasmic reticulum, and because antibodies raised to an amino terminal peptide of trophinin (residues 23–31) react only with cells that have had their membranes permeabilized by detergent treatment (see Example VI).

The amino terminal region of trophinin contains many serine and threonine residues that can function as potential phosphorylation sites for enzymes such as casein kinase II (Kemp and Pearson, *Trends Biochem. Sci.* 15:342–346 (1990)), protein kinase C, and cAMP/cGMP dependent kinases (see Example III). Four potential N-glycosylation sites and thirteen potential O-glycosylation sites are present within the predicted cell surface domains of trophinin (FIG. 3).

Greater than 90% of trophinin is composed of a tandemly repeated decapeptide motif. There are 69 such repeat sequences, which exhibit some variation in sequence and length (FIG. 5B). Portions of the decapeptide motifs are contained within three regions of trophinin that are hydrophilic in character and are exposed on the external side of the cell plasma membrane. The external trophinin domains are located from amino acid positions 278 to 364 (SEQ ID NO: 20), 441 to 512 (SEQ ID NO: 21) and 634 to 719 (SEQ ID NO: 22) (see bold lettering in FIG. 3). Protein secondary structure algorithms (Garnier et al., *J. Mol. Biol.* 120:97–120 (1978); Gascuel and Golmard, *Comput. Appl. Biosci.* 4:357–365 (1988)) predict that the decapeptide repeats conform to a repeated β-turn structure, which can be involved in homophilic adhesion (not shown).

Figure 6A:
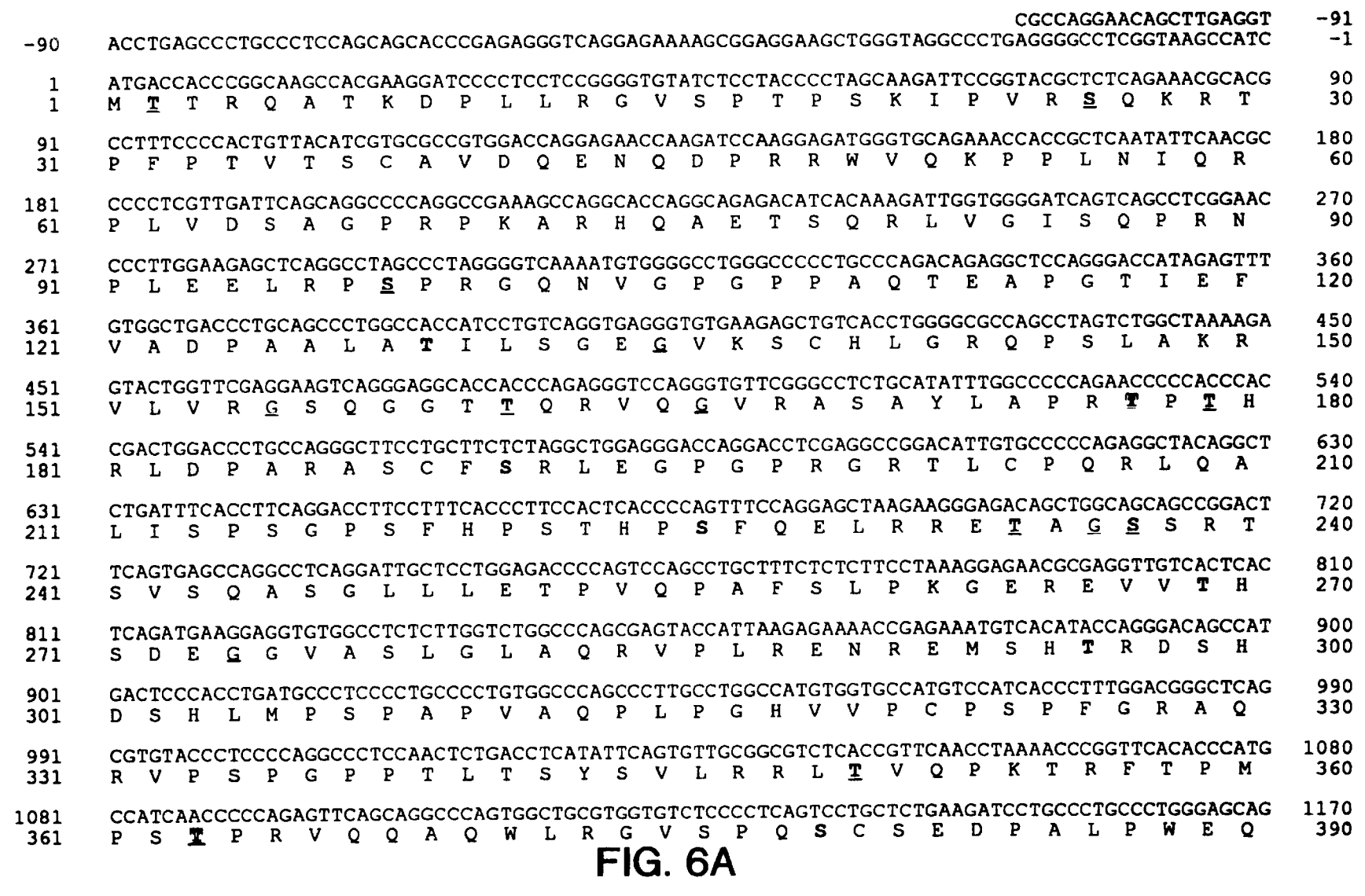

In addition to trophinin, a cell can require the expression of a trophinin-assisting protein in order to effect cell adhesion. The present invention provides a family of substantially purified mammalian trophinin-assisting proteins having substantially the amino acid sequences of human tastin (SEQ ID NO: 5), human bystin (SEQ ID NO: 7) and human lastin (SEQ ID NO: 9) as shown in FIGS. 6, 7 and 8, respectively. A trophinin-assisting protein can enable adhesion of cells that express trophinin. As used herein, the term "substantially the amino acid sequence" means the disclosed amino acid sequence of human tastin (SEQ ID NO: 5), human bystin (SEQ ID NO: 7) or human lastin (SEQ ID NO: 9) as well as amino acid sequences that are similar to SEQ ID NO: 5, SEQ ID NO: 7 or SEQ ID NO: 9, respectively, but have one or more amino acid additions, deletions or substitutions that do not substantially alter the ability of the encoded protein to function like a trophinin-assisting protein and, for example, mediate cell adhesion or elicit a trophinin-assisting protein specific antibody.

As used herein, the term "trophinin-assisting protein" is used generally to mean a member of the trophinin-assisting protein family of proteins as defined by their ability to assist trophinin in mediating adhesion of cells. Trophinin-assisting proteins include such family members as tastin, bystin or lastin and can be a full length trophinin-assisting protein or an active fragment of a trophinin-assisting protein. For example, amino acids 1 to 675 of lastin are a portion of the full length protein and can assist trophinin in mediating cell adhesion (see Example II). While not necessarily structurally related, trophinin-assisting protein family members are characterized, in part, by having the property of assisting trophinin mediated cell adhesion.

Trophinin and a trophinin-assisting protein can interact directly or indirectly to effect cell adhesion. For example, cell adhesion can be mediated by the direct binding of a trophinin-assisting protein to trophinin. Cell adhesion also can be due to a trophinin-assisting protein binding to another cellular molecule which then directly or indirectly binds to trophinin. Alternatively, a trophinin-assisting protein can interact indirectly with trophinin by binding to and eliminating the function of a negative regulator of trophinin activity in the cell.

A substantially purified trophinin-assisting protein can be obtained, for example, using well known biochemical methods of purification or by expressing a recombinant nucleic acid molecule encoding a trophinin-assisting protein such as the nucleic acid molecules shown in SEQ ID NO: 4, SEQ ID NO: 6 or SEQ ID NO: 8. In addition, an amino acid sequence consisting of at least a portion of the amino acid sequences of SEQ ID NO: 5, SEQ ID NO: 7 or SEQ ID NO: 9 can be chemically synthesized or can be produced by expressing a portion of the nucleotide sequence shown in SEQ ID NO: 4, SEQ ID NO: 6 or SEQ ID NO: 8, respectively.

The complete amino acid sequence of tastin (SEQ ID NO: 5) was deduced from the nucleotide sequence of the tastin cDNA clone and is shown in FIG. 6. The open reading frame of the tastin cDNA encodes a protein having 778 amino acids. Tastin exhibits an apparent molecular mass of about 80 kDa based on SDS-PAGE analysis of in vitro translated tastin cDNA (FIG. 4). This mass is consistent with a molecular weight of 83.75 kDa calculated from the tastin cDNA open reading frame. Tastin lacks a consensus signal sequence characteristic of a secreted protein and contains no transmembrane helices as assessed by hydropathy analysis (Kyte and Doolittle, supra, 1982). Thus, tastin has the characteristics of a cytoplasmic protein.

Tastin is rich in proline residues, which account for 15.3% of the total amino acids of the protein, and in cysteine residues. The majority of the cysteines are located between position 516 to 650 and occur primarily within four tandemly repeated sequences of 33 amino acids each (region denoted by italics in FIG. 6). Tastin contains many serine and threonine residues that are potential sites for phosphorylation, including two potential sites for cAMP/cGMP dependent kinase, sixteen sites for protein kinase C (Kemp and Pearson, supra, 1990), eleven sites for casein kinase II and two sites for MAP kinase (Gonzalez et al., *J. Biol. Chem.* 266:22159–22163 (1991)) (see Example IV).

Tastin has no overall significant homology to previously reported protein sequences. Nucleotide sequence homology analysis of tastin identified the sequence HFBCL29 (Genbank accession number M85643), which was derived from a human fetal brain cDNA library. HFBCL29 shows DNA base complementarity to a portion of tastin cDNA (positions 2057 to 2340). Thus, the HFBCL29 sequence can be homologous to a portion of the tastin sequence if HFBCL29 was recorded in the data base in the antisense direction. The protein sequence deduced from HFBCL29 is related to Y box binding protein-1 (Adams et al., Nature 355:632–634 (1992)). However, the entire nucleotide sequence and deduced amino acid sequence of tastin are not homologous overall to the Y-box binding protein-1.

The complete amino acid sequence of bystin was deduced from the nucleotide sequence of the bystin cDNA 20 clone and is shown in FIG. 7 (SEQ ID NO: 7). The open reading frame of the bystin cDNA codes for a protein of 306 residues. Bystin contains threonine and serine residues within potential sites for phosphorylation by protein kinase C (underlined) and casein kinase II (bolded). In addition, bystin contains tyrosine residues (bolded) that are potential sites of phosphorylation by tyrosine kinase and glycine residues within potential sites for myristoylation (bolded). Amino acid residues 1 to 88 of bystin show a significant degree of sequence homology to the bys gene previously identified in Drosophila (Stuart et al., *Mol. Cell. Biol.* 13:2524 (1993)).

A partial amino acid sequence of lastin was deduced from a partial nucleotide sequence of the lastin cDNA clone and is shown in FIG. 8 (SEQ ID NO: 9). The lastin cDNA clone does not contain the 3' end of the gene, including the stop codon and the poly-A tail. The open reading frame of the partial cDNA encodes for 675 amino acids. Lastin contains threonine and serine within potential sites for phosphorylation by protein kinase C (underlined) and casein kinase II (bolded). Lastin also contains potential sites for myristoylation of glycine residues.

The present invention also provides antibodies that are specifically reactive with trophinin or with a trophinin-assisting protein. As used herein, the term "antibody" is used in its broadest sense to include polyclonal and monoclonal antibodies, as well as polypeptide fragments of antibodies that retain a specific binding affinity for trophinin or a trophinin-assisting protein of at least about $1 \times 10^5 M^{-1}$. One skilled in the art would know that antibody fragments such as Fab, F(ab')$_2$ and Fv fragments can retain specific binding activity for their target antigen and, thus, are included within the definition of an antibody to trophinin or to a trophinin-assisting protein. In addition, the term "antibody" as used herein includes naturally occurring antibodies as well as non-naturally occurring antibodies such as domain-deleted antibodies (Morrison and Oi, WO 89/07142, Aug. 10, 1989, which is incorporated herein by reference) or single chain Fv (Ladner and Bird, U.S. Pat. No. 5,250,203, Nov. 9, 1993, which is incorporated herein by reference). Such non-naturally occurring antibodies can be constructed using solid phase peptide synthesis, can be produced recombinantly or can be obtained, for example, by screening combinatorial libraries consisting of variable heavy chains and variable light chains as described by Huse et al., *Science* 246:1275–1281 (1989), which is incorporated herein by reference.

Particularly useful non-naturally occurring antibodies include chimeric antibodies and humanized antibodies. Methods to produce chimeric antibodies and humanized antibodies by the method of CDR grafting are known in the art (see, for example, Winter, U.S. Pat. No. 5,225,539, Jul. 6, 1993, which is incorporated herein by reference).

As used herein, the term "chimeric antibody" means an antibody having a human constant region and a variable region from an organism other than a human. For example, a chimeric antibody useful in the invention can consist of a human IgG constant region and a variable region obtained from a mouse anti-human trophinin antibody. As used herein, the term "humanized antibody" means an antibody having constant and framework regions derived from human and hypervariable regions derived from an organism other than a human. For example, a humanized antibody useful in the invention can consist of the amino acids that form the hypervariable region of a mouse anti-human trophinin antibody and the amino acids that form the framework region and constant regions of a human IgG class antibody.

Chimeric antibodies and humanized antibodies are particularly useful for administration to a human subject, since the likelihood of an immune response by the subject against the antibody is minimized. Other non-naturally occurring antibodies within the present invention include bispecific antibodies, in which the antibody contains at least two different binding specificities that can be univalent or multivalent for each particular binding specificity. Methods for producing bispecific antibodies by chemical crosslinking or by heterohybridoma formation are well known in the art (for trivalent antibodies, see, for example, Ahlem and Huang, U.S. Pat. No. 5,273,743, Dec. 28, 1993), which is incorporated herein by reference) .

An anti-trophinin antibody or an anti-trophinin-assisting protein antibody can be prepared using substantially purified trophinin or a trophinin-assisting protein, respectively, either of which can be obtained from natural sources or produced by recombinant DNA methods or chemical synthesis. For example, recombinant DNA methods can be used to express trophinin alone or as a fusion protein, which can facilitate purification of the antigen and enhance its immunogenicity (see Example II). Similarly, an active fragment of trophinin or of a trophinin-assisting protein also can be obtained as described above and can be used as an immunogen (see Example V). If not sufficiently immunogenic, such fragments or peptides can be made immunogenic by expressing the hapten as a fusion protein or by coupling the hapten to a immunogenic carrier molecule such as bovine serum albumin or keyhole limpet hemocyanin (KLH). Various other carrier molecules and methods for coupling a non-immunogenic peptide to a carrier molecule are well known in the art (see, for example, Harlow and Lane, *Antibodies: A laboratory Manual* Cold Spring Harbor Laboratory Press, (1988), which is incorporated herein by reference). Methods for raising an antibody are routine and described, for example, by Harlow and Lane (supra, 1988).

An antiserum containing polyclonal antibodies to trophinin or to a trophinin-assisting protein can be raised in rabbits, goats or other animals. The resulting antiserum can be processed by purification of an IgG antibody fraction using protein A Sepharose chromatography and, if desired, can be further purified by affinity chromatography using, for example, Sepharose conjugated with a peptide antigen (see Example V) . The ability of polyclonal antibodies to specifically bind to a given molecule can be manipulated, for example, by dilution or by adsorption to remove crossreacting antibodies to a non-target molecule. Methods to manipulate the specificity of polyclonal antibodies are well known to those in the art (See Harlow and Lane, supra, 1988).

A monoclonal anti-trophinin or anti-trophinin-assisting protein antibody can be produced using known methods (Harlow and Lane, supra, 1988). Essentially, spleen cells from a trophinin- or a trophinin-assisting protein-immunized animal can be fused to an appropriate myeloma cell line such as SP2/0 myeloma cells to produce hybridoma cells. Cloned hybridoma cell lines can be screened using a labeled trophinin or trophinin-assisting protein polypeptide to identify clones that secrete an appropriate monoclonal antibody. A trophinin or a trophinin-assisting protein polypeptide can be labeled as described below. A hybridoma that expresses an antibody having a desirable specificity and affinity can be isolated and utilized as a continuous source of monoclonal antibodies. Methods for identifying an anti-trophinin or anti-trophinin-assisting protein antibody having an appropriate specificity and affinity and, therefore, useful in the invention are known in the art and include, for example, enzyme-linked immunoadsorbance assays, radioimmunoassays, precipitin assays and immunohistochemical analyses (see for example, Harlow and Lane, supra, 1988; chap. 14).

Figure 1C:
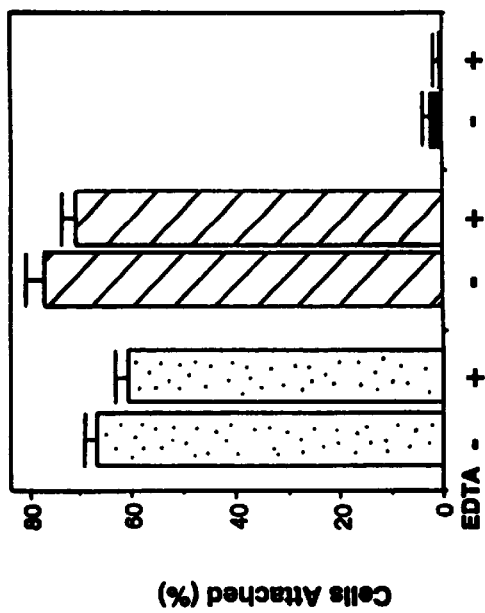
Figure 1D:
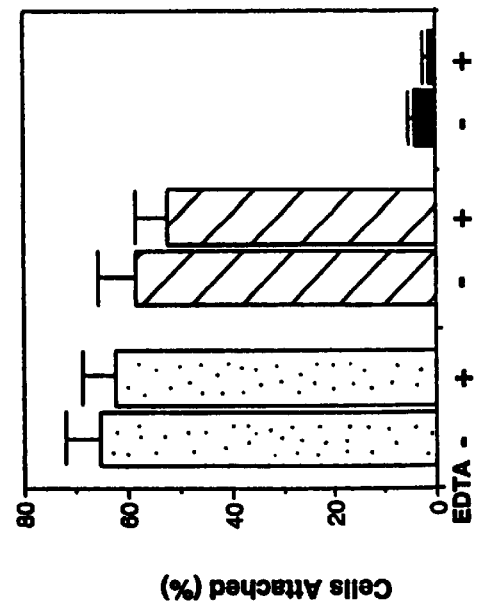

An anti-trophinin antibody can be characterized by its ability to bind a portion of a mammalian trophinin protein, such as the portion of trophinin that is exposed on the external side of the plasma membrane of a cell (see, for example, FIG. 1D). An anti-trophinin-assisting protein antibody can be characterized by its ability to bind to an epitope that is unique to one or more members of the trophinin-assisting protein family of proteins.

An anti-trophinin antibody or an anti-trophinin-assisting protein antibody of the invention can be useful to purify trophinin or a trophinin-assisting protein, respectively, from a sample. For example, an anti-trophinin antibody can be attached to a solid substrate such as a resin and can be used to affinity purify trophinin. In addition, an anti-trophinin antibody can be used to identify the presence of trophinin in a sample. In this case, the antibody can be labeled with a detectable moiety such as a radioisotope, an enzyme, a fluorochrome or biotin. An anti-trophinin or anti-trophinin-assisting protein antibody can be detectably labeled using methods well known in the art (see, for example, Harlow and Lane, supra, (1988); chap. 9). Following contact of a labeled antibody with a sample such as a tissue homogenate or a histological section of a tissue, specifically bound labeled antibody can be identified by detecting the labeled moiety.

A labeled second antibody also can be used to identify specific binding of an unlabeled anti-trophinin or anti-trophinin-assisting protein antibody. A second antibody generally will be specific for the particular class of the first antibody. For example, if an anti-trophinin antibody is of the IgG class, a second antibody will be an anti-IgG antibody. Such second antibodies are readily available from commercial sources. The second antibody can be labeled using a detectable moiety as described above. When a sample is labeled using a second antibody, the sample is first contacted with a first antibody, then the sample is contacted with the labeled second antibody, which specifically binds to the first antibody and results in a labeled sample. Alternatively, a labeled second antibody can be one that reacts with a chemical moiety, for example biotin or a hapten that has been conjugated to the first antibody (see for example, Harlow and Lane, supra (1988); chapter 9).

The present invention also provides nucleic acid molecules encoding trophinin or a trophinin-assisting protein. Nucleic acid molecules encoding the disclosed proteins, which are involved in mediating apical cell adhesion, were obtained by functional selection from an expression cDNA library (see Example II). Essentially, a cDNA library was prepared from HT-H cells and transfected into non-adhering COS-1 cells, which then were selected for adherence to SNG-M cells. Both trophinin and trophinin-assisting protein clones were simultaneously discovered since COS-1 cells only became adherent following co-transfection with a trophinin and a trophinin-assisting protein cDNA sequence (see FIG. 1C).

The present invention provides a substantially purified nucleic acid molecule encoding a mammalian trophinin. For example, the invention provides a substantially purified nucleic acid molecule encoding human trophinin having substantially the nucleotide sequence shown in FIG. 3 (SEQ ID NO: 1). As used herein, the term "substantially purified" means that the nucleic acid is relatively free from contaminating materials such as lipids, proteins, carbohydrates or cellular material normally associated with a nucleic acid in a cell. For example, a nucleic acid molecule that is chemically synthesized is considered substantially purified. Recombinant DNA methods for producing a substantially purified nucleic acid are well known in the art and include cloning a sequence or polymerase chain reaction (PCR) amplification of a sequence (see Sambrook et al., *Molecular Cloning: A laboratory manual* (Cold Spring Harbor Laboratory Press 1989), which is incorporated herein by reference; see, also, Erlich, *PCR Technology: Principles and applications for DNA amplification* (Stockton Press 1989), which is incorporated herein by reference). As used herein, the term "substantially the nucleotide sequence" means a sequence that contains, for example, different nucleotides than shown in FIG. 3 (SEQ ID NO: 1) but that, as a result of the degeneracy of the genetic code, encodes substantially the same amino acid sequence as shown in FIG. 3 (SEQ ID NO: 2). Such nucleotide sequences can be either DNA or RNA and can encode either the coding or non-coding nucleotide strand.

The cloned nucleic acid molecule encoding trophinin (SEQ ID NO: 1) contains 2524 nucleotides with an open reading frame encoding 749 amino acids (see FIG. 3). The 3' untranslated region of trophinin consists of 250 nucleotides and contains a polyadenylation signal located twelve nucleotides upstream of the poly-A tail. Among the ATG codons in the 5' region, the sequence around the ATG at position 1 (see FIG. 3) closely matches a Kozak sequence optimal for translation initiation (Kozak, *Nucleic Acid Res.* 12, 857–872, (1984)). No other ATG codon near the 5' end conforms to the consensus sequence for translation initiation. In vitro translation of the trophinin cDNA confirms that the ATG beginning at position 1 in FIG. 3 encodes the initiation methionine in trophinin.

The invention also provides a nucleotide sequence that can hybridize to a portion of the nucleic acid molecule encoding trophinin under relatively stringent hybridization conditions. Relatively stringent hybridization conditions can be determined empirically or can be estimated based, for example, on the relative GC:AT content of the hybridizing nucleotide sequence and the target sequence, the length of the hybridizing nucleotide sequence and the number, if any, of mismatches between the hybridizing nucleotide sequence and the target sequence. The extent of hybridization can be controlled, for example, by the temperature, pH or ionic strength of the hybridization reaction mixture or the subsequent wash solutions (Sambrook et al., supra, 1989).

A nucleotide sequence useful for hybridizing to a nucleic acid molecule encoding trophinin should be at least ten nucleotides in length and can be prepared, for example, by restriction endonuclease digestion of a cloned nucleic acid molecule, such as the nucleic acid molecule shown in FIG. 3 (SEQ ID NO: 1), by PCR amplification of a portion of a nucleic acid encoding trophinin or by chemical synthesis using well known methods. A nucleotide sequence can be labeled with a detectable moiety and can be used as a probe to detect a nucleic acid molecule or as a primer for PCR. Methods for detectably labeling a nucleic acid are well known in the art (see, for example, Sambrook et al., supra, 1989; see, also, Ausubel et al., Current Protocols in Molecular Biology (John Wiley & Sons 1987), which is incorporated herein by reference).

The invention also provides a substantially purified nucleic acid molecule encoding a trophinin-assisting protein. For example, the invention provides a substantially purified nucleic acid molecule encoding human tastin, bystin or lastin having substantially the nucleotide sequence shown in FIG. 6 (SEQ ID NO: 4), FIG. 7 (SEQ ID NO: 6) and FIG. 8 (SEQ ID NO: 8), respectively.

The nucleic acid molecule encoding tastin (SEQ ID NO: 4) contains 2,577 nucleotides having an open reading frame encoding 778 amino acids (see FIG. 6). The 3' untranslated region contains 128 nucleotides and has a polyadenylation signal located eleven nucleotides upstream of the poly-A tail. The nucleotide sequence around the ATG at position 1 conforms to the consensus sequence for the translation initiation site (Kozak, supra, 1984). In vitro translation of the tastin cDNA confirms that the ATG beginning at position 1 in FIG. 6 encodes the initiation methionine in tastin.

The nucleic acid molecule encoding bystin (SEQ ID NO: 6) contains 1,293 nucleotides having an open reading frame encoding 306 amino acids (see FIG. 7). The 3' untranslated region consists of 306 nucleotides.

The nucleic acid molecule encoding lastin is based on the sequence of a partial cDNA clone (SEQ ID NO: 8) that contains 2,223 nucleotides having an open reading frame encoding 675 amino acids beginning at the ATG start site (see FIG. 8). The 5' untranslated region consists of 198 nucleotides. The nucleotide sequence around the ATG at position 1 conforms to the consensus sequence for the translation initiation site (Kozak, supra, 1984).

The invention also provides a nucleotide sequence encoding a trophinin-assisting protein that can hybridize to a nucleic acid molecule under relatively stringent hybridization conditions. A nucleotide sequence encoding a trophinin-assisting protein should be at least ten nucleotides in length and can be prepared as described above.

The invention provides vectors containing a nucleic acid molecule encoding a mammalian trophinin or a mammalian trophinin-assisting protein and host cells containing the vectors. Vectors are well known in the art and include, for example, cloning vectors and expression vectors, as well as plasmids or viral vectors (see, for example, Goedell, Methods in Enzymology, vol. 185 (Academic Press 1990), which is incorporated herein by reference). For example, an expression vector that contains a nucleic acid molecule encoding trophinin can be particularly useful for expressing large amounts of trophinin protein, which can be purified and used as an immunogen to raise anti-trophinin antibodies. A baculovirus vector is an example of a vector that can be used to express large amounts of trophinin or a trophinin-assisting protein. A vector containing a nucleic acid molecule encoding a trophinin or a trophinin-assisting protein can also contain a promoter or enhancer element, which can be constitutive or inducible and, if desired, can be tissue specific. Host cells also are known in the art and can be selected based on the particular vector. An appropriate host cell can be selected based, on the particular vector used, for example, baculovirus transfer vectors can be used with baculovirus DNA to infect insect cell lines such as SF21 cells.

An expression vector can also be used to effect the ability of cells to undergo trophinin-mediated cell adhesion. A variety of nucleic acid molecules can be used to effect cell adhesion under various situations. For example, an expression vector that contains a nucleic acid molecule encoding trophinin can be introduced into a cell that previously expressed an insufficient level of trophinin to mediate cell adhesion. Under the appropriate conditions, cells containing such expression vectors can increase their expression of trophinin, thus enhancing their ability to undergo trophinin mediated cell adhesion. In addition, an expression vector containing a nucleic acid molecule encoding a trophinin-assisting protein can be used to increase trophinin-mediated cell adhesion by introducing the expression vector into cells that fail to exhibit trophinin-mediated cell adhesion due to a deficiency in the expression of a trophinin-assisting protein.

An expression vector also can contain an exogenous nucleic acid molecule encoding an antisense nucleotide sequence that is complementary to a nucleotide sequence encoding a portion of trophinin. When introduced into a cell under the appropriate conditions, such an expression vector can produce the antisense nucleic acid molecule, which can selectively hybridize to the trophinin gene or to an RNA molecule encoding trophinin in a cell and, thereby, affect trophinin expression in the cell. For example, the antisense nucleic acid molecule can hybridize to a trophinin gene in the cell and can reduce or inhibit transcription of the trophinin gene. Also, the antisense molecule can hybridize to the an RNA molecule encoding trophinin in the cell and can reduce or inhibit translation, processing and cell stability or half-life of the RNA.

Expression vectors also can be used to effect trophinin-mediated cell adhesion by introducing into a cell an exogenous nucleic acid molecule encoding a ribozyme that can specifically cleave RNA encoding trophinin. Introducing an expression vector into a cell and expressing a ribozyme specific for an RNA encoding trophinin can reduce or inhibit trophinin expression. An antisense nucleic acid molecule or a ribozyme can be chemically synthesized and incorporated into an expression vector using recombinant DNA techniques. An antisense nucleic acid molecule or a ribozyme also can be added directly to a cell without having been incorporated into the expression vector.

The above described methods for effecting trophinin-mediated cell adhesion by using an expression vector to obtain expression of an exogenous nucleic acid molecule in a cell also can be accomplished if the exogenous nucleic acid molecule encodes a trophinin-assisting protein or an antisense or ribozyme sequence specific for a trophinin-assisting protein. For example, an increase in trophinin-mediated cell adhesion can be achieved by introducing an expression vector encoding a trophinin-assisting protein into cells that are deficient in trophinin-assisting protein expression or produce a non-functional trophinin-assisting protein. In addition, a decrease in trophinin-mediated cell adhesion can be accomplished by introducing into a cell an expression vector that encodes for an antisense or ribozyme specific for a trophinin-assisting protein. In such cases the expressed antisense or ribozyme can reduce or inhibit trophinin-mediated cell adhesion by decreasing the effective level of trophinin-assisting protein in a cell below that required to effect trophinin-mediated cell adhesion.

The ability of cells to undergo trophinin-mediated cell adhesion also can be effected by introducing two or more expression vectors into a cell, each encoding a different exogenous nucleic acid molecule or introducing an expression vector capable of expressing more than one exogenous nucleic acid molecule. To reduce or inhibit the level of expression of trophinin, for example, expression vectors coding for both an antisense and a ribozyme specific for trophinin can be introduced into a cell. The expression of both such exogenous nucleic acid sequences simultaneously in a cell can be more effective at reducing trophinin expression than when either sequence is expressed alone.

Methods for introducing expression vectors into cells are well known in the art. Such methods are described in Sambrook et al supra (1989) and in Kriegler M. *Gene Transfer and Expression: A Laboratory Manual* (W. H. Freeman and Co. New York N.Y. (1990), which is incorporated herein by reference) and, include, for example, transfection methods such as calcium phosphate, electroporation or lipofection, or viral infection.

Recombinant viral vectors are available for introducing exogenous nucleic acid molecules into mammalian cells and include, for example, adenovirus, herpesvirus and retrovirus-derived vectors. For example, a viral vector encoding trophinin or a trophinin-assisting protein can be packaged into a virus to enable delivery of the genetic information and expression of these proteins in endometrial cells following infection by the virus. Also, a recombinant virus which contains an antisense sequence or a ribozyme specific for a nucleotide sequence encoding trophinin or a trophinin-assisting protein can be used to reduce or inhibit the ability of trophinin to mediate cell adhesion in cells infected by the virus.

Recombinant viral infection can be more selective than direct DNA delivery due to the natural ability of viruses to infect specific cell types. This natural ability for selective viral infection can be exploited to limit infection to specific cell types within a mixed cell population. For example, adenoviruses can be used to restrict viral infection principally to cells of epithelial origin. In addition, a retrovirus can be modified by recombinant DNA techniques to enable expression of a unique receptor or ligand that provides further specificity to viral gene delivery. Retroviral delivery systems can also provide high infection rates, stable genetic integration, and high levels of exogenous gene expression.

As described above, recombinant viral delivery systems exist that provide the means to deliver genetic information into a selected type of cell. The choice of viral system will depend on the desired cell type to be targeted, while the choice of vector will depend on the intended application. Recombinant viral vectors are readily available to those in the art and can be easily modified by one skilled in the art using standard recombinant DNA methods.

The invention also provides methods to detect trophinin or a nucleic acid molecule encoding trophinin in a sample using an agent that specifically binds to trophinin or to a nucleic acid molecule encoding trophinin. As used herein the term "agent" means a chemical or biological molecule that can specifically bind to trophinin or to a trophinin-assisting protein or to a nucleic acid molecule encoding trophinin or a trophinin-assisting protein. For example, an agent specific for trophinin can be another trophinin molecule or can be an anti-trophinin antibody. In addition, an agent can be a nucleotide sequence that binds to a nucleic acid molecule encoding trophinin or a trophinin-assisting protein.

As used herein, "sample" means a specimen such as a cell, tissue or an organ, which can be obtained, for example, by biopsy from a subject or can be a serum, urine or mucin specimen obtained from a subject. A sample containing trophinin can be used directly or can be processed prior to testing. For example, a biopsy tissue sample can be cut into tissue sections for histologic examination or can be further processed to release trophinin from cells within the tissue. Methods to process a sample such as a tissue, cells or a biological fluid for detecting a protein are known in the art (see, for example, Harlow and Lane, supra, (1988)).

The presence of trophinin in a sample can be determined by contacting the sample with an agent that can bind to trophinin under suitable conditions, which allow the agent to specifically bind to trophinin. Suitable conditions can be achieved using well known methods and can be optimized, for example, by varying the concentration of reactants or the temperature of the reaction. After the agent specifically binds to trophinin in a sample, the presence of trophinin can be determined by detecting specific binding of the agent.

An agent that can be detectably labelled can be used as a probe. For example, a probe for detecting the presence of trophinin in a sample can be an anti-trophinin antibody that is detectably labelled or that can be bound by a second antibody that is detectably labelled. In addition, a probe for detecting a nucleic acid molecule encoding trophinin or a trophinin-assisting protein can be an agent such as a nucleotide sequence that can hybridize to the nucleic acid molecule and that can be detected directly, for example, by a radioactive moiety incorporated into the nucleotide sequence, or indirectly, for example, by PCR analysis.

As used herein, "detectable label" means a molecule whose presence can be detected due to a physical, chemical or biological characteristic of the molecule. Detectable labels include, for example, radioisotopes, fluorescent molecules, enzyme/substrate systems, or visually detectable molecules. Methods to produce a probe for detecting a protein are well known in the art (see, for example, Harlow and Lane, supra, (1988)) and include, for example labelling the agent with a radioisotope, fluorescence molecule or histochemically useful enzyme or visible particle or colloid. Methods to produce a probe for detecting a nucleic acid molecule are also well known in the art (see, for example, Sambrook et al, supra, 1989; Hames and Higgins, *Nucleic acid Hybridization: a practical approach,* IRL press, New York, (1985), which are incorporated herein by reference).

An agent often can bind to a limited but detectable level of non-target substances such as the assay container and can result in background binding. Thus, to properly conclude that the presence of an agent binding in a sample represents the presence of trophinin, it is necessary to determine that the specific binding observed in a sample is greater than the background binding of the agent. The level of background binding of an agent can be determined using a control sample, which is similar in composition to the sample being tested but which contains a defined amount of trophinin or no trophinin.

The invention also provides methods to detect a trophinin-assisting protein in a sample using an agent that specifically binds to a trophinin-assisting protein. Such an agent can be an anti-trophinin-assisting protein antibody that specifically binds to a particular trophinin-assisting protein such as tastin, bystin and lastin. The presence of a trophinin-assisting protein in a sample can be determined using the methods described above.

A nucleic acid molecule encoding trophinin can be detected in a sample using an agent such an antisense nucleotide sequence that is specific for trophinin as described above. The target nucleic acid molecule can be extracted from a sample by methods well known in the art (See Sambrook et al., supra, 1989). Methods to detect the presence of a particular nucleic acid molecule within a population of nucleic acid molecules are well known to those in the art and include, for example, Southern blotting, northern blotting, slot blotting and PCR amplification (see, for example, Sambrook et al., supra, 1989). In situ hybridization also can be particularly useful for identifying nucleic acids in a sample (see for example, Pardue, in *Nucleic Acid Hybridisation: a practical approach* (IRL Press, 1991), which is incorporated herein by reference).

To detect a nucleic acid molecule encoding trophinin in a sample, the sample is contacted with a nucleotide sequence probe that can hybridize to a nucleic acid molecule encoding trophinin under relatively stringent conditions. The presence of a nucleic acid molecule encoding trophinin in the sample can be determined, for example, by detecting the presence of a specifically bound nucleotide sequence probe. The degree of background binding of the probe also can be determined in a control sample to confirm that binding seen in the sample is due to the presence of the target nucleic acid molecule.

A nucleic acid molecule encoding a trophinin-assisting protein also can be detected in a sample using methods as described above. For this purpose, the agent can be a nucleotide sequence specific for a nucleic acid molecule encoding a single trophinin-assisting protein such as tastin. The target nucleic acid molecule can be extracted from the sample or can be directly detected by in situ hybridization.

A combination of both protein detecting and nucleic acid detecting methods, when used together, can provide more information than either method used alone. For example, when the expression of RNA encoding trophinin and tastin was evaluated in samples of human tissues by northern blotting, low levels of trophinin mRNA and tastin mRNA were observed in placenta, lung and liver. However, immunofluorescence analysis of these tissues using anti-trophinin antibodies and anti-tastin antibodies was negative for these tissues except for macrophages present in the tissues (not shown). Thus, the combination of nucleic acid hybridization and immunofluorescence techniques together demonstrated that trophinin and tastin are not expressed by the majority of cell types within the body but are expressed by macrophages which are resident in certain tissues.

Figure 10A:
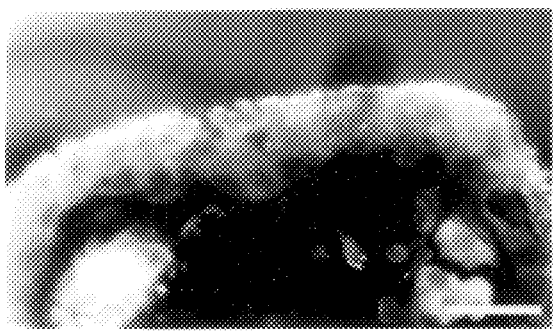
FIGS. 10A, 10B, 10C and 10D are immunofluorescence micrographs showing staining of trophinin and tastin in various human tissues as detected by antibodies to the N-terminal region of trophinin (residue 23–31) and the N-terminal region of tastin (residue 41–49).
Figure 10C:
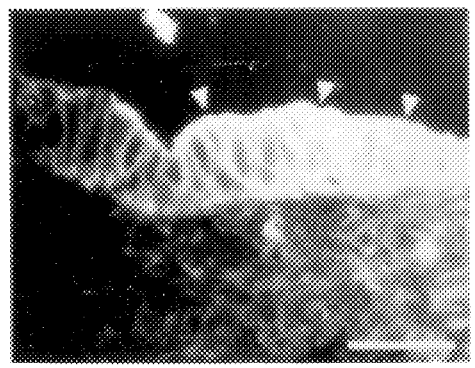
Figure 10B:
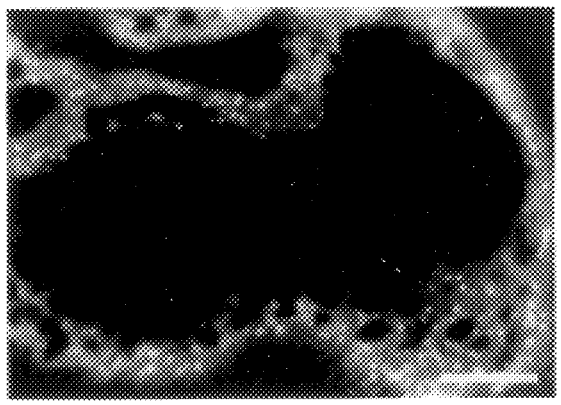

The expression of trophinin in vivo indicates that trophinin has a role in human embryo implantation. For example, immunofluorescence studies using anti-trophinin antibodies demonstrated that trophinin was absent in term placental tissues. Although trophinin was absent from the majority of placental tissues from early (7–10 week) pregnancy (except for macrophages), trophinin was readily detected in focal regions in the apical plasma membranes of syncytiotrophoblasts of chorionic villi at 7 weeks pregnancy (FIG. 10A). Trophinins also were found in cytoplasmic vesicles of syncytiotrophoblasts in the chorionic villi from 7–10 week pregnancy (FIG. 10B). Double immunostaining with the lamp-1 lysosome marker (Fukuda, *J. Biol. Chem.* 266:21327–21330 (1991), which is incorporated herein by reference) showed co-localization of trophinin and lamp-1 in these vesicles, indicating that trophinins are present in lysosomes or endosomes. These results indicate that trophinin expression is strictly regulated in vivo and is present on the surface of syncytiotrophoblasts at early stages of pregnancy but not at later stages of pregnancy. Trophinins that are present in lysosomes of syncytiotrophoblasts at later stages of pregnancy can be undergoing degradation following removal from the cell surface. Tastin was not detected in most of the chorionic villi from 7–10 week pregnancy, except that a weak signal was observed in the lysosomes of the syncytiotrophoblasts.

In addition to expression by the embryo, trophinin also is expressed in the uterus at the apical plasma membrane of the surface epithelium on day 16/17 endometrium (FIG. 10C), but not in endometrium during the proliferation stage (day 6–13) or ovulation stage (day 14). Endometrial biopsy samples taken from the late secretory phase (day 20–28) showed staining for trophinin in the mucin. Tastin could not be detected in any of the above endometrial samples except for mucin. These results, like those for the embryo, demonstrate that trophinin expression is strictly regulated in endometrial tissue and is present for only a short time on the cell surface. The expression of trophinin is consistent with the concept of an implantation window for embryo implantation (Yoshinaga, *Biochem. Biophys. Res. Comm.* 181:1004–1009 (1988); Harper, *Ballieres Clin. Obstet. Gynaecol.* 6:351–371 (1992)).

Figure 10D:
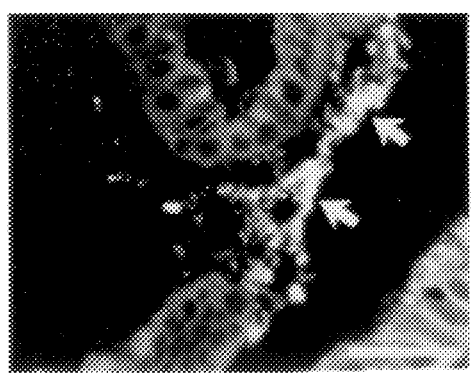

The level of trophinin or of a trophinin-assisting protein in a sample of endometrial tissue can be diagnostic of infertility due to failure of implantation. For example, insufficient expression of trophinin in endometrial epithelial cells or in trophoblast cells of the embryo can result in a failure of implantation. As described above, agents to detect trophinin or a trophinin-assisting protein can be used to detect the level of these proteins or can be used to detect the level of nucleic acid molecules encoding these proteins at various times during the menstrual cycle. For example, immunofluorescence staining with anti-trophinin antibodies showed that trophinin was present in mucin shed from endometrial epithelium of late secretory phases (day 20–28; see FIG. 10D) . With implantation of the embryo, mucin shedding from the endometrial epithelium does not occur. Thus, the disclosed methods to detect trophinin are useful for testing for the absence of pregnancy since detection of trophinin shed into body fluids, for example, in cervical mucus or in serum, can provide an early indication that implantation had not occurred and therefore, that the individual was not pregnant.

Figure 2A:
FIGS. 2A, 2B, 2C and 2D are electron micrographs showing the interface between adherent HT-H and SNG-M cells. HT-H cells were added to a monolayer of SNG-M cells and electron micrographs were taken after 10 min, 6 hr or 4 days of culture.
Figure 2B:
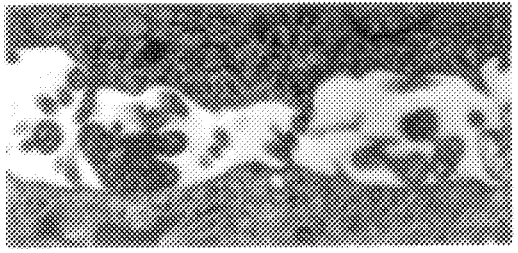
Figure 2C:
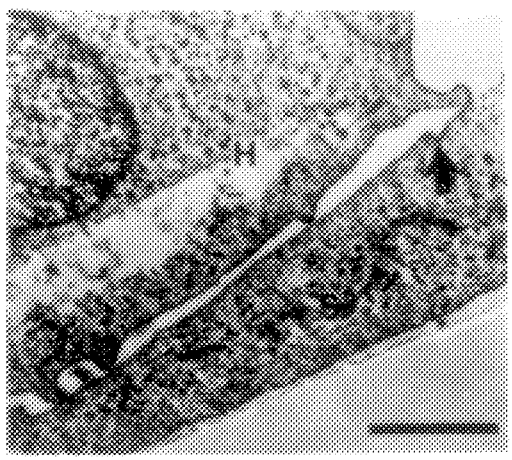
Figure 2D:
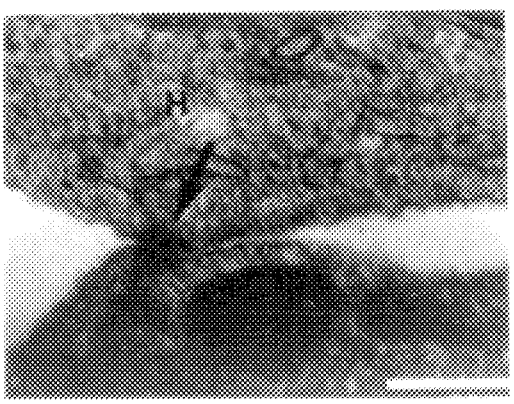

The ability to adhere cells at their apical surfaces using the methods described in the present invention can have a significant effect on cell morphology and function as exemplified by adhesion of HT-H cells to SNG-M cells. Initial cell attachment of HT-H to SNG-M cells is associated with the extension of the microvilli from one cell to another (FIGS. 2A and 2B). Within 6 hr after co-culture, each microvillus becomes flattened into the plasma membrane (FIG. 2C) and adherent junctions appear after 20 hr of co-culture (not shown). Desmosomes are formed between HT-H and SNG-M cells at sites in the plasma membrane that were originally the upper (apical) surface of these cells (FIG. 2D). This finding contrasts to the situation in typical epithelial cells where desmosomes normally form in plasma membranes located at the lateral or basal sides of the cell. The ability to form desmosomes at a new membrane surface can result from a sequential reorganization of the proteins that control the structure and polarity of epithelial cells.

Figure 9A:
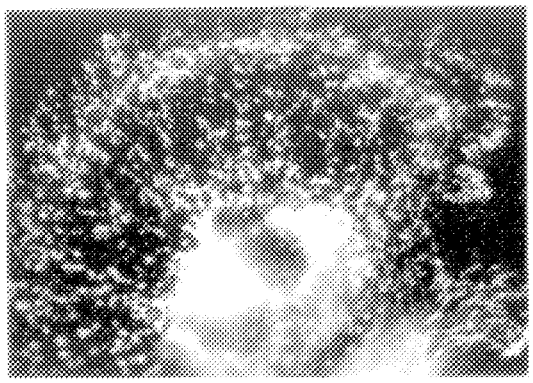
FIGS. 9A, 9B, 9C and 9D are immunofluorescence micrographs detailing expression of trophinin or tastin in HT-H cells and SNG-M cells as detected by antibodies to the N-terminal region of trophinin (residue 23–31;SEQ ID NO: 10) and the N-terminal region of tastin (residue 41–49;SEQ ID NO: 11).
Figure 9B:
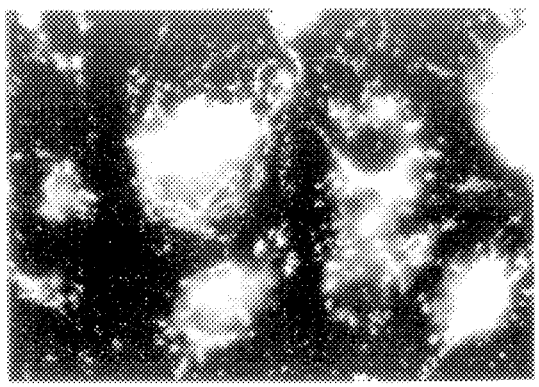

Trophinin is expressed on the surfaces of HT-H and SNG-M cells in a unique lace-like pattern (FIGS. 9A and 9B). This expression indicates that trophinin proteins cluster to form patches in the plasma membrane. Trophinin contains decapeptide repeats that form multiple B-turn structures (see FIG. 5A and SB). This unique structure can be responsible for self-aggregation of trophinin in the cell membrane and for mediating cell adhesion. The subcellular localization of tastin in HT-H and SNG-M cells (FIGS. 9C and 9D) indicates that tastin can associate with cytoskeletal elements such as cytokeratins present in these cells. Thus, trophinin-assisting protein's can function to segregate trophinin molecules into clusters on the apical plasma membrane membranes by interacting with trophinin in cells.

Evidence from recent studies on cell adhesion molecules indicates that their function is regulated by association with cytoplasmic proteins and cytoskeletal structures (Gumbiner, Neuron 11:551–564 (1993); Stappert and Kemler, Curr. Opin. Neurol. 3:60–66 (1993); Garrod, Curr. Opin. Cell Biol. 5:30–40 (1993; Hynes, Cell 69:11–25 (1992)). Such molecular organization is important for cell-to-cell adhesion and cell movement. Cytoplasmic proteins involved in regulating cell adhesion molecules are associated with kinases that play a role in signal transduction, which occurs upon binding of cell adhesion molecules at the cell surface. Both trophinin and tastin contain serine and threonine residues that can serve as potential phosphorylation sites for protein kinases. For example, the amino terminal region of trophinin contains three serine and threonine residues that are potential phosphorylation sites (FIG. 3). The presence of phosphorylation sites in trophinin and trophinin-assisting proteins indicates that the adhesion of trophinins expressed on one cell to those on another cell can be involved in triggering phosphorylation of trophinin and trophinin-assisting proteins as a signal to initiate the morphological changes occurring subsequent to trophinin-mediated cell adhesion.

The invention provides methods to modify the ability of cells to adhere to each other. Cell adhesion can allow the cells to undergo subsequent physiological changes associated with cell adhesion. Such physiological changes can result from an increase in the adherence between cells due to increasing the level of trophinin expressed on the cell surface. An increase in adherence can be achieved by introducing an exogenous nucleic acid molecule encoding trophinin into cells and allowing the cells to adhere under appropriate conditions (see Example VII). This method of increasing adherence between cells can be used with any cell that can express functional trophinin proteins. Such cells include, for example, cells obtained from human or non-human primates or other mammalian cells, such as bovine, ovine, porcine or murine cells.

A nucleic acid molecule encoding trophinin can be introduced into a population of first cell types, which can be allowed to adhere to each other. In addition, a cell from the population of first cell types, which contain a nucleic acid molecule encoding trophinin, can be combined with a second cell type, wherein a DNA molecule encoding a trophinin binding protein has been introduced into the second cell type. In this case, adhesion between the first cell type and the second cell type can occur due to binding of trophinin on one cell to the trophinin binding protein of the other cell. Similarly, a third or additional cell types expressing trophinin or a trophinin binding protein can be included so as to provide adhesion among three or more cell types. As used herein, the term "trophinin binding protein" means a molecule that can bind to trophinin with an affinity of about $1 \times 10^{-5}$M or greater as measured, for example, by ELISA. A trophinin binding protein can include, for example, trophinin itself, an anti-trophinin antibody or a trophinin-assisting protein.

Cell types that naturally express trophinin can adhere to a cell type that has been modified to express trophinin (see Example VII). In some cases, the expression of trophinin alone in cells may not enable cell adhesion. In such cases, adhesion may require the expression of a trophinin-assisting protein in addition to trophinin. The present invention also provides nucleic acid molecules encoding members of the trophinin-assisting protein family of proteins as well as methods for introducing such exogenous nucleic acid molecules into cells to obtain expression of a trophinin-assisting protein. This method of increasing adherence between cells by introducing an exogenous nucleic acid molecule can be used with any cell that can express functional trophinin-assisting proteins. Such cells include, for example, human and non-human primates or other mammalian cells, as described above.

The level of expression of trophinin in a cell can be increased on the cell surface by contacting the cell with a trophinin agonist. As used herein, "trophinin agonist" means a chemical or biological molecule such as a simple or complex organic molecule, a peptide, peptidomimetic, protein, carbohydrate or nucleotide sequence that can increase the expression level of functional trophinin in a cell and, thereby, increase the capacity of the cell for trophinin-mediated cell adhesion. A nucleic acid encoding trophinin is an example of a trophinin agonist. An expression vector that contains an exogenous nucleic acid molecule encoding trophinin can also be used as a trophinin agonist. For example, the introduction of an expression vector encoding trophinin into a cell can result in increased expression of trophinin and increased ability of the cell to undergo trophinin-mediated cell adhesion. Another example of a trophinin agonist can be a trophinin-assisting protein or an expression vector that contains an exogenous nucleic acid molecule encoding a trophinin-assisting protein. For example, a cell that can express trophinin but cannot efficiently mediate cell adhesion can be due to the inability of the cell to express a level of trophinin-assisting protein sufficient to interact with trophinin or a trophinin binding protein. In such cells, a trophinin agonist can, for example, be a trophinin-assisting protein or an expression vector encoding a trophinin-assisting protein.

Particular types of trophinin agonists also can include hormones, cytokines or other types of molecules that interact directly or indirectly, for example, with genetic regulatory elements that control the expression level of trophinin or a trophinin-assisting protein. Genetic regulatory elements include, for example, promoters, enhancers, or intronic sequences that can regulate protein expression at the transcriptional or translational level. For example, a trophinin agonist can increase the expression of trophinin in a cell by binding to the promoter region of a trophinin gene and increase the efficiency of transcription. A trophinin agonist also can increase the expression of trophinin indirectly by binding to a regulatory protein, which, in turn, can activate an enhancer sequence to increase transcription of the trophinin gene.

Trophinin mediated cell adhesion also can be increased by directly contacting a cell with purified trophinin. The ability of cells to adsorb a protein such as trophinin by an active or a passive process can result in a greater level of trophinin available on the cell surface for contact with another cell, thus, increasing the likelihood of trophinin-mediated cell adhesion.

Trophinin agonists, which are useful for increasing trophinin-mediated cell adherence, are useful, for example, for preventing or minimizing the likelihood of implantation failure. Humans or other mammals that exhibit implantation failure can be tested for the level of trophinin or a trophinin-assisting protein expressed by endometrial cells using the methods described herein. Subjects having cells that fail to express sufficient levels of trophinin or trophinin-assisting proteins to achieve trophinin-mediated adhesion or express an aberrant or non-functional form of trophinin or a trophinin-assisting protein can be identified and a trophinin agonist can be used to achieve cell adhesion.

The invention also provides methods to reduce or inhibit trophinin-mediated cell adhesion by contacting a cell with a trophinin antagonist, which can reduce or inhibit trophinin binding. Such methods can be used with human or other mammalian cells that express trophinin. For example, methods to reduce or inhibit trophinin-mediated cell adhesion can be used to block or terminate embryo implantation in humans or other mammals. As used herein, "trophinin antagonist" means a chemical or biological molecule such as a simple or complex organic molecule, a peptide, peptidomimetic, protein, carbohydrate, antibody or nucleotide sequence that can reduce or inhibit the ability of trophinin to mediate cell adhesion.

A trophinin antagonist can act by binding to a trophinin molecule of a first cell and, as a result of such binding, inhibit binding to a trophinin molecule on a second cell. Thus, the binding between two trophinin molecules is reduced or inhibited by the trophinin antagonist to a level below that required for a biological activity. An antibody molecule that binds to portion of trophinin exposed on the external side of the cell membrane is an example of a trophinin antagonist. The present invention provides methods to produce such antibodies (see Example V) and to evaluate such antibodies for their ability to act as trophinin antagonists in an in vitro cell binding assay (see FIG. 1D and Example VII).

An active fragment trophinin antagonist is another example of a trophinin antagonist that can bind to trophinin on a cell and prevent the cell from binding to a second cell that expresses a trophinin binding protein. As used herein, an "active fragment trophinin antagonist" means a portion of trophinin or a trophinin binding protein that cannot mediate cell adhesion but that can bind to a trophinin molecule. Such active fragment trophinin antagonists can be peptides as small as about five amino acids and can be identified, for example, by screening a peptide library (see for example, Ladner et. al., U.S. Pat. No: 5,223,409, Jun. 29, 1993, which is incorporated herein by reference) to identify peptides that bind to trophinin but do not mediate cell adhesion.

A trophinin antagonist also can interfere with the interaction of a trophinin-assisting protein with trophinin. Thus, a chemical or biological molecule such as a simple or complex organic molecule, a peptide, peptidomimetic, protein, carbohydrate or nucleotide can be a trophinin antagonist by binding to the site on a trophinin-assisting protein or on a trophinin molecule that is involved in the interaction between a trophinin-assisting protein and trophinin.

A trophinin antagonist need not bind directly to the site in trophinin that binds to another trophinin molecule or the site in trophinin that binds to a trophinin-assisting protein, in order to inhibit cell adhesion. Thus, for example, a trophinin antagonist of sufficient size, when bound to a region in trophinin that is near the trophinin binding site can physically block another trophinin molecule from binding to the site. Also, a trophinin antagonist can bind to trophinin and change the structure of the trophinin binding site rendering it unsuitable for adhesion to another trophinin molecule. Thus, a trophinin antagonist can act like an allosteric inhibitor of an enzyme. A trophinin antagonist can also function to inhibit trophinin-mediated cell adhesion by binding to a trophinin-assisting protein in a cell, thereby inhibiting the ability of the trophinin-assisting protein to assist trophinin in mediating cell adhesion.

A trophinin antagonist also can function by reducing the level of expression of trophinin or a trophinin-assisting protein, thereby reducing or inhibiting cell adhesion. For example, nucleic acid molecules encoding an antisense nucleotide sequence or encoding a ribozyme for a trophinin or a trophinin-assisting protein can be incorporated into vectors and introduced into cells by methods well known to those in the art as described above. The level of trophinin or trophinin-assisting protein expression also can be reduced by treating cells with hormones, cytokines or other type molecules that interact directly or indirectly with genetic regulatory elements controlling the expression level of trophinin or a trophinin-assisting protein in a cell. A trophinin antagonist can effect trophinin-mediated cell adhesion by reducing the level of expression of trophinin in the cell by blocking regulatory elements involved in maintaining expression of trophinin. A trophinin antagonist can also reduce the level of trophinin expression by acting directly or indirectly as a negative regulator.

Reducing or inhibiting adhesion of cells by trophinin-mediated cell adhesion can be useful in vitro or in vivo. In vitro, trophinin antagonists can be identified and compared to each other to determine potency, which can be derived from concentration versus activity curves and can be represented as the concentration of antagonist that achieves 50% inhibition of activity. In vitro potency can be one criterion for selecting trophinin antagonists that can be useful in vivo. The in vitro method for measuring potency is based on the adhesion assay used to discover trophinin and trophinin-assisting protein molecules (see FIG. 1C and Example I). In this method, a radiolabeled cell line expressing trophinin and a trophinin-assisting protein (e.g. HT-H cells) is contacted with the antagonist to be tested, then the mixture is added to a paraformaldehyde fixed-monolayer of trophinin and trophinin-assisting protein expressing cells (e.g. SNG-M cells). After a period of time, the unbound cells are removed by washing and the percentage of attached cells determined by counting the bound radioactivity. A potent trophinin antagonist can be identified by its ability to significantly reduce or to inhibit trophinin-mediated cell adhesion.

The ability of trophinin to mediate cell adhesion can have other in vitro uses besides that of a trophinin antagonist. For example, trophinin can be used to bind trophinin- expressing cells to a solid support, which is useful, for example, to purify a population of trophinin expressing cells from a mixed population containing trophinin expressing and non-trophinin expressing cells or to purify a trophinin expressing embryo. Also, trophinin attached to a prosthetic devise can be used to bind a layer of trophinin expressing cells to the devise to render the devise more suitable for introduction in vivo.

Trophinin can be bound to a solid support using methods known in the art (for example see Harlow and Lane, supra, (1988)). For example, purified trophinin in PBS (phosphate buffer saline, 10 mM phosphate buffer, pH 7.4) can be directly adsorbed to a plastic tissue culture surface, a polyvinyl chloride surface or a nitrocellulose surface. Trophinin also can be covalently coupled to beads such as, for example, agarose or polyacrylamide that had been previously activated by a coupling agent such as glutaraldehyde or cyanogen bromide. In addition, trophinin can be attached indirectly to a solid support, for example, by first coating or coupling an agent that can specifically bind to trophinin.

A population of trophinin-expressing cells can be enriched from a mixed population of trophinin-expressing and cells that do not express trophinin by applying the mixed cell population to a solid support or surface containing trophinin. After a period of time sufficient to allow the trophinin-expressing cells to adhere to the solid support, cells that do not express trophinin can be washed from the support. The enriched population of trophinin expressing cells can be used directly on the solid support or can be removed from the solid support by vigorous washing or by treating the cells with a trophinin antagonist.

A trophinin antagonist or agonist can be used to prepare a medicament for the treatment of a condition such as infertility, for treatment of a disease or for intervening in a potential pregnancy. For example, a trophinin antagonist can be administered to a subject to block embryo implantation following fertilization by inhibiting binding of the embryo trophoblast cell layer to the uterine epithelial cell layer. A trophinin antagonist also can be used to terminate implantation after it has already occurred by administering a trophinin antagonist to effect detachment of the embryo from the uterine cell lining. In contrast, a trophinin agonist can be administered to a subject to alleviate implantation failure by enhancing the binding between the trophoblast cell layer of the embryo and the endothelial cell layer of the uterus. Trophinin antagonists and agonists of the invention are particularly useful when administered as a pharmaceutical composition containing the trophinin antagonist or agonist and a pharmaceutically acceptable carrier. Pharmaceutically acceptable carriers are well known in the art and include, for example, aqueous solutions such as physiologically buffered saline or other solvents or vehicles such as glycols, glycerol, oils such as olive oil or injectable organic esters.

A pharmaceutically acceptable carrier can contain physiologically acceptable compounds that act, for example, to stabilize or to increase the absorption of a trophinin antagonist or agonist. Such physiologically acceptable compounds include, for example, carbohydrates, such as glucose, sucrose or dextrans, antioxidants, such as ascorbic acid or glutathione, chelating agents, low molecular weight proteins or other stabilizers or excipients. One skilled in the art would know that the choice of a pharmaceutically acceptable carrier, including a physiologically acceptable compound, depends, for example, on the route of administration of the composition.

One skilled in the art would know that a pharmaceutical composition containing a trophinin antagonist or agonist can be administered to a subject by various routes including, for example, by intrauterine instillation, orally or parenterally, such as intravenously, intramuscularly, subcutaneously or intraperitoneally. The composition can be administered by injection or by intubation. The pharmaceutical composition also can be incorporated, if desired, into liposomes or microspheres or can be microencapsulated in other polymer matrices (Gregoriadis, *Liposome Technology*, Vol. 1 (CRC Press, Boca Raton, Fla. 1984), which is incorporated herein by reference). Liposomes, for example, which consist of phospholipids or other lipids, are nontoxic, physiologically acceptable and metabolizable carriers that are relatively easy to make and administer.

In order to inhibit embryo implantation, the trophinin antagonist is administered in an effective amount, which is about 0.01 to 100 mg/kg body weight. As used herein, the term "effective amount" means the amount of trophinin antagonist that can effectively block a cell adhesion event. For example in the case of implantation, an effective amount is that which blocks embryo implantation. In the case of a trophinin agonist, the "effective amount" means the amount of agonist that can effectively increase level of trophinin-mediated cell adhesion. For example, in implantation failure, an effective amount of a trophinin agonist is the amount that allows for successful implantation. An effective amount of a trophinin antagonist or agonist in a subject can be determined using methods known to those in the art.

The total effective amount can be administered to a subject as a single dose, either as a bolus or by infusion over a relatively short period of time, or can be administered using a fractionated treatment protocol, in which the multiple doses are administered over a more prolonged period of time. One skilled in the art would know that the concentration of trophinin antagonist or agonist required to obtain an effective dose in a subject depends on many factors including the age and general health of the subject as well as the route of administration and the number of treatments to be administered and the chemical form of the antagonist or agonist. In view of these factors, the skilled artisan would adjust the particular amount so as to obtain an effective amount for the subject being treated.

The cadherin and integrin families of adhesion molecules, which are involved in cell-cell and cell-matrix adhesion, are implicated in epithelial differentiation, carcinogenesis and metastasis. A further understanding of how such adhesion receptors exert their biological effects on the cell was accomplished through the discovery of a cell adhesion regulator gene (Pullman and Bodmer, *Nature* 356:529–533 (1992)). The cell adhesion regulator gene codes for a protein that is located in the cytoplasm and functions as a signal transduction molecule for integrin adhesion receptors. The cell adhesion receptor gene has the characteristics of a tumor suppressor gene because inactivation of the gene can result in loss of differentiation induction of a cell and subsequent acquisition of invasive and metastatic character. The genes encoding the trophinin-assisting proteins of the present invention also can function as tumor suppressor genes. For example, the structural features of the trophinin-assisting proteins, as derived from the deduced amino acid sequences (see SEQ ID NO: 5, SEQ ID NO: 7 and SEQ ID NO: 9), are consistent with a cytoplasmic regulatory protein that can mediate intracellular signalling of trophinin or other cell adhesion molecules.

The present invention provides methods to increase the level of expression of trophinin-assisting proteins, thus increasing the tumor suppressor activity of a cell. Such methods can, for example, be useful for the treatment of cancer. As used herein, a trophinin-assisting protein agonist means a chemical or biological molecule such as a simple or complex organic molecule, a peptide, peptido-mimetic, protein, carbohydrate or nucleotide sequence that can increase the expression level of a trophinin-assisting protein in a cell. Particular types of trophinin-assisting protein agonists can include hormones, cytokines or other types of molecules that interact either directly or indirectly with genetic regulatory elements controlling the expression level of a trophinin-assisting protein.

The following examples are intended to illustrate but not limit the present invention.

EXAMPLE I

Cell Culture Adhesion Method

This example describes methods for performing cell adhesion assays and for evaluating their specificity and impact on cell morphology.

A. Cell Lines

The human teratocarcinoma cell line HT-H was used as a source of embryonic trophoblast cells for the adhesion assay.

HT-H cells (Izhar et al., *Biol.* 116:510–518 (1986), which is incorporated herein by reference) were maintained in RPMI 1640 medium containing 10% fetal bovine serum, 2 mM glutamine, 100 units/ml penicillin and 100 µg/ml streptomycin. Trophoblastic HT-H cells were separated from undifferentiated HT-H cells as described (Izhar et al., supra, 1986) and subcloned for use in the experiments described. The endometrial adenocarcinoma cell line SNG-M (Ishiwata et al., *Cancer Res.* 37:1777–1785 (1977), which is incorporated herein by reference) was maintained in RPMI medium as described above. Endometrial adenocarcinoma cell lines Hec1A, RL95-2 AN3CA and KLE were obtained from American Type Culture Collection (Rockville Md.) and were cultured in Dulbecco's modified Eagle's (DME) medium containing 10% fetal bovine serum, 2 mM glutamine, 100 units/ml penicillin and 10 µg/ml streptomycin. Additional epithelial cells which were tested included COS-1 cells (monkey kidney), HeLa (uterine cervical carcinoma), HepG2 (hepatocellular carcinoma), SW480 (colonic adenocarcinoma), and A431 (epidermoid carcinoma). These cells were obtained from the American Type Culture Collection and were cultured as described above.

B. Cell Adhesion Assay

The adhesion of HT-H cells to several different human endometrial epithelial cells was examined. HT-H cells were metabolically labeled with $^{35}$S-methionine using Trans-label (DuPont/NEN, Boston Mass.) in methionine- and cysteine-free RPMI medium supplemented with 10% dialyzed fetal bovine serum, 2 mM glutamine, 100 µg/ml pyruvate, 100 units/ml penicillin and 100 µg/ml streptomycin. Cells were labeled at 37° C. in a humidified $CO_2$ incubator. After 20 minutes (min), the medium was replaced with complete medium and cells were incubated an additional 2 hr.

The $^{35}$S-labeled HT-H cells were detached from the tissue culture dish using cell dissociation solution (Specialty Media, Lavalette, N.J.) supplemented with 1 mM EDTA. The cells were pelleted by centrifugation and resuspended in Hank's balanced salt solution (HBS). Cell suspensions (0.2 ml, $5\times10^4$ cells) were added to a monolayer of endometrial epithelial cells grown in a 24 well tissue culture plate. HT-H cells that did not adhere to the monolayer were removed by washing 3× with HBS with or without 1 mM EDTA. The cells remaining in each well were solubilized with 0.5 ml of 0.5N NaOH and 1% SDS. The lysate was transferred to a scintillation vial and radioactivity was counted. The data were expressed as % radioactivity remaining on the monolayer relative to the total radioactivity of $^{35}$S-labeled HT-H cells added. The results were obtained from triplicate cultures.

The results of the cell adhesion assays indicate that HT-H cells attached to the SNG-M, Hec1A, KLE and RL95-2 cells, but attached minimally to the AN3CA cells (Table 1). The addition of 1 mM EDTA did not change significantly the percentage of HT-H cells which bound to SNG-M, Hec1A and KLE cells (Table 1), whereas, the attachment of HT-H cells to RF95-2 cells was reduced significantly in the presence of EDTA. These results indicate that adhesion of HT-H cells with SNG-M, Hec1A or KLE cells is divalent cation independent. In contrast, HT-H adhesion to RL95-2 cells is largely divalent cation dependent since a relatively large number of cells failed to ad here after washing with EDTA (T able 1) . Since a relatively high proportion of HT-H cells adhered to SNG-M cells and that adherence was not cation dependent, these cells were chosen for further study.

TABLE I

ADHESION OF HT-H CELL TO ENDOMETRIAL ADENOCARCINOMA CELLS

| -Cell Line# | Percentage HT-H cells attached | |
|---|---|---|
| | +EDTA | −EDTA |
| SNG-M | 56.9 ± 8.2 | 49.7 ± 7.3 |
| Hec1A | 29.6 ± 10.2 | 24.2 ± 8.3 |
| KLE | 32.5 ± 8.5 | 27.2 ± 4.8 |
| RL95 | 83.5 ± 9.7 | 20.4 ± 12.1 |
| AN3CA | 4.2 ± 0.8 | 2.1 ± 0.6 |

Used as a monolayer without fixation.

Cell adhesion assays also were conducted using fixed cell monolayers. In this case, cells grown in 24 well tissue culture plates were treated with 1% paraformaldehyde in PBS for 15 min at RT. The fixed cells were washed in PBS and were used for cell adhesion assays as described above. The results showed that HT-H cells adhered efficiently to the surface of paraformaldehyde-fixed monolayer of SNG-M cells in a divalent cation independent manner (FIG. 1A). Furthermore, when SNG-M cells were added to a fixed monolayer of SNG-M cells, they adhered efficiently in a divalent cation independent manner (FIG. 1A).

COS-1 cells adhered minimally to SNG-M cells (FIG. 1A), whereas HeLa, HepG2, SW480 and A431 did not detectably adhere (not shown). Essentially the same results were obtained when fixed HT-H cell monolayers were used in place of SNG-M cell monolayers (FIG. 1B). In summary, adhesion between HT-H and SNG-M cells is cell type specific and divalent cation independent.

C. Morphological Evaluation of Adherent Cells

Electron microscopy was used to characterize the adherent interface formed during the co-culture of HT-H and SNG-M cells. SNG-M cells were grown in a Falcon 3001 (25×10 mm) tissue culture dish until reaching 50% confluency. HT-H cells were detached from the tissue culture dish by trypsin/EDTA treatment and were added to monolayers of SNG-M cells. The combined cells were cultured for up to 4 days. At various times, individual cultures were processed for transmission electron microscopy. Cells were fixed in freshly prepared fixative (10 mM NaIO4, 75 mM lysine, 37.5 mM sodium phosphate buffer, 2% paraformaldehyde, pH 6.2) for 15 min at RT. Cells then were washed with phosphate buffer, treated with glutaraldehyde and processed for electron microscopy as described previously (Klier et al., *Devel. Biol.* 57:440–449 (1977), which is incorporated herein by reference). Electron microscopy was performed using a Hitachi K-600 electron microscope.

Following 10 min co-culture, the apical surface of HT-H cells faced the apical surface of SNG-M cells (FIG. 2A) and many microvilli were present between the cells (FIG. 2B). After 6 hr, there were closer adhesive interactions between the cells (FIG. 2C), with the edges of the microvilli extending from one cell type and attaching to the cell surface of the other cell type (FIG. 2C). Occasional invagination in the plasma membrane of the SNG-M cells was observed (shown by an arrow in FIG. 2C). After 4 days, the microvilli had disappeared completely from the surfaces of both cell types and desmosome-like adherent junctions were present between the cell (FIG. 2D).

The results described using the in vitro cell adhesion assay are similar to the morphological studies of human implantation in vivo and in vitro (Lindenberg et al., *Hum. Reprod.* 1:533–538 (1986); Knoth and Larsen, *Acta Obstet. Gynecol. Scand.* 51:385–393 (1972)). For example, during implantation, the trophoblast endometrial epithelial cells show characteristics which include: 1) reduction of microvilli in areas of attachment, 2) an invagination response of endometrial cells at the contact site, 3) formation of a junction complex or sign of focal adhesions between the trophoblast and endometrial cells in a later stage of implantation and 4) intrusion of the trophoblast between the endometrial epithelia. Thus, the HT-H and SNG-M cells provided are a useful in vitro model of embryo implantation.

EXAMPLE II

Expression Cloning of Molecules Mediating Adhesion of HT-H Cells to SNG-M Cells

This example describes a method to clone cDNA molecules that are involved in mediating cell adhesion.

A. Expression of a cDNA Library in COS-1 Cells

A functional cDNA expression cloning strategy was used to obtain the nucleic acid molecules encoding the proteins responsible for the initial, EDTA independent cell adhesion between HT-H and SNG-M cells (Aruffo and Seed, *Proc. Natl. Acad. Sci. (USA)* 84:8573–8577 (1987), which is incorporated herein by reference). COS-1 cells, which did not adhere efficiently to monolayers of SNG-M cells (see FIG. 1A), were chosen for transfection with a cDNA library derived from HT-H cells (obtained from Invitrogen Corp. Ltd; San Diego, Calif.) Poly-A mRNA prepared from freshly harvested HT-H cells was used t construct a unidirectional cDNA expression library in the mammalian expression vector pcDNAI. The cDNA library consisted of $2 \times 10^6$ independent clones with an insert size ranging from 0.5 to 3.0 kb.

COS-1 cells ($1 \times 10^8$ cells) were transfected with the HT-H cDNA library using electroporation. This method of transfection was used be cause the diethylaminoethyl-dextran and lipofection reagents used for other transfection methods increased the nonspecific adhesion of COS-1 cells to the SNG-M cells. COS-1 cells were grown in Falcon culture dishes until the cells reached about 75% confluency, were detached using 0.1% trypsin and 1 mM EDTA and suspended in DME medium containing 10% fetal bovine serum. The cells were pelleted by centrifugation, washed 2x with cold PBS and $1-0.5 \times 10^7$ cells/ml were suspended in PBS containing 100 µg/ml plasmid DNA. Electroporation was performed using a Gene Pulser (Biorad, Hercules, Calif.) at 0.4 kvolt with a capacitance of 125 µF. The transfected cells were cultured for 48 hr in DME medium containing 10% fetal bovine serum, 2 mM glutamine, 100 units/ml penicillin and 100 µg/ml streptomycin.

B. Screening the cDNA Expression Library by Cell Adhesion

The transfected COS-1 cells were selected for binding to an SNG-M cell monolayer. The SNG-M cells were cultured to confluency in a Falcon 3001 or 3005 tissue culture dish, then fixed with 1% paraformaldehyde in PBS at RT for 15 min. The fixed SNG-M cells were washed 3x with PBS and 1x with HBS.

Two days following electroporation, transfected COS-1 cells were detached from the tissue culture plate by incubating for 5–10 min with cell dissociation solution (Specialty Media, Lavalette, N.J.) supplemented with 1 mM EDTA. The cells were suspended in HBS containing 1 mM EDTA and were added to a fixed SNG-M cell monolayer and allowed to attach at RT for 20 min. The plate was washed 3x with HBS containing 1 mM EDTA and transfected COS-1 cells that remained on the SNG-M cell monolayer were mechanically detached by flushing HBS with a pasteur pipet. Approximately $1 \times 10^4$ COS-1 cells were recovered and added to a second SNG-M monolayer to adhere as described above. After 20 min, the nonadherent COS-1 cells were discarded by washing as above and the adherent cells (representing about $1 \times 10^3$ COS-1 cells) were solubilized with 1% SDS. Plasmid DNA was recovered from the SDS soluble extract and amplified in *E. coli* MC1061/P3 cells.

The plasmid DNA obtained from the transfected COS-1 cells was subjected to a second round of electroporation in COS-1 cells followed by selection by adhesion as described above, except that the number of cells used for transfection was reduced to $1 \times 10^8$ to $1 \times 10^7$ cells. After the first adhesion selection step, about $2 \times 10^3$ transfected COS-1 cells were attached to the SNG-M monolayer. After the second cell adhesion step, plasmid DNA was obtained by extraction with SDS as described above.

*E. coli* MC1061/P3 cells were transformed using plasmid DNA following the second transfection. Plasmid DNA from two hundred *E. coli* clones was divided into ten groups containing 20 plasmids each. Fresh COS-1 cells were transfected with each group containing the mixture of 20 clones and allowed to adhere to a monolayer of the SNG-M cells. The individual clones derived from a group that was positive for adhesion were each transfected into COS-1 cells and tested for adhesion. However, the transfected COS-1 cells derived from individual clones failed to adhere to the SNG-M cells. The 20 clones were screened again using a series of mixtures containing a decreasing number of clones. A mixture of two specific cDNA sequences were the minimum required to enable transfected COS-1 cells to adhere to SNG-M cells. The initial pair of cDNA clones identified were trophinin and tastin. The results in FIG. 1C demonstrate that COS-1 cells transfected with a mixture of trophinin and tastin cDNA adhered to a monolayer of SNG-M cells, while COS-1 cells transfected only with trophinin cDNA or tastin cDNA failed to adhere. Further screening of the remaining 200 clones for co-transfection with the trophinin clone identified two other clones which were required for adhesion. The additional two clones were named bystin and lastin.

The trophinin cDNA clone encodes an intrinsic membrane protein, while the tastin, bystin and lastin clones likely encode a cytoplasmic protein. The cDNA clones were sequenced by the dideoxy nucleotide chain termination method of Sanger et al. (*Proc. Natl. Acad. Sci. (USA)*, 74:5463–5467 (1977), which is incorporated herein by reference) using a modified T7 DNA polynuclease ("SEQUENASE", United States Biochemicals, Cleveland, Ohio). The nucleotide sequence of the trophinin cDNA was determined from restriction fragments subcloned into Bluescript from nested deletion mutants generated by exonuclease III (Boehringer Mannheim, Indianapolis, Ind.). The nucleotide sequence of the tastin, bystin and lastin cDNA were determined using oligonucleotide primers. Editing and analysis of the sequence was done using DNASIS (Hitachi, Tokyo, Japan) and PCgene software (Intelligenetics, Mountain View, Calif.). Sequence comparisons with the databases were performed using the "blast" network program (National Center for Biotechnology Information, NIH). The complete nucleotide sequence for trophinin cDNA is shown in FIG. 3 (SEQ ID NO: 1), while the complete nucleotide sequence of tastin and bystin and a partial nucleotide sequence of lastin are shown in FIG. 6 (SEQ ID NO: 4), FIG. 7 (SEQ ID NO: 6) and FIG. 8 (SEQ ID NO: 8), respectively. The clone which contained the lastin sequence was missing the 5' end of the gene including the poly-A tail of the mRNA.

EXAMPLE III

Characterization of Trophinin

The complete cDNA sequence and the deduced amino acid sequence of trophinin are shown in FIG. 3. The trophinin cDNA clone covers 2524 nucleotides with an open reading frame encoding 749 amino acids. The 3' untranslated region consists of 250 nucleotides and contains a polyadenylation signal 12 bp upstream of the poly-A tail. An optimal translation initiation sequence (Kozak, supra, 1984) is associated with only one of the ATG codons in the near 5' region. Use of this ATG for translation initiation would result in a predicted molecular mass of 69.29 kDa for trophinin.

The plasmid cDNA clones were subjected to in vitro translation using T7 oligonucleotide primer, rabbit reticulocyte lysate (Promega, Madison, Wis.), RNA polymerase and $^{35}$S-methionine. The products were processed by SDS-PAGE and visualized by autoradiography. In vitro translation of trophinin cDNA showed a major product at 61 kDa (FIG. 4), which is in agreement with the predicted molecular mass of 69.29 kDa.

Hydropathy analysis (Kyte and Doolittle, supra, 1982) of trophinin defines this molecule as an intrinsic membrane protein having 8 separate transmembrane domains (FIG. 5A). No cleavable signal sequence was found in the cDNA clone coding for trophinin, however, the first putative membrane spanning domain (amino acids 66 to 120) follows an arginine residue at position 54 that can function as a stop transfer signal during translocation into the endoplasmic reticulum. Employment of the stop transfer sequence during translocation can result in the amino terminal segment of trophinin from the methionine at position 1 to the serine at position 65 being located in the cytoplasm. The location of the amino terminal portion of trophinin was examined using antibodies raised against a peptide within the predicted cytoplasmic tail of the trophinin (residues 23 to 31). In these experiments, the antibodies only reacted with HT-H cells that had their cell membranes removed by detergent treatment, indicating that the amino terminal portion of trophinin is located in the cytoplasm.

The amino terminal region of trophinin contains three serine and/or threonine residues that can function as potential phosphorylation sites (see FIG. 3). The threonine at position 7 is contained within a consensus site for phosphorylation by casein kinase II (Kemp and Pearson, supra, 1990). The serine residues at position 46 and 52 are located within consensus sequence sites for protein kinase C phosphorylation. The serine residue at position 46 also is contained within a consensus sequence site for cAMP/cGMP dependent phosphorylation. The presence of phosphorylation sites in a transmembrane protein such as trophinin indicates a likely mechanism for signalling the morphological changes in cells that are known to occur subsequent to trophinin-mediated adhesion (see FIG. 2A, 2B, 2C and 2D).

Trophinin contains eight potential membrane spanning regions (FIG. 5A). The relative proportion of trophinin localized in the cytoplasm, in the membrane bilayer and on the cell surface is 10%, 56% and 34%, respectively. Four potential N-glycosylation sites, and thirteen potential 0-glycosylation sites, are found within the predicted cell surface domains of trophinin (FIG. 3).

Greater than 90% of trophinin is contains a tandemly repeated decapeptide motif (FIG. 5B; SEQ ID NO. 3). There are 69 such repeat sequences and they exhibit some variation in sequence and length. The predicted exposed cell surface domains of trophinin contain regions of decapeptide repeats that are hydrophilic in character. Three such exposed domains can be identified in trophinin, at amino acid positions 278 to 364 (SEQ ID NO: 20), 441 to 512 (SEQ ID NO: 21) and 634 to 719 (SEQ ID NO: 22) (see FIG. 3; bold lettering).

Protein secondary structure algorithms (Garnier et al., supra, 1978; Gascuel and Golmard, supra, 1988), predict that the decapeptide repeats conform to a repeated 13-turn structure that can be a key structural element for efficient homophilic adhesion (not shown). Four potential N-glycosylation sites, N-X-S(T), and thirteen potential O-glycosylation sites, P-S(T) or S(T)-P, are found within the predicted cell surface domains of trophinin (FIG. 3). Trophinin has no significant homology to sequences in protein and nucleic acid databases.

EXAMPLE IV

Characterization of Trophinin-Assisting Proteins

The complete nucleotide sequence of the tastin cDNA clone (SEQ ID NO: 4) and the deduced amino acid sequence (SEQ ID NO: 5) are shown in FIG. 6. The tastin cDNA clone contains 2,577 nucleotides with an open reading frame encoding 778 amino acids. The 3' untranslated region contains 128 nucleotides and has a polyadenylation signal 11 bp upstream of the poly-A tail. The nucleotide sequence around the ATG at position 11 is contained within a consensus sequence for a translation initiation site (Kozak, supra, 1984). In vitro translation of the tastin cDNA produce a predominant product of 80 kDa (FIG. 4), consistent with the predicted molecular weight 83.75 kDa based on the cDNA open reading frame. Tastin is likely a cytoplasmic protein since it lacks an obvious secretory signal sequence and transmembrane helices as defined by hydropathy analysis (Kyte and Doolittle, supra, 1982), and shows a pattern of cell staining similar to other cytoplasmic proteins (see FIG. 9C and 9D).

Tastin is rich in prolines, which account for 15.3% of the total amino acids of the protein. In addition, the region from residues 516 to 650 is cysteine rich (see italics in FIG. 6), with the majority of the cysteines located within four tandem repeat sequences of 33 amino acids each (not shown). Tastin also contains many serine and threonine residues and a tyrosine residue that, when considered with their adjacent amino acid residues, provide sequence motifs for protein kinase phosphorylation (FIG. 6). Specifically, tastin contains two cAMP/cGMP-dependent phosphorylation sites located at position 234 and 350 and sixteen protein kinase C phosphorylation sites, among which the threonine at position 179 most closely matches the consensus sequence (Kemp and Pearson, supra, 1990). Tastin also contains eleven serine and threonine residues that are potential casein kinase II phosphorylation sites and two threonines at positions 177 and 363 that are within a consensus MAP kinase phosphorylation site (Gonzalez et al., supra, 1991).

Tastin has no overall significant homology to previously reported protein sequences. Nucleotide sequence homology analysis of tastin identified the sequence HFBCL29 (Genbank accession number M85643), which was derived from a human fetal brain cDNA library. HFBCL29 shows homology to a portion of tastin cDNA (positions 2340 to 2057) provided the HFBCL29 sequence represents the noncoding stand of the DNA (ie. the homology is due to nucleotide base complementarity). Thus, HFBCL29 sequence would be homologous to a portion of the tastin if the former sequence had been recorded in the data base in the antisense direction. The protein sequence deduced from HFBCL29 is believed to be related to Y box binding protein-1 (Adams et al., supra, 1992). However, the entire nucleotide sequence and deduced amino acid sequence of tastin overall are not homologous to the Y-box binding protein-1.

EXAMPLE V

Production of Antibodies to Trophinin and a Trophinin Assisting Protein (Tastin)

Peptide sequences of trophinin and tastin were analyzed to predict useful antigenic sites using the method of Hopp and Wood, *Mol. Immunol.* 20:483–489 (1983), which is incorporated herein by reference. A short sequence from the amino terminal end of trophinin and from tastin were selected as antigens. The sequences FEIEARAQE (SEQ ID NO: 10), representing residues 23 to 31 of trophinin, and DQENQDPRR (SEQ ID NO: 11), representing residues 41 to 49 of tastin, were chemically synthesized with a cysteine residue added to the amino terminus to facilitate protein conjugation. The peptides were conjugated to KLH using meta-maleimidobenzoyl N-hydroxysuccinimide ester (Sigma Chemical Co., St. Louis, Mo.) as described by Kitagawa and Aikawa (*J. Biochem.* 79:342–346 (1976)), which is incorporated herein by reference). New Zealand white rabbits were immunized the peptide-KLH conjugates according to the following procedure. On day 1, animals were injected subcutaneously with peptide conjugate emulsified in Freund's complete adjuvant. On day 14, the animals were boosted by subcutaneous injection of peptide conjugate emulsified in Freund's incomplete adjuvant. Animals were bled (30 ml) on days 24, 31 and 38 to obtain a source of antisera. Anti-peptide antibodies were purified from rabbit antisera by protein A affinity chromatography and peptide affinity chromatography as described by Richardson (*J. Virol.* 54:186–193 (1985), which is incorporated herein by reference). Rabbit antibodies to trophinin and tastin were used to detect these molecules in samples of cells and tissues (see Example VI).

To raise antibodies specific for portions of the trophinin molecule that are expressed on the external surface of the cell membrane, the three hydrophilic domains containing decapeptide repeats were separately expressed in bacteria as a fusion to glutathionine S-transferase (GST). The trophinin cDNA from the aspartic acid residue at position 278 to the serine residue at position 364 was amplified by PCR using the oligonucleotide primers GGAATTCATGGATG-GCTCTCCCAGCACTGGTG (SEQ ID NO: 14) and GCAGCTGAGTGCTGGTGCTTAGTGTACCACC (SEQ ID NO: 15) to produce the fusion protein GST551. The trophinin cDNA from the proline residue at position 441 to the serine residue at position 512 was amplified by PCR using the oligonucleotide primers GGAATTCATGCCCAG-CAACAGCATTGGC (SEQ ID NO: 16) and GCAGCT-GAGTACTGGTGCTGGGTCCATCACAAAAAC (SEQ ID NO: 17) to produce the fusion protein GST552. The trophinin cDNA from amino acid residues serine at position 634 to asparagine at position 719 was amplified by PCR using oligonucleotide primers GGAATTCATGAGCGATG-GCTTTGGCAGTAG (SEQ ID NO: 12) and CGTCGACT-CAGTTTGGTCCACCGCCGAAGCCAG (SEQ ID NO: 13) to produce the fusion protein GST553. The trophinin cDNA from the methionine residue at position 1 to the serine residue at position 66 was amplified by PCR using the oligonucleotide primers GGAATTCATGGATATCGACT-GCCTA (SEQ ID NO: 18) and GCAGCTGAGTCTG-GAGCTGGGTGCACCAT (SEQ ID NO: 19) to produce the fusion protein GST-N-terminal trophinin.

The amplified DNA fragments of the fusion proteins were ligated into pGEX-4T-1 vector (Pharmacia, Piscataway N.J.) at the EcoRI and Xho1 sites. *E. coli* HB101 was transformed with the plasmid vectors and the GST fusion proteins were produced as described by the manufacturer. The fusion proteins were initially purified by affinity chromatography on Glutathionine-agarose beads (Pharmacia).

For immunization to produce antibodies to the external domains of trophinin, GST551, GST552 and GST553 fusion proteins were electrophoresed in SDS-PAGE, the gel was stained with Coomassie blue, and the band containing the fusion protein excised from the gel. The polyacrylamide gel containing the purified fusion proteins were injected into rabbits to produce antibodies according to the procedure described previously for the synthetic peptides except that antibodies were not purified from the antiserum.

EXAMPLE VI

Detection of Trophinin and a Trophinin Assisting Protein (Tastin) in Cells and Tissues This example provides methods to identify and localize trophinin and tastin in various types of samples.

A. Localization of Trophinin and Tastin in Cultured Cells

HT-H and SNG-M cells were grown on glass coverslips in Falcon 3005 tissue culture dishes for 2–3 days. The cells were fixed at RT for 15 min with 1% paraformaldehyde in PBS, then washed 4× with PBS. Fixed cells were incubated in PBS containing 5% bovine serum albumin (IIF buffer) plus 0.1% saponin at RT for 30 min, then incubated 45 min at RT with anti-trophinin or anti-tastin antibody diluted in IIF buffer plus 0.1% saponin to permeabilize the cells. After further washing with IIF buffer plus 0.1% saphonin, cells were incubated for 30 min at RT with fluorescein isothiocyanate (FITC)-conjugated goat anti rabbit IgG F(ab')$_2$ (Cappel, Durham, N.C.) diluted in IIF buffer. Coverslips containing the cells were washed 3× with IIF buffer and 1× with PBS, then placed upside down on a slide glass in an aliquot of 95% glycerol and 5% PBS. Micrographs were obtained with a Zeiss Axioplan fluorescence microscope or a Zeiss LSM410 confocal laser scanning microscope.

Antibodies to an N-terminal peptide of trophinin (residue 23–31) showed staining of permeabilized HT-H and SNG-M cells that appears as a lace-like pattern due to clustering of the fluorescence over the cell surface (FIGS. 9A and 9B). A tangential view by confocal microscopy (not shown) showed that the majority of trophinin is detected in the upper plasma membranes of these cells. A small amount of trophinin staining is detected inside the cells and in their basal plasma membranes.

Figure 9C:
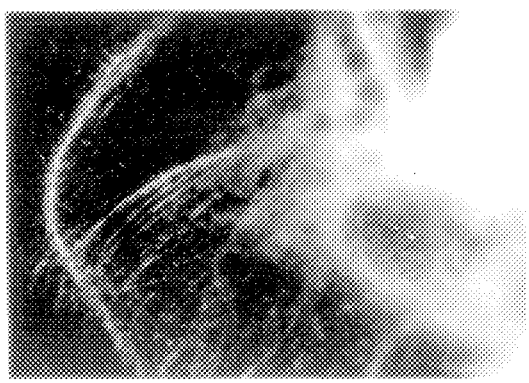
Figure 9D:
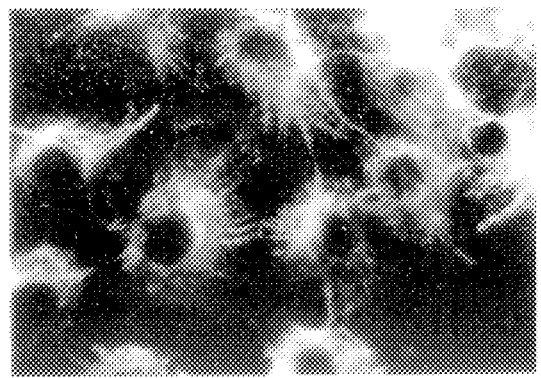

Antibody to an N-terminal peptide of tastin exhibited a diffuse staining consistent with detection of fibers in the cytoplasm of permeabilized HT-H and SNG-M (FIG. 9C and 9D). The fibers spread from the perinuclear region toward the edge of the cells indicating that tastin likely associates with the cytoskeleton in HT-H and SNG-M cells. Thus, tastin containing fibers that associate with the cytoskeleton can be involved in organizing trophinin as patches in the plasma membranes to effect efficient cell adhesion.

Antisera to GST551, GST552 and GST553, reactive with the hydrophilic domains of trophinin, were tested for staining the cell surfaces of unpermeabilized HT-H cells. For these experiments, cells were processed as for permeabilized cells except that saphonin was not used. The staining pattern observed for all three antibodies was similar to that obtained when permeabilized cells were stained by antibodies to the N-terminal domain of trophinin (residue 23–31, see FIG. 9A). Similar results were obtained using SNG-M cells as the cell targets (see FIG. 9B). These results demonstrate that all three hydrophilic domains of trophinin are exposed on the cell surface of HT-H and SNG-M cells.

COS-1 cells transfected with trophinin cDNA were also tested for staining with the antisera to the trophinin hydrophilic external domains. The cells showed a weak and diffuse staining on the surface with all three antisera. In contrast, COS-1 cells transfected with a mixture of trophinin and tastin cDNA showed stronger and more clustered staining with the antisera. These data indicate that tastin functions to create multivalent patches of trophinin on the cell surface. Such clustering of trophinin provides a basis for the observed requirement of COS-1 cells to be transfected with cDNA encoding for trophinin and a trophinin-assisted protein in order to undergo trophinin-mediated cell adhesion.

The detection of trophinin exposed on the cell surface of cultured cells was also determined using cell surface labelling and immunoprecipitation techniques. Proteins exposed on the external side of the plasma cell membrane were labelled at their cysteine residues with biotin-maleimide (Sigma). HT-H and SNG-M cells were removed from culture flasks by scraping with a rubber policeman and washed with ice-cold PBS. $1 \times 10^6$ cells were suspended in 1 ml PBS and mixed with 20 $\mu$l of dimethylformamide containing 10 $\mu$g biotin-maleimide. After 1 hr on ice, the cells were washed and resuspended in 1% NP-40 nonionic detergent to produce a soluble lysate and an insoluble material. After centrifugation to remove the NP-40 soluble lysate, the insoluble material was solubilized in 0.1% SDS essentially as described previously (Oshima et al. *Dev. Biol.* 99:447–455 (1983), which is incorporated herein by reference). The NP-40 soluble lysate was mixed with avidin-agarose beads (Sigma) for two hr at RT and the beads were centrifuged to yield an avidin-unbound fraction of the NP-40 soluble lysate. The beads were then washed and bound proteins eluted by boiling the beads for 2 minutes in SDS sample buffer (see Harlow and Lane, supra, 1988). Both bound and non-bound avidin fractions and the SDS soluble fraction were evaluated for their content of trophinin by immunoblotting with the antiserum to GST553 and with the antibodies to the N-terminal domain of trophinin (residue 23–31). Immunoblotting was performed by SDS-PAGE and nitrocellulose transfer essentially as described by Towbin et al. (*Proc. Natl. Acad. Sci. (USA)*, 76:4350–4354 (1976)) except that enhanced chemiluminescence was used for detection of immunoreactive bands (ECL kit, Amersham, Buckinghamshire, UK).

Immunoblotting of surface labelled cells showed three bands with apparent molecular masses of 90 kDa, 120 kDa and 140 kDa in HT-H cells and SNG-M cells. The majority of trophinin was detected in the avidin-bound fraction as compared to the non-bound fraction, indicating that trophinin is exposed on the external side of the cell surface. A significant amount of trophinin was insoluble in NP-40 detergent, indicating that some trophinin molecules are associated with the cytoskeleton and, therefore, that trophinin is an intrinsic plasma membrane protein.

Trophinin was evaluated by IIF to determine if the hydrophilic extracellular domains of trophinin could be used to detect trophinin expressing cells. The trophinin extracellular domain fusion proteins GST551, GST552 and GST553, the GST-N-terminal domain (residue 1–66) and GST were labelled with biotin succinamide (Sigma). SNG-M, HT-H and COS-1 cells transfected with a mixture of trophinin and tastin cDNA were grown on coverslips and processed for cell staining with the biotinylated proteins essentially as was described for the antibodies to the external domains of trophinin, except that avidin-FITC (Cappel) was used in place of a FITC-secondary antibody.

All three biotinylated trophinin extracellular domain fusion proteins stained unpermeabilized HT-H, SNG-M and the COS-1 cells transfected with trophinin and tastin cDNA. In contrast, no staining was seen when the cells were reacted with biotinylated GST or the biotinylated GST-N-terminal domain of trophinin. These results indicate that the soluble trophinin domains can bind trophinin exposed on the surface of the cells and, therefore, that the trophinin cell surface hydrophilic domains can be used to detect trophinin expressing cells.

B. Detection of Trophinin and Tastin by Northern Blotting

Total RNA was isolated from HT-H cells, SNG-M cells and COS-1 cells by the acid-guanidine:phenol:chloroform method (Chirgwin et al., *Biochem.* 18:5294–5299 (1979), which is incorporated herein by reference). Poly-A mRNA was prepared using oligo dT cellulose affinity chromatography (poly A Quick, Strategene). Five $\mu$g of poly-A RNA was electrophoresed in a 1% agarose formaldehyde gel and the RNA was transferred by blotting to nitrocellulose filter paper. The filter paper was heated at 80° C. for 2 hr to fix the RNA and was prehybridized and hybridized as described by Thomas (Thomas, *Proc. Natl. Acad. Sci. (USA)* 77:5201–5205, (1980), which is incorporated herein by reference). cDNA clones were labeled with $^{32}$P-$\alpha$-dCTP (DuPont/NEN, Boston Mass.) using a random oligo labeling kit (Boehringer-Mannheim, Indianapolis Ind.). Northern blotting was also performed using MTN-1 filters containing human tissue RNA (Clontech, Palo Alto, Calif.) prepared as described above.

A $^{32}$P-cDNA probe for trophinin detected a 3,5, 7.5 and 10 kb mRNA species from both HT-H and SNG-M cells which were not detectable from COS-1 cells (not shown). A 32P-cDNA probe for tastin detected a 3.2 and 3.3 kb mRNA species from both HT-H and SNG-M cells (not shown). The probes also detected the appropriate sized mRNA species in the poly-A mRNA from placenta, lung and liver, but at lower levels than that seen in the cell lines. Poly-A mRNA from heart, brain, muscle, kidney and pancreas failed to react with either the trophinin or tastin probes.

C. Expression and Localization of Trophinin and Tastin in Human Placental and Endometrial Tissues.

Tissues embedded in paraffin were obtained from the University of California at San Diego Tissue Bank. These tissues included placenta, endometrial, liver, lung, kidney, ovary, spleen, colon, testes, brain, and spinal cord. Paraffin embedded tissue sections (0.5 or 3 $\mu$M thick) were deparaffinized and microwaved in 10 mM citrate buffer, pH 6.0, in order to recover antigenic activities (Shi et al., *J. Histochem. Cytochem.* 39:741–748 (1991), which is incorporated herein by reference). The sections were stained with anti-trophinin or anti-trophinin-assisting protein antibodies and FITC goat anti-rabbit antibodies according to methods described above (see Example VI, subsection A). Mouse anti-lamp-1 antibodies were used to detect endosomes and lysosomes (Fukuda, supra, 1991). Double immunostaining for lamp-1 and trophinin was performed in de-paraffinized and microwaved sections using the following sequence of reagents (Williams and Fukuda, *J. Cell Biol.* 111:955–966 (1990) which is incorporated herein by reference): 1) anti-lamp-1 antibody, 2) rhodamine conjugated goat anti-mouse IgG antibody (Sigma, St Louis, Mo.), 3) anti-trophinin antibody and 4) FITC goat anti-rabbit IgG antibody (Cappel, Durham, N.C.).

Anti-trophinin and anti-tastin antibodies failed to stain cells in placenta, liver, lung, kidney, ovary, spleen, colon, testes, brain, and spinal cord, except for macrophages present in the tissues (not shown). Trophinin was not detected in term placental tissues or in placental tissues from early (7–10 week) pregnancy (except for macrophages), whereas trophinin was readily detected in focal regions in the apical plasma membranes of syncytiotrophoblasts of chorionic villi at 7 weeks pregnancy (FIG. 10A). Trophinin also was present in cytoplasmic vesicles of syncytiotrophoblasts in the chorionic villi from 7–10 week pregnancy (FIG. 10B). Double immunostaining with the lamp-1 lysosome marker showed co-localization of trophinin and lamp-1 in these vesicles, indicating that trophinins are present in lysosomes and/or endosomes (not shown). These observations indicate that trophinin expression is strictly regulated and appears on the surface membranes of syncytiotrophoblasts at early stages of pregnancy but not at later stages of pregnancy. Trophinins seen in lysosomes of syncytiotrophoblasts at later stages of pregnancy can be undergoing degradation after being removed from the cell surface. Tastin was not detected in most of the chorionic villi from 7–10 week pregnancy, except for a weak signal in the lysosomes in syncytiotrophoblasts (not shown).

In addition to expression by the embryo, trophinin also is expressed in the uterus at the apical plasma membrane of the surface epithelium on day 16/17 endometrium (FIG. 10C), but not in endometrium during the proliferation stage (day 6–13) or ovulation stage (day 14). Endometrial biopsy samples taken from late secretory phases (day 20–28) showed staining for trophinin in the mucin.

Figure 11A:
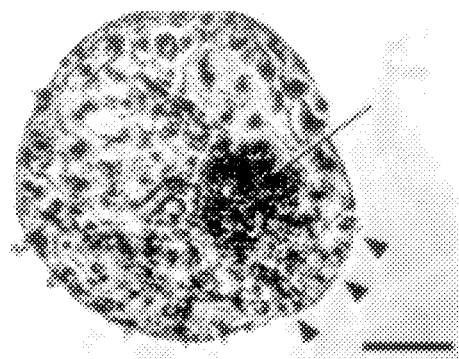
FIGS. 11A, 11B, 11C and 11D display immunofluorescence micrographs of a monkey embryo and the implantation site from a monkey stained via antibodies to the N-terminal region of trophinin (residue 23–31).

Tastin could not be detected in any of the above endometrial tissue samples except for mucin. These results, like those for the embryo, demonstrate that trophinin expression is strictly regulated in endometrial tissue, with trophinin appearing for only a short time on the cell surface. Thus, trophinin is involved in embryo implantation as its pattern of expression is consistent with the concept of an implantation window Further evidence that trophinin is involved in implantation comes for immunofluorescence analysis of a blastocyst taken from a Rhesus monkey. After removal of the exterior Zona pellucida, the expanded blastocyst showed strong staining at the apical plasma membranes of the trophectoderm cells. More intense staining for trophinin was observed on trophoblast cells located at the embryonic pole as opposed to the mural pole (see FIG. 11A and 11B). Such polarized staining is consistent with the observation that the embryonic pole of both primate and human blastocysts is the site of attachment to the endometrial epithelium (Enders et al, supra (1981); Knoth and Larson, supra (1972) and Lindenberg et al, supra (1986)).

Figure 11C:
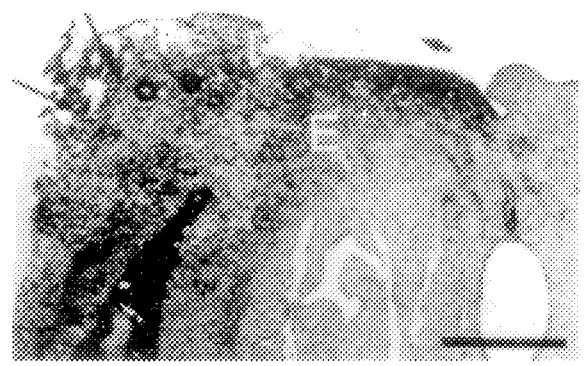
Figure 11B:
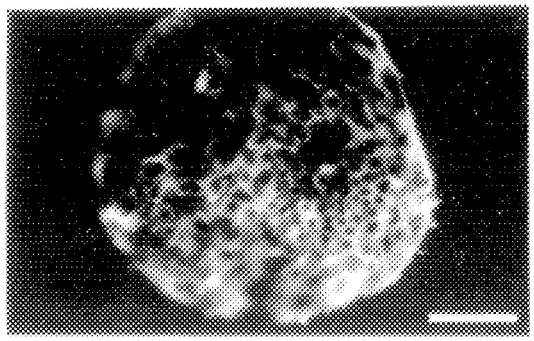
Figure 11D:
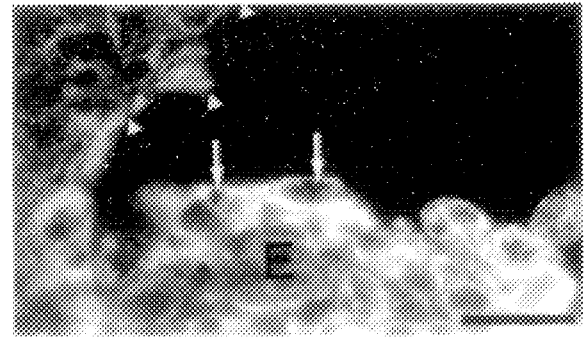

Trophinin was also detected both in trophoblasts and endometrial epithelial cells at the implantation site of a Macaque monkey (see FIG. 11C and 11D). Trophinin positive cells were seen among those anchoring villi and cytotrophoblasts of the blastocyst and in plaque cells or hypertrophic endometrial epithelium (not shown). As shown in FIG. 11D, the most intense staining for trophinin was observed among trophoblast and endometrial epithelial cells located at the site of adhesion between these two tissues. These results with non-human primate embryos together with the studies on human endometrial and implantation site tissues provide strong support for the conservation of trophinin as a mediator of implantation among all primates.

EXAMPLE VII

Use of Trophinin to Mediate Adhesion Between Cells

This example provides methods to adhere cells together using trophinin.

COS-1 cells were transfected with a mixture of trophinin and tastin cDNA and evaluated for cell adhesion capability. Transfected cells that were suspended in HBS with 1 mM EDTA and maintained at RT formed distinct cell aggregates after about 10–20 min, while untransfected COS-1 cells formed little if any aggregates under the same conditions. Thus, the expression of both trophinin and tastin in COS-1 cells provided these cells with the ability to aggregate together in suspension.

The ability of various cells to adhere to a monolayer of COS-1 cells transfected with trophinin and tastin cDNA was evaluated in the adhesion cell assay in the presence of 1 mM EDTA. COS-1 cells transfected with trophinin and tastin cDNA bound the monolayer while COS-1 cells transfected with the control pcDNA1 vector failed to show significant binding. When the monolayer was pretreated for 1 hr at RT with antisera to GST551, GST552 or GST553 trophinin external domain fusion proteins, the ability of the monolayer to adhere to COS-1 cells transfected with trophinin and tastin cDNA was greatly diminished. These results indicate that transfection with both trophinin and tastin, a trophinin-assisted protein, can confer the property of undergoing adhesion mediated by trophinin. The inhibition of cell adhesion by antibodies to the hydrophilic external domains of trophinin confirms the role of such domains in trophinin-mediated cell adhesion.

Trophinin-mediated cell adhesion between HT-H suspension cells and a monolayer of SNG-M cells and between SNG-M cells and a monolayer of SNG-M cells was also tested for inhibition by antibodies to trophinin. In both cases, pretreatment of the monolayer with antiserum to GST553 (FIG. 1D) or with Fab' fragments of antibodies to GST553 significantly inhibited the amount of cell adhesion. Similar results were obtained when SNG-M cells were added to an SNG-M cell monolayer. In contrast to these results, pretreatment of the SNG-M cell monolayer with preimmune rabbit sera or with antibodies to a synthetic peptide of the amino terminal region of trophinin (residues 23–31) failed to inhibit adhesion of SNG-M or HT-H cells. These experiments provide further evidence for the role of the external hydrophilic domains of trophinin in trophinin-mediated cell adhesion.

Although the invention has been described with reference to the examples provided above, it should be understood that various modifications can be made without departing from the spirit of the invention. Accordingly, the invention is limited only by the claims.

---

I claim:

1. An anti-trophinin antibody that can specifically bind to human trophinin or an active fragment thereof.

2. A probe, comprising the antibody of claim 1 and a detectable label.

3. A probe, comprising the antibody of claim 1 and a detectable label.

4. An antibody that can specifically bind to a trophinin-assisting protein selected from the group consisting of tastin (SEQ ID NO:5), bystin (SEQ ID NO:7) and lastin (SEQ ID NO:9).

5. The antibody of claim 4, wherein said trophinin-assisting protein is tastin.

6. The antibody of claim 4, wherein said trophinin-assisting protein is bystin.

7. The antibody of claim 4, wherein said trophinin-assisting protein is lastin.

8. The anti-trophinin antibody of claim 1, wherein said antibody specifically binds to an extracellular membrane domain of trophinin selected from the group consisting of:

residues 278 to 364 (SEQ ID NO: 20; FIG. 3);

residues 441 to 512 (SEQ ID NO: 21; FIG. 3); and residues 634 to 719 (SEQ ID NO: 22; FIG. 3).

9. A trophinin antagonist that can bind to trophinin or a trophinin-assisting protein specifically, wherein the antagonist reduces or inhibits trophinin-mediated cell adhesion and wherein the antagonist is an antibody.

10. The antagonist of claim 9, wherein the antagonist can specifically bind to trophinin.

11. The antagonist of claim 9, wherein the antagonist can specifically bind to tastin.

12. The antagonist of claim 9, wherein the antagonist can specifically bind to bystin.

13. The antagonist of claim 9, wherein the antagonist can specifically bind to lastin.

14. The antagonist of claim 9, wherein the antagonist can reduce or inhibit trophinin-mediated cell adhesion in vitro.

* * * * *

UNITED STATES PATENT AND TRADEMARK OFFICE
CERTIFICATE OF CORRECTION

PATENT NO.    : 5,880,267
DATED         : March 9, 1999
INVENTOR(S)   : Michiko N. Fukuda It is certified that error appears in the above-identified patent and that said Letters Patent is hereby corrected as shown below:

Column 18,
Line 61, please delete "SB" and replace therefor with --5B--.

Column 25,
Line 64, please delete "ad here" and replace therefore with --adhere--.

Column 27,
Line 28, please delete "used t" and replace therefor with --used to--.
Line 35, please delete "be cause" and replace therefor with --because--.

Column 30,
Line 3, please delete "13-turn" and replace therefor with --β-turn--.

Column 34,
Line 30, please delete "32P" and replace therefor with --$^{32}$P--.

Column 77,
Line 15, please delete "claim 1" and replace therefor with --claim 4--.

Signed and Sealed this

Fourteenth Day of August, 2001

Attest:

NICHOLAS P. GODICI
Attesting Officer    Acting Director of the United States Patent and Trademark Office

SEQUENCE LISTING ( 1 ) GENERAL INFORMATION:

( i i i ) NUMBER OF SEQUENCES: 22

( 2 ) INFORMATION FOR SEQ ID NO:1:

( i ) SEQUENCE CHARACTERISTICS:
    ( A ) LENGTH: 2524 base pairs
    ( B ) TYPE: nucleic acid
    ( C ) STRANDEDNESS: single
    ( D ) TOPOLOGY: linear ( i x ) FEATURE:
    ( A ) NAME/KEY: CDS
    ( B ) LOCATION: 28..2275

( x i ) SEQUENCE DESCRIPTION: SEQ ID NO:1:

```
GTGGCTGGGC CCTGGAATTG GGATGAC ATG GAT ATC GAC TGC CTA ACA AGG              51
                              Met Asp Ile Asp Cys Leu Thr Arg
                               1               5

GAA GAG TTA GGC GAT GAT TCT CAG GCC TGG AGC AGA TTT TCA TTT GAA            99
Glu Glu Leu Gly Asp Asp Ser Gln Ala Trp Ser Arg Phe Ser Phe Glu
         10              15                  20

ATT GAG GCC AGA GCC CAA GAA AAT GCA GAT GCC AGC ACC AAC GTC AAC           147
Ile Glu Ala Arg Ala Gln Glu Asn Ala Asp Ala Ser Thr Asn Val Asn
 25              30                  35                      40

TTC AGC AGA GGA GCT AGT ACC AGG GCT GGC TTC AGC GAT CGT GCT AGT           195
Phe Ser Arg Gly Ala Ser Thr Arg Ala Gly Phe Ser Asp Arg Ala Ser
             45                  50                  55

ATT AGC TTC AAT GGT GCA CCC AGC TCC AGT GGT GGC TTC AGT GGT GGA           243
Ile Ser Phe Asn Gly Ala Pro Ser Ser Ser Gly Gly Phe Ser Gly Gly
             60                  65                  70

CCT GGC ATT ACC TTT GGT GTT GCA CCC AGC ACC AGT GCC AGC TTC AGC           291
Pro Gly Ile Thr Phe Gly Val Ala Pro Ser Thr Ser Ala Ser Phe Ser
             75                  80                  85

AAT ACA GCC AGC ATT AGC TTT GGT GGT ACA CTG AGC ACT AGC TCC AGC           339
Asn Thr Ala Ser Ile Ser Phe Gly Gly Thr Leu Ser Thr Ser Ser Ser
         90                  95                 100

TTC AGC AGC GCA GCC AGC ATT AGC TTT GGT TGT GCA CAC AGC ACC AGC           387
Phe Ser Ser Ala Ala Ser Ile Ser Phe Gly Cys Ala His Ser Thr Ser
105                 110                 115                 120

ACT AGT TTC AGC AGT GAA GCC AGC ATT AGC TTT GGT GGC ATG CCT TGT           435
Thr Ser Phe Ser Ser Glu Ala Ser Ile Ser Phe Gly Gly Met Pro Cys
                125                 130                 135

ACC AGT GCC AGC TTT AGT GGT GGA GTC AGC TCT AGT TTT AGT GGC CCA           483
Thr Ser Ala Ser Phe Ser Gly Gly Val Ser Ser Ser Phe Ser Gly Pro
             140                 145                 150

CTC AGC ACC AGT GCC ACT TTC AGT GGT GGA GCC AGC TCT GGC TTT GGA           531
Leu Ser Thr Ser Ala Thr Phe Ser Gly Gly Ala Ser Ser Gly Phe Gly
             155                 160                 165

GGC ACA CTC AGC ACC ACG GCT GGC TTT AGT GGT GTA CTC AGC ACT AGC           579
Gly Thr Leu Ser Thr Thr Ala Gly Phe Ser Gly Val Leu Ser Thr Ser
         170                 175                 180

ACC AGC TTT GGC AGT GCA CCC ACA ACG AGC ACA GTC TTC AGT AGT GCG           627
Thr Ser Phe Gly Ser Ala Pro Thr Thr Ser Thr Val Phe Ser Ser Ala
185                 190                 195                 200

CTT AGC ACC AGC ACT GGC TTT GGA GGC ATA CTC AGC ACC AGT GTC TGT           675
Leu Ser Thr Ser Thr Gly Phe Gly Gly Ile Leu Ser Thr Ser Val Cys
                205                 210                 215

TTT GGT GGC TCT CCC AGC TCC AGT GGT AGC TTT GGT GGT ACA CTC AGT           723
Phe Gly Gly Ser Pro Ser Ser Ser Gly Ser Phe Gly Gly Thr Leu Ser
             220                 225                 230

ACC AGT ATC TGC TTC GGT GGC TCT CCC TGC ACC AGC ACT GGC TTT GGA           771
Thr Ser Ile Cys Phe Gly Gly Ser Pro Cys Thr Ser Thr Gly Phe Gly
             235                 240                 245

GGC ACA CTT AGC ACC AGT GTC TCC TTT GGT GGC TCT TCC AGC ACC AGT           819
Gly Thr Leu Ser Thr Ser Val Ser Phe Gly Gly Ser Ser Ser Thr Ser
         250                 255                 260
```

| | | | | | | | | | | | | | | | | |
|---|---|---|---|---|---|---|---|---|---|---|---|---|---|---|---|---|
| GCC | AAT | TTT | GGT | GGT | ACA | CTA | AGT | ACC | AGC | ATC | TGC | TTT | GAT | GGC | TCT | 867 |
| Ala | Asn | Phe | Gly | Gly | Thr | Leu | Ser | Thr | Ser | Ile | Cys | Phe | Asp | Gly | Ser | |
| 265 | | | | | 270 | | | | 275 | | | | | | 280 | |
| CCC | AGC | ACT | GGT | GCT | GGC | TTT | GGT | GGT | GCT | CTC | AAC | ACC | AGT | GCC | AGC | 915 |
| Pro | Ser | Thr | Gly | Ala | Gly | Phe | Gly | Gly | Ala | Leu | Asn | Thr | Ser | Ala | Ser | |
| | | | | 285 | | | | | 290 | | | | | 295 | | |
| TTT | GGC | AGT | GTG | CTC | AAC | ACC | AGT | ACT | GGT | TTT | GGT | GGT | GCT | ATG | AGC | 963 |
| Phe | Gly | Ser | Val | Leu | Asn | Thr | Ser | Thr | Gly | Phe | Gly | Gly | Ala | Met | Ser | |
| | | | 300 | | | | | 305 | | | | | 310 | | | |
| ACC | AGT | GCT | GAC | TTT | GGC | GGT | ACA | CTA | AGC | ACC | AGT | GTC | TGC | TTT | GGT | 1011 |
| Thr | Ser | Ala | Asp | Phe | Gly | Gly | Thr | Leu | Ser | Thr | Ser | Val | Cys | Phe | Gly | |
| | | 315 | | | | | 320 | | | | | 325 | | | | |
| GGC | TCT | CCT | GGC | ACC | AGT | GTC | AGC | TTT | GGC | AGT | GCA | CTC | AAC | ACC | AAT | 1059 |
| Gly | Ser | Pro | Gly | Thr | Ser | Val | Ser | Phe | Gly | Ser | Ala | Leu | Asn | Thr | Asn | |
| | 330 | | | | | 335 | | | | | 340 | | | | | |
| GCT | GGT | TAT | GGT | GGT | GCT | GTC | AGC | ACC | AAC | ACT | GAC | TTT | GGT | GGT | ACA | 1107 |
| Ala | Gly | Tyr | Gly | Gly | Ala | Val | Ser | Thr | Asn | Thr | Asp | Phe | Gly | Gly | Thr | |
| 345 | | | | | 350 | | | | | 355 | | | | | 360 | |
| CTA | AGC | ACC | AGC | GTC | TGT | TTT | GGT | GGC | TCT | CCC | AGC | ACC | AGT | GCT | GGC | 1155 |
| Leu | Ser | Thr | Ser | Val | Cys | Phe | Gly | Gly | Ser | Pro | Ser | Thr | Ser | Ala | Gly | |
| | | | | 365 | | | | | 370 | | | | | 375 | | |
| TTT | GGT | GGT | GCA | CTC | AAC | ACC | AAT | GCC | AGC | TTT | GGC | TGT | GCC | GTC | AGC | 1203 |
| Phe | Gly | Gly | Ala | Leu | Asn | Thr | Asn | Ala | Ser | Phe | Gly | Cys | Ala | Val | Ser | |
| | | | 380 | | | | | 385 | | | | | 390 | | | |
| ACC | AGT | GCC | AGC | TTC | AGT | GGT | GCT | GTC | AGC | ACC | AGT | GCT | TGC | TTC | AGT | 1251 |
| Thr | Ser | Ala | Ser | Phe | Ser | Gly | Ala | Val | Ser | Thr | Ser | Ala | Cys | Phe | Ser | |
| | | 395 | | | | | 400 | | | | | 405 | | | | |
| GGT | GCA | CCA | ATC | ACC | AAC | CCT | GGC | TTT | GGC | GGT | GCA | TTT | AGC | ACC | AGT | 1299 |
| Gly | Ala | Pro | Ile | Thr | Asn | Pro | Gly | Phe | Gly | Gly | Ala | Phe | Ser | Thr | Ser | |
| | 410 | | | | | 415 | | | | | 420 | | | | | |
| GCT | GGC | TTC | GGT | GGT | GCA | CTT | AGT | ACC | GCT | GCT | GAC | TTC | GGT | GGT | ACT | 1347 |
| Ala | Gly | Phe | Gly | Gly | Ala | Leu | Ser | Thr | Ala | Ala | Asp | Phe | Gly | Gly | Thr | |
| 425 | | | | | 430 | | | | | 435 | | | | | 440 | |
| CCC | AGC | AAC | AGC | ATT | GGC | TTT | GGT | GCT | GCT | CCC | AGC | ACC | AGT | GTC | AGC | 1395 |
| Pro | Ser | Asn | Ser | Ile | Gly | Phe | Gly | Ala | Ala | Pro | Ser | Thr | Ser | Val | Ser | |
| | | | | 445 | | | | | 450 | | | | | 455 | | |
| TTT | GGT | GGT | GCT | CAT | GGC | ACC | AGC | CTC | TGT | TTT | GGT | GGA | GCT | CCC | AGC | 1443 |
| Phe | Gly | Gly | Ala | His | Gly | Thr | Ser | Leu | Cys | Phe | Gly | Gly | Ala | Pro | Ser | |
| | | | 460 | | | | | 465 | | | | | 470 | | | |
| ACC | AGC | CTC | TGC | TTT | GGC | AGT | GCA | TCT | AAT | ACT | AAC | CTA | TGC | TTT | GGT | 1491 |
| Thr | Ser | Leu | Cys | Phe | Gly | Ser | Ala | Ser | Asn | Thr | Asn | Leu | Cys | Phe | Gly | |
| | | 475 | | | | | 480 | | | | | 485 | | | | |
| GGC | CCT | CCT | AGC | ACC | AGT | GCC | TGC | TTT | AGT | GGT | GCT | ACC | AGC | CCT | AGT | 1539 |
| Gly | Pro | Pro | Ser | Thr | Ser | Ala | Cys | Phe | Ser | Gly | Ala | Thr | Ser | Pro | Ser | |
| | 490 | | | | | 495 | | | | | 500 | | | | | |
| TTT | TGT | GAT | GGA | CCC | AGC | ACC | AGT | ACC | GGT | TTC | AGC | TTT | GGC | AAT | GGG | 1587 |
| Phe | Cys | Asp | Gly | Pro | Ser | Thr | Ser | Thr | Gly | Phe | Ser | Phe | Gly | Asn | Gly | |
| 505 | | | | | 510 | | | | | 515 | | | | | 520 | |
| TTA | AGC | ACC | AAT | GCT | GGA | TTT | GGT | GGT | GGA | CTG | AAC | ACC | AGT | GCT | GGC | 1635 |
| Leu | Ser | Thr | Asn | Ala | Gly | Phe | Gly | Gly | Gly | Leu | Asn | Thr | Ser | Ala | Gly | |
| | | | | 525 | | | | | 530 | | | | | 535 | | |
| TTT | GGT | GGT | GGC | CTA | GGC | ACC | AGT | GCT | GGC | TTC | AGT | GGT | GGC | CTA | AGC | 1683 |
| Phe | Gly | Gly | Gly | Leu | Gly | Thr | Ser | Ala | Gly | Phe | Ser | Gly | Gly | Leu | Ser | |
| | | | 540 | | | | | 545 | | | | | 550 | | | |
| ACA | AGT | TCT | GGC | TTT | GAT | GGT | GGG | CTA | GGT | ACC | AGC | GCT | GGC | TTC | GGT | 1731 |
| Thr | Ser | Ser | Gly | Phe | Asp | Gly | Gly | Leu | Gly | Thr | Ser | Ala | Gly | Phe | Gly | |
| | | 555 | | | | | 560 | | | | | 565 | | | | |
| GGA | GGA | CCA | GGC | ACC | AGC | ACT | GGT | TTT | GGT | GGT | GGA | CTG | GGC | ACC | AGT | 1779 |
| Gly | Gly | Pro | Gly | Thr | Ser | Thr | Gly | Phe | Gly | Gly | Gly | Leu | Gly | Thr | Ser | |
| | 570 | | | | | 575 | | | | | 580 | | | | | |

| | | | | | | | | | | | | | | | | |
|---|---|---|---|---|---|---|---|---|---|---|---|---|---|---|---|---|
|GCT|GGC|TTC|AGT|GGC|GGA|CTG|GGC|ACC|AGT|GCT|GGC|TTT|GGT|GGT|GGA|1827|
|Ala|Gly|Phe|Ser|Gly|Gly|Leu|Gly|Thr|Ser|Ala|Gly|Phe|Gly|Gly|Gly| |
|585| | | | |590| | | | |595| | | | |600| |
|CTG|GTC|ACT|AGT|GAT|GGC|TTT|GGT|GGT|GGA|CTG|GGC|ACC|AAT|GCT|AGT|1875|
|Leu|Val|Thr|Ser|Asp|Gly|Phe|Gly|Gly|Gly|Leu|Gly|Thr|Asn|Ala|Ser| |
| | | | |605| | | | |610| | | | |615| | |
|TTC|GGC|AGC|ACA|CTT|GGC|ACC|AGT|GCT|GGC|TTT|AGT|GGT|GGC|CTC|AGC|1923|
|Phe|Gly|Ser|Thr|Leu|Gly|Thr|Ser|Ala|Gly|Phe|Ser|Gly|Gly|Leu|Ser| |
| | | |620| | | | |625| | | | |630| | | |
|ACC|AGC|GAT|GGC|TTT|GGC|AGT|AGG|CCT|AAT|GCC|AGC|TTC|GAC|AGA|GGA|1971|
|Thr|Ser|Asp|Gly|Phe|Gly|Ser|Arg|Pro|Asn|Ala|Ser|Phe|Asp|Arg|Gly| |
| | |635| | | | |640| | | | |645| | | | |
|CTG|AGT|ACC|ATC|ATT|GGC|TTT|GGC|AGT|GGT|TCC|AAC|ACC|AGC|ACT|GGC|2019|
|Leu|Ser|Thr|Ile|Ile|Gly|Phe|Gly|Ser|Gly|Ser|Asn|Thr|Ser|Thr|Gly| |
|650| | | | |655| | | | |660| | | | | | |
|TTT|ACT|GGC|GAA|CCC|AGC|ACC|AGC|ACG|GGC|TTC|AGT|AGT|GGA|CCC|AGT|2067|
|Phe|Thr|Gly|Glu|Pro|Ser|Thr|Ser|Thr|Gly|Phe|Ser|Ser|Gly|Pro|Ser| |
|665| | | | |670| | | | |675| | | | |680| |
|TCT|ATT|GTT|GGC|TTC|AGC|GGT|GGA|CCA|AGC|ACT|GGT|GTT|GGC|TTC|TGC|2115|
|Ser|Ile|Val|Gly|Phe|Ser|Gly|Gly|Pro|Ser|Thr|Gly|Val|Gly|Phe|Cys| |
| | | | |685| | | | |690| | | | |695| | |
|AGT|GGA|CCA|AGC|ACC|AGT|GGC|TTC|AGC|GGT|GGA|CCC|AGC|ACA|GGA|GCT|2163|
|Ser|Gly|Pro|Ser|Thr|Ser|Gly|Phe|Ser|Gly|Gly|Pro|Ser|Thr|Gly|Ala| |
| | |700| | | | |705| | | | |710| | | | |
|GGC|TTC|GGC|GGT|GGA|CCA|AAC|ACT|GGT|GCT|GGC|TTT|GGT|GGT|GGA|CCG|2211|
|Gly|Phe|Gly|Gly|Gly|Pro|Asn|Thr|Gly|Ala|Gly|Phe|Gly|Gly|Gly|Pro| |
| | |715| | | | |720| | | | |725| | | | |
|AGC|ACC|AGT|GCT|GGC|TTT|GGC|AGT|GGA|GCC|GCC|AGT|CTT|GGT|GCC|TGT|2259|
|Ser|Thr|Ser|Ala|Gly|Phe|Gly|Ser|Gly|Ala|Ala|Ser|Leu|Gly|Ala|Cys| |
| |730| | | | |735| | | | |740| | | | | |
|GGC|TTC|TCG|TAT|GGC|T|AGTGAGGTTT|CAGATACCGC|TAATAAATTG|CAGTAGTCCT| | | | | | |2315|
|Gly|Phe|Ser|Tyr|Gly| | | | | | | | | | | | |
|745| | | | | | | | | | | | | | | | |

| | | | | |
|---|---|---|---|---|
|TCCCATGGAG|CCAAAGTACC|TTGGATCTTT|GTCCACACAG|CAGTCAAGGC AGTTATGCC|2375|
|CATCAGCTGA|GGGTGTCATG|TGATGGAAAA|ATCTGTTTGC|TGTTCCTGCT TTATTGTTTG|2435|
|CTTTCTGTGT|GCTGTCATAT|TTTGGTATCA|GAGTTACATT|AAATTTGCAA AATGAAAAAA|2495|
|AAAAAAAAAA|AAAAAAAAAA|AAAAAAAA| | |2524|

( 2 ) INFORMATION FOR SEQ ID NO:2:

( i ) SEQUENCE CHARACTERISTICS:
        ( A ) LENGTH: 749 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| | | | | | | | | | | | | | | |
|---|---|---|---|---|---|---|---|---|---|---|---|---|---|---|
|Met|Asp|Ile|Asp|Cys|Leu|Thr|Arg|Glu|Glu|Leu|Gly|Asp|Asp|Ser|Gln|
|1| | | |5| | | | |10| | | | |15|
|Ala|Trp|Ser|Arg|Phe|Ser|Phe|Glu|Ile|Glu|Ala|Arg|Ala|Gln|Glu|Asn|
| | | |20| | | | |25| | | | |30| |
|Ala|Asp|Ala|Ser|Thr|Asn|Val|Asn|Phe|Ser|Arg|Gly|Ala|Ser|Thr|Arg|
| | | |35| | | | |40| | | | |45| |
|Ala|Gly|Phe|Ser|Asp|Arg|Ala|Ser|Ile|Ser|Phe|Asn|Gly|Ala|Pro|Ser|
| | |50| | | | |55| | | | |60| | |
|Ser|Ser|Gly|Gly|Phe|Ser|Gly|Gly|Pro|Gly|Ile|Thr|Phe|Gly|Val|Ala|
|65| | | | |70| | | | |75| | | | |80|

```
Pro  Ser  Thr  Ser  Ala  Ser  Phe  Ser  Asn  Thr  Ala  Ser  Ile  Ser  Phe  Gly
               85                      90                      95

Gly  Thr  Leu  Ser  Thr  Ser  Ser  Ser  Phe  Ser  Ala  Ala  Ser  Ile  Ser
               100                     105                     110

Phe  Gly  Cys  Ala  His  Ser  Thr  Thr  Ser  Phe  Ser  Glu  Ala  Ser
               115                     120                     125

Ile  Ser  Phe  Gly  Gly  Met  Pro  Cys  Thr  Ser  Ala  Ser  Phe  Ser  Gly  Gly
          130                      135                     140

Val  Ser  Ser  Ser  Phe  Ser  Gly  Pro  Leu  Ser  Thr  Ser  Ala  Thr  Phe  Ser
145                      150                     155                          160

Gly  Gly  Ala  Ser  Ser  Gly  Phe  Gly  Gly  Thr  Leu  Ser  Thr  Thr  Ala  Gly
                    165                     170                          175

Phe  Ser  Gly  Val  Leu  Ser  Thr  Ser  Thr  Ser  Phe  Gly  Ser  Ala  Pro  Thr
               180                     185                     190

Thr  Ser  Thr  Val  Phe  Ser  Ser  Ala  Leu  Ser  Thr  Ser  Thr  Gly  Phe  Gly
          195                     200                     205

Gly  Ile  Leu  Ser  Thr  Ser  Val  Cys  Phe  Gly  Gly  Ser  Pro  Ser  Ser  Ser
     210                     215                     220

Gly  Ser  Phe  Gly  Gly  Thr  Leu  Ser  Thr  Ser  Ile  Cys  Phe  Gly  Gly  Ser
225                      230                     235                          240

Pro  Cys  Thr  Ser  Thr  Gly  Phe  Gly  Gly  Thr  Leu  Ser  Thr  Ser  Val  Ser
               245                     250                     255

Phe  Gly  Gly  Ser  Ser  Ser  Thr  Ser  Ala  Asn  Phe  Gly  Gly  Thr  Leu  Ser
               260                     265                     270

Thr  Ser  Ile  Cys  Phe  Asp  Gly  Ser  Pro  Ser  Thr  Gly  Ala  Gly  Phe  Gly
          275                     280                     285

Gly  Ala  Leu  Asn  Thr  Ser  Ala  Ser  Phe  Gly  Ser  Val  Leu  Asn  Thr  Ser
     290                     295                     300

Thr  Gly  Phe  Gly  Gly  Ala  Met  Ser  Thr  Ser  Ala  Asp  Phe  Gly  Gly  Thr
305                      310                     315                          320

Leu  Ser  Thr  Ser  Val  Cys  Phe  Gly  Gly  Ser  Pro  Gly  Thr  Ser  Val  Ser
               325                     330                     335

Phe  Gly  Ser  Ala  Leu  Asn  Thr  Asn  Ala  Gly  Tyr  Gly  Gly  Ala  Val  Ser
               340                     345                     350

Thr  Asn  Thr  Asp  Phe  Gly  Gly  Thr  Leu  Ser  Thr  Ser  Val  Cys  Phe  Gly
          355                     360                     365

Gly  Ser  Pro  Ser  Thr  Ser  Ala  Gly  Phe  Gly  Gly  Ala  Leu  Asn  Thr  Asn
     370                     375                     380

Ala  Ser  Phe  Gly  Cys  Ala  Val  Ser  Thr  Ser  Ala  Ser  Phe  Ser  Gly  Ala
385                      390                     395                          400

Val  Ser  Thr  Ser  Ala  Cys  Phe  Ser  Gly  Ala  Pro  Ile  Thr  Asn  Pro  Gly
               405                     410                     415

Phe  Gly  Gly  Ala  Phe  Ser  Thr  Ser  Ala  Gly  Phe  Gly  Gly  Ala  Leu  Ser
               420                     425                     430

Thr  Ala  Ala  Asp  Phe  Gly  Gly  Thr  Pro  Ser  Asn  Ser  Ile  Gly  Phe  Gly
          435                     440                     445

Ala  Ala  Pro  Ser  Thr  Ser  Val  Ser  Phe  Gly  Gly  Ala  His  Gly  Thr  Ser
     450                     455                     460

Leu  Cys  Phe  Gly  Gly  Ala  Pro  Ser  Thr  Ser  Leu  Cys  Phe  Gly  Ser  Ala
465                      470                     475                          480

Ser  Asn  Thr  Asn  Leu  Cys  Phe  Gly  Gly  Pro  Pro  Ser  Thr  Ser  Ala  Cys
               485                     490                     495

Phe  Ser  Gly  Ala  Thr  Ser  Pro  Ser  Phe  Cys  Asp  Gly  Pro  Ser  Thr  Ser
               500                     505                     510
```

Thr Gly Phe Ser Phe Gly Asn Gly Leu Ser Thr Asn Ala Gly Phe Gly
            515                 520                 525

Gly Gly Leu Asn Thr Ser Ala Gly Phe Gly Gly Gly Leu Gly Thr Ser
        530                 535                 540

Ala Gly Phe Ser Gly Gly Leu Ser Thr Ser Ser Gly Phe Asp Gly Gly
545                     550                 555                 560

Leu Gly Thr Ser Ala Gly Phe Gly Gly Gly Pro Gly Thr Ser Thr Gly
                565                 570                 575

Phe Gly Gly Gly Leu Gly Thr Ser Ala Gly Phe Ser Gly Gly Leu Gly
            580                 585                 590

Thr Ser Ala Gly Phe Gly Gly Gly Leu Val Thr Ser Asp Gly Phe Gly
            595                 600                 605

Gly Gly Leu Gly Thr Asn Ala Ser Phe Gly Ser Thr Leu Gly Thr Ser
        610                 615                 620

Ala Gly Phe Ser Gly Gly Leu Ser Thr Ser Asp Gly Phe Gly Ser Arg
625                     630                 635                 640

Pro Asn Ala Ser Phe Asp Arg Gly Leu Ser Thr Ile Ile Gly Phe Gly
                645                 650                 655

Ser Gly Ser Asn Thr Ser Thr Gly Phe Thr Gly Glu Pro Ser Thr Ser
            660                 665                 670

Thr Gly Phe Ser Ser Gly Pro Ser Ser Ile Val Gly Phe Ser Gly Gly
        675                 680                 685

Pro Ser Thr Gly Val Gly Phe Cys Ser Gly Pro Ser Thr Ser Gly Phe
    690                 695                 700

Ser Gly Gly Pro Ser Thr Gly Ala Gly Phe Gly Gly Gly Pro Asn Thr
705                 710                 715                 720

Gly Ala Gly Phe Gly Gly Gly Pro Ser Thr Ser Ala Gly Phe Gly Ser
                725                 730                 735

Gly Ala Ala Ser Leu Gly Ala Cys Gly Phe Ser Tyr Gly
                740                 745

( 2 ) INFORMATION FOR SEQ ID NO:3:

( i ) SEQUENCE CHARACTERISTICS:
        ( A ) LENGTH: 674 amino acids
        ( B ) TYPE: amino acid
        ( D ) TOPOLOGY: linear ( x i ) SEQUENCE DESCRIPTION: SEQ ID NO:3:

Phe Ser Gly Gly Pro Gly Ile Thr Phe Gly Val Ala Pro Ser Thr Ser
1               5                   10                  15

Ala Ser Phe Ser Asn Thr Ala Ser Ile Ser Phe Gly Gly Thr Leu Ser
                20                  25                  30

Thr Ser Ser Ser Phe Ser Ser Ala Ala Ser Ile Ser Phe Gly Cys Ala
            35                  40                  45

His Ser Thr Ser Thr Ser Phe Ser Ser Glu Ala Ser Ile Ser Phe Gly
    50                  55                  60

Gly Met Pro Cys Thr Ser Ala Ser Phe Ser Gly Gly Val Ser Ser Ser
65                  70                  75                      80

Phe Ser Gly Pro Leu Ser Thr Ser Ala Thr Phe Ser Gly Gly Ala Ser
                85                  90                  95

Ser Gly Phe Gly Gly Thr Leu Ser Thr Thr Ala Gly Phe Ser Gly Val
            100                 105                 110

Leu Ser Thr Ser Thr Ser Phe Gly Ser Ala Pro Thr Thr Ser Thr Val
        115                 120                 125

```
Phe  Ser  Ser  Ala  Leu  Ser  Thr  Ser  Thr  Gly  Phe  Gly  Gly  Ile  Leu  Ser
     130                 135                 140

Thr  Ser  Val  Cys  Phe  Gly  Gly  Ser  Pro  Ser  Ser  Ser  Gly  Ser  Phe  Gly
145                      150                 155                           160

Gly  Thr  Leu  Ser  Ser  Ile  Cys  Phe  Gly  Ser  Pro  Cys  Ser
                    165                 170                 175

Thr  Gly  Phe  Gly  Gly  Thr  Leu  Ser  Thr  Ser  Val  Ser  Phe  Gly  Gly  Ser
               180                      185                      190

Ser  Ser  Thr  Ser  Ala  Asn  Phe  Gly  Gly  Thr  Leu  Ser  Thr  Ser  Ile  Cys
          195                      200                      205

Phe  Asp  Gly  Ser  Pro  Ser  Thr  Gly  Ala  Gly  Phe  Gly  Gly  Ala  Leu  Asn
     210                      215                 220

Thr  Ser  Ala  Ser  Phe  Gly  Ser  Val  Leu  Asn  Thr  Ser  Thr  Gly  Phe  Gly
225                           230                 235                      240

Gly  Ala  Met  Ser  Thr  Ser  Ala  Asp  Phe  Gly  Thr  Leu  Ser  Thr  Ser
                    245                      250                      255

Val  Cys  Phe  Gly  Gly  Ser  Pro  Gly  Thr  Ser  Val  Ser  Phe  Gly  Ser  Ala
               260                      265                      270

Leu  Asn  Thr  Asn  Ala  Gly  Tyr  Gly  Ala  Val  Ser  Thr  Asn  Thr  Asp
          275                 280                      285

Phe  Gly  Gly  Thr  Leu  Ser  Thr  Ser  Val  Cys  Phe  Gly  Gly  Ser  Pro  Ser
     290                      295                 300

Thr  Ser  Ala  Gly  Phe  Gly  Gly  Ala  Leu  Asn  Thr  Asn  Ala  Ser  Phe  Gly
305                           310                 315                      320

Cys  Ala  Val  Ser  Thr  Ser  Ala  Ser  Phe  Ser  Gly  Ala  Val  Ser  Thr  Ser
                    325                      330                      335

Ala  Cys  Phe  Ser  Gly  Ala  Pro  Ile  Thr  Asn  Pro  Gly  Phe  Gly  Gly  Ala
               340                      345                      350

Phe  Ser  Thr  Ser  Ala  Gly  Phe  Gly  Gly  Ala  Leu  Ser  Thr  Ala  Ala  Asp
          355                      360                      365

Phe  Gly  Gly  Thr  Pro  Ser  Asn  Ser  Ile  Gly  Phe  Gly  Ala  Ala  Pro  Ser
     370                      375                 380

Thr  Ser  Val  Ser  Phe  Gly  Gly  Ala  His  Gly  Thr  Ser  Leu  Cys  Phe  Gly
385                           390                 395                      400

Gly  Ala  Pro  Ser  Thr  Ser  Leu  Cys  Phe  Gly  Ser  Ala  Ser  Asn  Thr  Asn
                    405                      410                      415

Leu  Cys  Phe  Gly  Gly  Pro  Pro  Ser  Thr  Ser  Ala  Cys  Phe  Ser  Gly  Ala
               420                      425                 430

Thr  Ser  Pro  Ser  Phe  Cys  Asp  Gly  Pro  Thr  Ser  Thr  Gly  Phe  Ser
          435                      440                      445

Phe  Gly  Asn  Gly  Leu  Ser  Thr  Gly  Phe  Gly  Gly  Leu  Asn  Thr  Ser
     450                      455                 460

Ala  Gly  Phe  Gly  Gly  Gly  Leu  Gly  Thr  Ser  Ala  Gly  Phe  Ser  Gly  Gly
465                      470                      475                      480

Leu  Ser  Thr  Ser  Ser  Gly  Phe  Asp  Gly  Gly  Leu  Gly  Thr  Ser  Ala  Gly
                    485                 490                      495

Phe  Gly  Gly  Gly  Pro  Gly  Thr  Ser  Thr  Gly  Phe  Gly  Gly  Gly  Leu  Gly
               500                      505                      510

Thr  Ser  Ala  Gly  Phe  Ser  Gly  Gly  Leu  Gly  Thr  Ser  Ala  Gly  Phe  Gly
               515                      520                      525

Gly  Gly  Leu  Val  Thr  Ser  Asp  Gly  Phe  Gly  Gly  Leu  Gly  Thr  Asn
     530                      535                 540

Ala  Ser  Phe  Gly  Ser  Thr  Leu  Gly  Thr  Ser  Ala  Gly  Phe  Ser  Gly  Gly
545                      550                      555                      560
```

```
Leu  Ser  Thr  Ser  Asp  Gly  Phe  Gly  Ser  Arg  Pro  Asn  Ala  Ser  Phe  Asp
               565                      570                      575

Arg  Gly  Leu  Ser  Thr  Ile  Ile  Gly  Phe  Gly  Ser  Gly  Ser  Asn  Thr  Ser
               580                      585                      590

Thr  Gly  Phe  Thr  Gly  Glu  Pro  Ser  Thr  Ser  Thr  Gly  Phe  Ser  Ser  Gly
               595                      600                      605

Pro  Ser  Ser  Ile  Val  Gly  Phe  Ser  Gly  Gly  Pro  Ser  Thr  Gly  Gly  Phe
          610                      615                      620

Cys  Ser  Gly  Pro  Ser  Thr  Ser  Gly  Phe  Ser  Gly  Gly  Pro  Ser  Thr  Gly
625                      630                      635                      640

Ala  Gly  Phe  Gly  Gly  Gly  Pro  Asn  Thr  Gly  Ala  Gly  Phe  Gly  Gly  Gly
               645                      650                      655

Pro  Ser  Thr  Ser  Ala  Gly  Phe  Gly  Ser  Gly  Ala  Ala  Ser  Leu  Gly  Ala
               660                      665                      670

Cys  Gly
```

(2) INFORMATION FOR SEQ ID NO:4:

(i) SEQUENCE CHARACTERISTICS:
        (A) LENGTH: 2577 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 111..2445

(xi) SEQUENCE DESCRIPTION: SEQ ID NO:4:

```
CGCCAGGAAC  AGCTTGAGGT  ACCTGAGCCC  TGCCCTCCAG  CAGCACCCGA  GAGGGTCAGG          60

AGAAAGCGG   AGGAAGCTGG  GTAGGCCCTG  AGGGGCCTCG  GTAAGCCATC  ATG  ACC           116
                                                            Met  Thr
                                                             1

ACC  CGG  CAA  GCC  ACG  AAG  GAT  CCC  CTC  CTC  CGG  GGT  GTA  TCT  CCT  ACC   164
Thr  Arg  Gln  Ala  Thr  Lys  Asp  Pro  Leu  Leu  Arg  Gly  Val  Ser  Pro  Thr
          5                        10                       15

CCT  AGC  AAG  ATT  CCG  GTA  CGC  TCT  CAG  AAA  CGC  ACG  CCT  TTC  CCC  ACT   212
Pro  Ser  Lys  Ile  Pro  Val  Arg  Ser  Gln  Lys  Arg  Thr  Pro  Phe  Pro  Thr
     20                       25                       30

GTT  ACA  TCG  TGC  GCC  GTG  GAC  CAG  GAG  AAC  CAA  GAT  CCA  AGG  AGA  TGG   260
Val  Thr  Ser  Cys  Ala  Val  Asp  Gln  Glu  Asn  Gln  Asp  Pro  Arg  Arg  Trp
35                       40                       45                       50

GTG  CAG  AAA  CCA  CCG  CTC  AAT  ATT  CAA  CGC  CCC  CTC  GTT  GAT  TCA  GCA   308
Val  Gln  Lys  Pro  Pro  Leu  Asn  Ile  Gln  Arg  Pro  Leu  Val  Asp  Ser  Ala
               55                       60                       65

GGC  CCC  AGG  CCG  AAA  GCC  AGG  CAC  CAG  GCA  GAG  ACA  TCA  CAA  AGA  TTG   356
Gly  Pro  Arg  Pro  Lys  Ala  Arg  His  Gln  Ala  Glu  Thr  Ser  Gln  Arg  Leu
          70                       75                       80

GTG  GGG  ATC  AGT  CAG  CCT  CGG  AAC  CCC  TTG  GAA  GAG  CTC  AGG  CCT  AGC   404
Val  Gly  Ile  Ser  Gln  Pro  Arg  Asn  Pro  Leu  Glu  Glu  Leu  Arg  Pro  Ser
     85                       90                       95

CCT  AGG  GGT  CAA  AAT  GTG  GGG  CCT  GGG  CCC  CCT  GCC  CAG  ACA  GAG  GCT   452
Pro  Arg  Gly  Gln  Asn  Val  Gly  Pro  Gly  Pro  Pro  Ala  Gln  Thr  Glu  Ala
100                     105                     110

CCA  GGG  ACC  ATA  GAG  TTT  GTG  GCT  GAC  CCT  GCA  GCC  CTG  GCC  ACC  ATC   500
Pro  Gly  Thr  Ile  Glu  Phe  Val  Ala  Asp  Pro  Ala  Ala  Leu  Ala  Thr  Ile
115                     120                     125                     130

CTG  TCA  GGT  GAG  GGT  GTG  AAG  AGC  TGT  CAC  CTG  GGG  CGC  CAG  CCT  AGT   548
Leu  Ser  Gly  Glu  Gly  Val  Lys  Ser  Cys  His  Leu  Gly  Arg  Gln  Pro  Ser
               135                     140                     145
```

| | | | | | | | | | | | | | | | | |
|---|---|---|---|---|---|---|---|---|---|---|---|---|---|---|---|---|
| CTG | GCT | AAA | AGA | GTA | CTG | GTT | CGA | GGA | AGT | CAG | GGA | GGC | ACC | ACC | CAG | 596 |
| Leu | Ala | Lys | Arg | Val | Leu | Val | Arg | Gly | Ser | Gln | Gly | Gly | Thr | Thr | Gln | |
| | | 150 | | | | | 155 | | | | | 160 | | | | |
| AGG | GTC | CAG | GGT | GTT | CGG | GCC | TCT | GCA | TAT | TTG | GCC | CCC | AGA | ACC | CCC | 644 |
| Arg | Val | Gln | Gly | Val | Arg | Ala | Ser | Ala | Tyr | Leu | Ala | Pro | Arg | Thr | Pro | |
| | | 165 | | | | | 170 | | | | | 175 | | | | |
| ACC | CAC | CGA | CTG | GAC | CCT | GCC | AGG | GCT | TCC | TGC | TTC | TCT | AGG | CTG | GAG | 692 |
| Thr | His | Arg | Leu | Asp | Pro | Ala | Arg | Ala | Ser | Cys | Phe | Ser | Arg | Leu | Glu | |
| | 180 | | | | | 185 | | | | | 190 | | | | | |
| GGA | CCA | GGA | CCT | CGA | GGC | CGG | ACA | TTG | TGC | CCC | CAG | AGG | CTA | CAG | GCT | 740 |
| Gly | Pro | Gly | Pro | Arg | Gly | Arg | Thr | Leu | Cys | Pro | Gln | Arg | Leu | Gln | Ala | |
| 195 | | | | | 200 | | | | | 205 | | | | | 210 | |
| CTG | ATT | TCA | CCT | TCA | GGA | CCT | TCC | TTT | CAC | CCT | TCC | ACT | CAC | CCC | AGT | 788 |
| Leu | Ile | Ser | Pro | Ser | Gly | Pro | Ser | Phe | His | Pro | Ser | Thr | His | Pro | Ser | |
| | | | | 215 | | | | | 220 | | | | | 225 | | |
| TTC | CAG | GAG | CTA | AGA | AGG | GAG | ACA | GCT | GGC | AGC | AGC | CGG | ACT | TCA | GTG | 836 |
| Phe | Gln | Glu | Leu | Arg | Arg | Glu | Thr | Ala | Gly | Ser | Ser | Arg | Thr | Ser | Val | |
| | | | | 230 | | | | | 235 | | | | | 240 | | |
| AGC | CAG | GCC | TCA | GGA | TTG | CTC | CTG | GAG | ACC | CCA | GTC | CAG | CCT | GCT | TTC | 884 |
| Ser | Gln | Ala | Ser | Gly | Leu | Leu | Leu | Glu | Thr | Pro | Val | Gln | Pro | Ala | Phe | |
| | | | 245 | | | | | 250 | | | | | 255 | | | |
| TCT | CTT | CCT | AAA | GGA | GAA | CGC | GAG | GTT | GTC | ACT | CAC | TCA | GAT | GAA | GGA | 932 |
| Ser | Leu | Pro | Lys | Gly | Glu | Arg | Glu | Val | Val | Thr | His | Ser | Asp | Glu | Gly | |
| | 260 | | | | | 265 | | | | | 270 | | | | | |
| GGT | GTG | GCC | TCT | CTT | GGT | CTG | GCC | CAG | CGA | GTA | CCA | TTA | AGA | GAA | AAC | 980 |
| Gly | Val | Ala | Ser | Leu | Gly | Leu | Ala | Gln | Arg | Val | Pro | Leu | Arg | Glu | Asn | |
| 275 | | | | | 280 | | | | | 285 | | | | | 290 | |
| CGA | GAA | ATG | TCA | CAT | ACC | AGG | GAC | AGC | CAT | GAC | TCC | CAC | CTG | ATG | CCC | 1028 |
| Arg | Glu | Met | Ser | His | Thr | Arg | Asp | Ser | His | Asp | Ser | His | Leu | Met | Pro | |
| | | | | 295 | | | | | 300 | | | | | 305 | | |
| TCC | CCT | GCC | CCT | GTG | GCC | CAG | CCC | TTG | CCT | GGC | CAT | GTG | GTG | CCA | TGT | 1076 |
| Ser | Pro | Ala | Pro | Val | Ala | Gln | Pro | Leu | Pro | Gly | His | Val | Val | Pro | Cys | |
| | | | 310 | | | | | 315 | | | | | 320 | | | |
| CCA | TCA | CCC | TTT | GGA | CGG | GCT | CAG | CGT | GTA | CCC | TCC | CCA | GGC | CCT | CCA | 1124 |
| Pro | Ser | Pro | Phe | Gly | Arg | Ala | Gln | Arg | Val | Pro | Ser | Pro | Gly | Pro | Pro | |
| | | 325 | | | | | 330 | | | | | 335 | | | | |
| ACT | CTG | ACC | TCA | TAT | TCA | GTG | TTG | CGG | CGT | CTC | ACC | GTT | CAA | CCT | AAA | 1172 |
| Thr | Leu | Thr | Ser | Tyr | Ser | Val | Leu | Arg | Arg | Leu | Thr | Val | Gln | Pro | Lys | |
| | | 340 | | | | | 345 | | | | | 350 | | | | |
| ACC | CGG | TTC | ACA | CCC | ATG | CCA | TCA | ACC | CCC | AGA | GTT | CAG | CAG | GCC | CAG | 1220 |
| Thr | Arg | Phe | Thr | Pro | Met | Pro | Ser | Thr | Pro | Arg | Val | Gln | Gln | Ala | Gln | |
| 355 | | | | | 360 | | | | | 365 | | | | | 370 | |
| TGG | CTG | CGT | GGT | GTC | TCC | CCT | CAG | TCC | TGC | TCT | GAA | GAT | CCT | GCC | CTG | 1268 |
| Trp | Leu | Arg | Gly | Val | Ser | Pro | Gln | Ser | Cys | Ser | Glu | Asp | Pro | Ala | Leu | |
| | | | | 375 | | | | | 380 | | | | | 385 | | |
| CCC | TGG | GAG | CAG | GTT | GCC | GTC | CGG | TTG | TTT | GAC | CAG | GAG | AGT | TGT | ATA | 1316 |
| Pro | Trp | Glu | Gln | Val | Ala | Val | Arg | Leu | Phe | Asp | Gln | Glu | Ser | Cys | Ile | |
| | | | | 390 | | | | | 395 | | | | | 400 | | |
| AGG | TCA | CTG | GAG | GGT | TCT | GGG | AAA | CCA | CCG | GTG | GCC | ACT | CCT | TCT | GGA | 1364 |
| Arg | Ser | Leu | Glu | Gly | Ser | Gly | Lys | Pro | Pro | Val | Ala | Thr | Pro | Ser | Gly | |
| | | | 405 | | | | | 410 | | | | | 415 | | | |
| CCC | CAC | TCT | AAC | AGA | ACC | CCC | AGC | CTC | CAG | GAG | GTG | AAG | ATT | CAA | CGC | 1412 |
| Pro | His | Ser | Asn | Arg | Thr | Pro | Ser | Leu | Gln | Glu | Val | Lys | Ile | Gln | Arg | |
| | 420 | | | | | 425 | | | | | 430 | | | | | |
| ATC | GGT | ATC | CTG | CAA | CAG | CTG | TTG | AGA | CAG | GAA | GTA | GAG | GGG | CTG | GTA | 1460 |
| Ile | Gly | Ile | Leu | Gln | Gln | Leu | Leu | Arg | Gln | Glu | Val | Glu | Gly | Leu | Val | |
| 435 | | | | | 440 | | | | | 445 | | | | | 450 | |
| GGG | GGC | CAG | TGT | GTC | CCT | CTT | AAT | GGA | GGC | TCT | TCT | CTG | GAT | ATG | GTT | 1508 |
| Gly | Gly | Gln | Cys | Val | Pro | Leu | Asn | Gly | Gly | Ser | Ser | Leu | Asp | Met | Val | |
| | | | | 455 | | | | | 460 | | | | | 465 | | |

| | | | | | | | | | | | | | | | | |
|---|---|---|---|---|---|---|---|---|---|---|---|---|---|---|---|---|
| GAA | CTT | CAG | CCC | CTG | CTG | ACT | GAG | ATT | TCT | AGA | ACT | CTG | AAT | GCC | ACA | 1556 |
| Glu | Leu | Gln | Pro 470 | Leu | Leu | Thr | Glu | Ile 475 | Ser | Arg | Thr | Leu | Asn 480 | Ala | Thr | |
| GAG | CAT | AAC | TCT | GGG | ACT | TCC | CAC | CTT | CCT | GGA | CTG | TTA | AAA | CAC | TCA | 1604 |
| Glu | His | Asn 485 | Ser | Gly | Thr | Ser | His 490 | Leu | Pro | Gly | Leu | Leu 495 | Lys | His | Ser | |
| GGG | CTG | CCA | AAG | CCC | TGT | CTT | CCA | GAG | GAG | TGC | GGG | GAA | CCA | CAG | CCC | 1652 |
| Gly | Leu | Pro 500 | Lys | Pro | Cys | Leu | Pro 505 | Glu | Glu | Cys | Gly | Glu 510 | Pro | Gln | Pro | |
| TGC | CCT | CCG | GCA | GAG | CCT | GGG | CCC | CCA | GAG | GCC | TTC | TGT | AGG | AGT | GAG | 1700 |
| Cys | Pro | Pro 515 | Ala | Glu | Pro | Gly | Pro 520 | Pro | Glu | Ala | Phe | Cys 525 | Arg | Ser | Glu 530 | |
| CCT | GAG | ATA | CCA | GAG | CCC | TCC | CTC | CAG | GAA | CAG | CTT | GAA | GTA | CCA | GAG | 1748 |
| Pro | Glu | Ile | Pro | Glu 535 | Pro | Ser | Leu | Gln | Glu 540 | Gln | Leu | Glu | Val | Pro 545 | Glu | |
| CCC | TAC | CCT | CCA | GCA | GAA | CCC | AGG | CCC | CTA | GAG | TCC | TGC | TGT | AGG | AGT | 1796 |
| Pro | Tyr | Pro | Pro 550 | Ala | Glu | Pro | Arg | Pro 555 | Leu | Glu | Ser | Cys | Cys 560 | Arg | Ser | |
| GAG | CCT | GAG | ATA | CCG | GAG | TCC | TCT | CGC | CAG | GAA | CAG | CTT | GAG | GTA | CCT | 1844 |
| Glu | Pro | Glu 565 | Ile | Pro | Glu | Ser | Ser 570 | Arg | Gln | Glu | Gln | Leu 575 | Glu | Val | Pro | |
| GAG | CCC | TGC | CCT | CCA | GCA | GAA | CCC | AGG | CCC | CTA | GAG | TCC | TAC | TGT | AGG | 1892 |
| Glu | Pro 580 | Cys | Pro | Pro | Ala | Glu 585 | Pro | Arg | Pro | Leu | Glu 590 | Ser | Tyr | Cys | Arg | |
| ATT | GAG | CCT | GAG | ATA | CCG | GAG | TCC | TCT | CGC | CAG | GAA | CAG | CTT | GAG | GTA | 1940 |
| Ile 595 | Glu | Pro | Glu | Ile 600 | Pro | Glu | Ser | Ser | Arg 605 | Gln | Glu | Gln | Leu | Glu 610 | Val | |
| CCT | GAG | CCC | TGC | CCT | CCA | GCA | GAA | CCC | GGG | CCC | CTT | CAG | CCC | AGC | ACC | 1988 |
| Pro | Glu 615 | Pro | Cys | Pro | Pro | Ala 620 | Glu | Pro | Gly | Pro | Leu 625 | Gln | Pro | Ser | Thr | |
| CAG | GGG | CAG | TCT | GGA | CCC | CCA | GGG | CCC | TGC | CCT | AGG | GTA | GAG | CTG | GGG | 2036 |
| Gln | Gly | Gln | Ser 630 | Gly | Pro | Pro | Gly | Pro 635 | Cys | Pro | Arg | Val | Glu 640 | Leu | Gly | |
| GCA | TCA | GAG | CCC | TGC | ACC | CTG | GAA | CAT | AGA | AGT | CTA | GAG | TCC | AGT | CTA | 2084 |
| Ala | Ser | Glu 645 | Pro | Cys | Thr | Leu | Glu 650 | His | Arg | Ser | Leu | Glu 655 | Ser | Ser | Leu | |
| CCA | CCC | TGC | TGC | AGT | CAG | TGG | GCT | CCA | GCA | ACC | ACC | AGC | CTG | ATC | TTC | 2132 |
| Pro | Pro 660 | Cys | Cys | Ser | Gln | Trp 665 | Ala | Pro | Ala | Thr | Thr 670 | Ser | Leu | Ile | Phe | |
| TCT | TCC | CAA | CAC | CCG | CTT | TGT | GCC | AGC | CCC | CCT | ATC | TGC | TCA | CTC | CAG | 2180 |
| Ser 675 | Ser | Gln | His | Pro 680 | Leu | Cys | Ala | Ser | Pro 685 | Pro | Ile | Cys | Ser | Leu 690 | Gln | |
| TCT | TTG | AGA | CCC | CCA | GCA | GGC | CAG | GCA | GGC | CTC | AGC | AAT | CTG | GCC | CCT | 2228 |
| Ser | Leu | Arg | Pro | Pro 695 | Ala | Gly | Gln | Ala | Gly 700 | Leu | Ser | Asn | Leu | Ala 705 | Pro | |
| CGA | ACC | CTA | GCC | CTG | AGG | GAG | AGC | CTC | AAA | TCG | TGT | TTA | ACC | GCC | ATC | 2276 |
| Arg | Thr | Leu | Ala 710 | Leu | Arg | Glu | Ser | Leu 715 | Lys | Ser | Cys | Leu | Thr 720 | Ala | Ile | |
| CAC | TGC | TTC | CAC | GAG | GCT | CGT | CTG | GAC | GAT | GAG | TGT | GCC | TTT | TAC | ACC | 2324 |
| His | Cys | Phe 725 | His | Glu | Ala | Arg | Leu 730 | Asp | Asp | Glu | Cys | Ala 735 | Phe | Tyr | Thr | |
| AGC | CGA | GCC | TCT | CCC | TCA | GGC | CCC | ACC | CGG | GTC | TGC | ACC | AAC | CCT | GTG | 2372 |
| Ser | Arg 740 | Ala | Ser | Pro | Ser | Gly 745 | Pro | Thr | Arg | Val | Cys 750 | Thr | Asn | Pro | Val | |
| GCT | ACA | TTA | CTC | GAA | TGG | CAG | GAT | GCC | CTG | TGT | TTC | ATT | CCA | GTT | GGT | 2420 |
| Ala | Thr | Leu 755 | Leu | Glu | Trp | Gln | Asp 760 | Ala | Leu | Cys | Phe | Ile 765 | Pro | Val | Gly 770 | |
| TCT | GCT | GCC | CCC | CAG | GGC | TCT | CCA | T | GATGAGACAA | CCACTCCTGC | | | | | | 2465 |
| Ser | Ala | Ala | Pro | Gln 775 | Gly | Ser | Pro | | | | | | | | | |

```
CCTGCCGTAC TTCTTCCTTT TAGCCCTTAT TTATTGTCGG TCTGCCCATG GGACTGGGAG    2525

CCGCCCACTT TTGTCCTCAA TAAAGTTTCT AAAGTAAAAA AAAAAAAAA AA             2577
```

(2) INFORMATION FOR SEQ ID NO:5:

(i) SEQUENCE CHARACTERISTICS:
        (A) LENGTH: 778 amino acids
        (B) TYPE: amino acid
        (D) TOPOLOGY: linear (ii) MOLECULE TYPE: protein (xi) SEQUENCE DESCRIPTION: SEQ ID NO:5:

```
Met  Thr  Thr  Arg  Gln  Ala  Thr  Lys  Asp  Pro  Leu  Leu  Arg  Gly  Val  Ser
  1             5                  10                 15
Pro  Thr  Pro  Ser  Lys  Ile  Pro  Val  Arg  Ser  Gln  Lys  Arg  Thr  Pro  Phe
           20                  25                 30
Pro  Thr  Val  Thr  Ser  Cys  Ala  Val  Asp  Gln  Glu  Asn  Gln  Asp  Pro  Arg
           35                  40                 45
Arg  Trp  Val  Gln  Lys  Pro  Pro  Leu  Asn  Ile  Gln  Arg  Pro  Leu  Val  Asp
      50                  55                 60
Ser  Ala  Gly  Pro  Arg  Pro  Lys  Ala  Arg  His  Gln  Ala  Glu  Thr  Ser  Gln
 65                  70                  75                 80
Arg  Leu  Val  Gly  Ile  Ser  Gln  Pro  Arg  Asn  Pro  Leu  Glu  Glu  Leu  Arg
                85                  90                 95
Pro  Ser  Pro  Arg  Gly  Gln  Asn  Val  Gly  Pro  Gly  Pro  Pro  Ala  Gln  Thr
               100                 105                110
Glu  Ala  Pro  Gly  Thr  Ile  Glu  Phe  Val  Ala  Asp  Pro  Ala  Ala  Leu  Ala
               115                 120                125
Thr  Ile  Leu  Ser  Gly  Glu  Gly  Val  Lys  Ser  Cys  His  Leu  Gly  Arg  Gln
 130                 135                 140
Pro  Ser  Leu  Ala  Lys  Arg  Val  Leu  Val  Arg  Gly  Ser  Gln  Gly  Gly  Thr
 145                 150                 155                160
Thr  Gln  Arg  Val  Gln  Gly  Val  Arg  Ala  Ser  Ala  Tyr  Leu  Ala  Pro  Arg
                165                 170                175
Thr  Pro  Thr  His  Arg  Leu  Asp  Pro  Ala  Arg  Ala  Ser  Cys  Phe  Ser  Arg
               180                 185                190
Leu  Glu  Gly  Pro  Gly  Pro  Arg  Gly  Arg  Thr  Leu  Cys  Pro  Gln  Arg  Leu
               195                 200                205
Gln  Ala  Leu  Ile  Ser  Pro  Ser  Gly  Pro  Ser  Phe  His  Pro  Ser  Thr  His
 210                 215                 220
Pro  Ser  Phe  Gln  Glu  Leu  Arg  Arg  Glu  Thr  Ala  Gly  Ser  Ser  Arg  Thr
 225                 230                 235                240
Ser  Val  Ser  Gln  Ala  Ser  Gly  Leu  Leu  Leu  Glu  Thr  Pro  Val  Gln  Pro
                245                 250                255
Ala  Phe  Ser  Leu  Pro  Lys  Gly  Glu  Arg  Glu  Val  Val  Thr  His  Ser  Asp
               260                 265                270
Glu  Gly  Gly  Val  Ala  Ser  Leu  Gly  Leu  Ala  Gln  Arg  Val  Pro  Leu  Arg
               275                 280                285
Glu  Asn  Arg  Glu  Met  Ser  His  Thr  Arg  Asp  Ser  His  Asp  Ser  His  Leu
 290                 295                 300
Met  Pro  Ser  Pro  Ala  Pro  Val  Ala  Gln  Pro  Leu  Pro  Gly  His  Val  Val
 305                 310                 315                320
Pro  Cys  Pro  Ser  Pro  Phe  Gly  Arg  Ala  Gln  Arg  Val  Pro  Ser  Pro  Gly
                325                 330                335
```

```
Pro  Pro  Thr  Leu  Thr  Ser  Tyr  Ser  Val  Leu  Arg  Arg  Leu  Thr  Val  Gln
               340                 345                           350

Pro  Lys  Thr  Arg  Phe  Thr  Pro  Met  Pro  Ser  Thr  Pro  Arg  Val  Gln  Gln
          355                      360                 365

Ala  Gln  Trp  Leu  Arg  Gly  Val  Ser  Pro  Gln  Ser  Cys  Ser  Glu  Asp  Pro
     370                      375                     380

Ala  Leu  Pro  Trp  Glu  Gln  Val  Ala  Val  Arg  Leu  Phe  Asp  Gln  Glu  Ser
385                      390                      395                           400

Cys  Ile  Arg  Ser  Leu  Glu  Gly  Ser  Gly  Lys  Pro  Pro  Val  Ala  Thr  Pro
               405                      410                           415

Ser  Gly  Pro  His  Ser  Asn  Arg  Thr  Pro  Ser  Leu  Gln  Glu  Val  Lys  Ile
               420                 425                           430

Gln  Arg  Ile  Gly  Ile  Leu  Gln  Gln  Leu  Leu  Arg  Gln  Glu  Val  Glu  Gly
          435                 440                           445

Leu  Val  Gly  Gly  Gln  Cys  Val  Pro  Leu  Asn  Gly  Gly  Ser  Ser  Leu  Asp
     450                      455                 460

Met  Val  Glu  Leu  Gln  Pro  Leu  Leu  Thr  Glu  Ile  Ser  Arg  Thr  Leu  Asn
465                      470                      475                           480

Ala  Thr  Glu  His  Asn  Ser  Gly  Thr  Ser  His  Leu  Pro  Gly  Leu  Leu  Lys
                    485                      490                           495

His  Ser  Gly  Leu  Pro  Lys  Pro  Cys  Leu  Pro  Glu  Glu  Cys  Gly  Glu  Pro
               500                 505                      510

Gln  Pro  Cys  Pro  Pro  Ala  Glu  Pro  Gly  Pro  Pro  Glu  Ala  Phe  Cys  Arg
          515                 520                      525

Ser  Glu  Pro  Glu  Ile  Pro  Glu  Pro  Ser  Leu  Gln  Glu  Gln  Leu  Glu  Val
     530                 535                      540

Pro  Glu  Pro  Tyr  Pro  Pro  Ala  Glu  Pro  Arg  Pro  Leu  Glu  Ser  Cys  Cys
545                 550                      555                           560

Arg  Ser  Glu  Pro  Glu  Ile  Pro  Glu  Ser  Ser  Arg  Gln  Glu  Gln  Leu  Glu
                    565                      570                      575

Val  Pro  Glu  Pro  Cys  Pro  Pro  Ala  Glu  Pro  Arg  Pro  Leu  Glu  Ser  Tyr
               580                      585                      590

Cys  Arg  Ile  Glu  Pro  Glu  Ile  Pro  Glu  Ser  Ser  Arg  Gln  Glu  Gln  Leu
          595                 600                      605

Glu  Val  Pro  Glu  Pro  Cys  Pro  Pro  Ala  Glu  Pro  Gly  Pro  Leu  Gln  Pro
     610                 615                      620

Ser  Thr  Gln  Gly  Gln  Ser  Gly  Pro  Pro  Gly  Pro  Cys  Pro  Arg  Val  Glu
625                      630                      635                           640

Leu  Gly  Ala  Ser  Glu  Pro  Cys  Thr  Leu  Glu  His  Arg  Ser  Leu  Glu  Ser
               645                      650                           655

Ser  Leu  Pro  Pro  Cys  Cys  Ser  Gln  Trp  Ala  Pro  Ala  Thr  Thr  Ser  Leu
               660                      665                           670

Ile  Phe  Ser  Ser  Gln  His  Pro  Leu  Cys  Ala  Ser  Pro  Pro  Ile  Cys  Ser
          675                      680                      685

Leu  Gln  Ser  Leu  Arg  Pro  Pro  Ala  Gly  Gln  Ala  Gly  Leu  Ser  Asn  Leu
     690                      695                      700

Ala  Pro  Arg  Thr  Leu  Ala  Leu  Arg  Glu  Ser  Leu  Lys  Ser  Cys  Leu  Thr
705                      710                      715                           720

Ala  Ile  His  Cys  Phe  His  Glu  Ala  Arg  Leu  Asp  Asp  Glu  Cys  Ala  Phe
                    725                      730                           735

Tyr  Thr  Ser  Arg  Ala  Ser  Pro  Ser  Gly  Pro  Thr  Arg  Val  Cys  Thr  Asn
               740                      745                           750

Pro  Val  Ala  Thr  Leu  Leu  Glu  Trp  Gln  Asp  Ala  Leu  Cys  Phe  Ile  Pro
               755                 760                      765
```

```
Val Gly Ser Ala Ala Pro Gln Gly Ser Pro
    770                 775
```

( 2 ) INFORMATION FOR SEQ ID NO:6:

( i ) SEQUENCE CHARACTERISTICS:
        ( A ) LENGTH: 1293 base pairs
        ( B ) TYPE: nucleic acid
        ( C ) STRANDEDNESS: single
        ( D ) TOPOLOGY: linear ( i x ) FEATURE:
        ( A ) NAME/KEY: CDS
        ( B ) LOCATION: 70..988

( x i ) SEQUENCE DESCRIPTION: SEQ ID NO:6:

```
AATTCGCGTG CCATAGAGAT GTTCATGAAC AAGAACCCTC CTGCCAGGCG CACCCTGGCT            60

GACATCATC ATG GAG AAG CTG ACT GAG AAG CAG ACA GAG GTT GAG ACA              108
          Met Glu Lys Leu Thr Glu Lys Gln Thr Glu Val Glu Thr
            1               5                  10

GTC ATG TCA GAG GTG TCG GGC TTC CCT ATG CCC CAG CTG GAC CCC CGG            156
Val Met Ser Glu Val Ser Gly Phe Pro Met Pro Gln Leu Asp Pro Arg
     15              20                  25

GTC CTA GAA GTG TAC AGG GGG GTC CGG GAG GTA TTA TCT AAG TAC CGC            204
Val Leu Glu Val Tyr Arg Gly Val Arg Glu Val Leu Ser Lys Tyr Arg
 30              35                  40                  45

AGT GGA AAA CTG CCC AAG GCA TTT AAG ATC ATC CCT GCA CTC TCC AAC            252
Ser Gly Lys Leu Pro Lys Ala Phe Lys Ile Ile Pro Ala Leu Ser Asn
             50                  55                  60

TGG GAG CAA ATC CTC TAC GTC ACA GAG CCG GAG GCC TGG ACT GCA GCT            300
Trp Glu Gln Ile Leu Tyr Val Thr Glu Pro Glu Ala Trp Thr Ala Ala
         65                  70                  75

GCC ATG TAC CAG GCC ACC AGG ATT TTT GCC TCT AAC CTG AAG GAA CGC            348
Ala Met Tyr Gln Ala Thr Arg Ile Phe Ala Ser Asn Leu Lys Glu Arg
     80                  85                  90

ATG GCC CAG CGC TTC TAC AAC CTT GTC CTG CTC CCT CGA GTA CGA GAT            396
Met Ala Gln Arg Phe Tyr Asn Leu Val Leu Leu Pro Arg Val Arg Asp
     95                 100                 105

GAC GTT GGT GAA TAC AAA CGA CTC AAC TTC CAT CTC TAC ATG GCT CTC            444
Asp Val Gly Glu Tyr Lys Arg Leu Asn Phe His Leu Tyr Met Ala Leu
110             115                 120                 125

AAG AAG GCC CTT TTC AAA CCT GGA GCC TGG TTC AAA GGG ATC CTG ATT            492
Lys Lys Ala Leu Phe Lys Pro Gly Ala Trp Phe Lys Gly Ile Leu Ile
             130                 135                 140

CCA CTG TGC GAG TCT GGC ACT TGT ACC CTC CGG GAA GCC ATC ATT GTG            540
Pro Leu Cys Glu Ser Gly Thr Cys Thr Leu Arg Glu Ala Ile Ile Val
         145                 150                 155

GGT AGC ATC ATC ACC AAG TGC TCC ATC CCT GTG TTG CAC TCC AGT GCG            588
Gly Ser Ile Ile Thr Lys Cys Ser Ile Pro Val Leu His Ser Ser Ala
         160                 165                 170

GCC ATG CTG AAA ATT GCT GAG ATG GAA TAC AGC GGT GCC AAC AGC ATC            636
Ala Met Leu Lys Ile Ala Glu Met Glu Tyr Ser Gly Ala Asn Ser Ile
     175                 180                 185

TTC CTG CGA CTG CTG CTG GAT AAG AAG TAT GCA CTG CCT TAC CGG GTG            684
Phe Leu Arg Leu Leu Leu Asp Lys Lys Tyr Ala Leu Pro Tyr Arg Val
190             195                 200                 205

CTG GAT GCC CTA GTC TTC CAC TTC CTG GGG TTC CGG ACA GAG AAG CGT            732
Leu Asp Ala Leu Val Phe His Phe Leu Gly Phe Arg Thr Glu Lys Arg
             210                 215                 220

GAA CTG CCT GTG CTG TGG CAC CAG TGC CTC CTG ACT TTG GTC CAG CGC            780
Glu Leu Pro Val Leu Trp His Gln Cys Leu Leu Thr Leu Val Gln Arg
         225                 230                 235
```

```
TAC  AAG  GCC  GAC  TTG  GCC  ACA  GAC  CAG  AAA  GAG  GCC  CTC  TTA  GAA  CTG          828
Tyr  Lys  Ala  Asp  Leu  Ala  Thr  Asp  Gln  Lys  Glu  Ala  Leu  Leu  Glu  Leu
          240                          245                          250

CTC  CGG  CTG  CAG  CCC  CAT  CCA  CAG  CTA  TCG  CCC  GAA  ATC  AGG  CGT  GAG          876
Leu  Arg  Leu  Gln  Pro  His  Pro  Gln  Leu  Ser  Pro  Glu  Ile  Arg  Arg  Glu
     255                          260                          265

CTT  CAG  AGT  GCA  GCC  CCC  GCA  TGT  GGA  AGA  TGT  TCC  CAT  CAC  CGT  GGA          924
Leu  Gln  Ser  Ala  Ala  Pro  Ala  Cys  Gly  Arg  Cys  Ser  His  His  Arg  Gly
270                      275                          280                      285

GTG  AGG  AAA  ACA  GTC  AGC  TTG  TCC  TGG  CCA  AAG  GGG  TTT  GGA  AGG  ACA          972
Val  Arg  Lys  Thr  Val  Ser  Leu  Ser  Trp  Pro  Lys  Gly  Phe  Gly  Arg  Thr
                    290                          295                          300

CCA  AGA  CCC  CGT  TGG  T GACTGAAGAT  GACACTGAGC  TTTAATGGCT  GAAGACCCAG              1028
Pro  Arg  Pro  Arg  Trp
               305

ATCAGGGCAG  TGACCAGATC  ACAGGGACAT  CTGTGGCTCC  CAGTCCAGGA  CAGGAAGGAC                 1088

TGAGGGTCTG  GCTGGTTCCC  TCTTCCATTC  TAGGCCCTTA  TCCCTGTTTA  GTTCTGAGAG                 1148

CCAACTTGAG  ATACCATATG  CTAGCATTCC  CAGTCCCCAG  CTGGGGCTTG  GTGTGAGTAC                 1208

TTTTTCTATG  GCTATTGTGT  CAGGTCACTG  TGGATAAAGG  CAAAGACAGA  TATTTATTGA                 1268

AAAAAAAAAA  AAAAAAAAAA  AAAAA                                                          1293
```

( 2 ) INFORMATION FOR SEQ ID NO:7:

( i ) SEQUENCE CHARACTERISTICS:
        ( A ) LENGTH: 306 amino acids
        ( B ) TYPE: amino acid
        ( D ) TOPOLOGY: linear ( i i ) MOLECULE TYPE: protein ( x i ) SEQUENCE DESCRIPTION: SEQ ID NO:7:

```
Met  Glu  Lys  Leu  Thr  Glu  Lys  Gln  Thr  Glu  Val  Glu  Thr  Val  Met  Ser
1                   5                   10                          15

Glu  Val  Ser  Gly  Phe  Pro  Met  Pro  Gln  Leu  Asp  Pro  Arg  Val  Leu  Glu
               20                       25                          30

Val  Tyr  Arg  Gly  Val  Arg  Glu  Val  Leu  Ser  Lys  Tyr  Arg  Ser  Gly  Lys
          35                       40                       45

Leu  Pro  Lys  Ala  Phe  Lys  Ile  Ile  Pro  Ala  Leu  Ser  Asn  Trp  Glu  Gln
     50                       55                       60

Ile  Leu  Tyr  Val  Thr  Glu  Pro  Glu  Ala  Trp  Thr  Ala  Ala  Ala  Met  Tyr
65                       70                       75                           80

Gln  Ala  Thr  Arg  Ile  Phe  Ala  Ser  Asn  Leu  Lys  Glu  Arg  Met  Ala  Gln
               85                       90                          95

Arg  Phe  Tyr  Asn  Leu  Val  Leu  Leu  Pro  Arg  Val  Arg  Asp  Asp  Val  Gly
               100                      105                         110

Glu  Tyr  Lys  Arg  Leu  Asn  Phe  His  Leu  Tyr  Met  Ala  Leu  Lys  Lys  Ala
          115                      120                      125

Leu  Phe  Lys  Pro  Gly  Ala  Trp  Phe  Lys  Gly  Ile  Leu  Ile  Pro  Leu  Cys
     130                      135                      140

Glu  Ser  Gly  Thr  Cys  Thr  Leu  Arg  Glu  Ala  Ile  Ile  Val  Gly  Ser  Ile
145                      150                      155                          160

Ile  Thr  Lys  Cys  Ser  Ile  Pro  Val  Leu  His  Ser  Ser  Ala  Ala  Met  Leu
               165                      170                         175

Lys  Ile  Ala  Glu  Met  Glu  Tyr  Ser  Gly  Ala  Asn  Ser  Ile  Phe  Leu  Arg
               180                      185                         190

Leu  Leu  Leu  Asp  Lys  Lys  Tyr  Ala  Leu  Pro  Tyr  Arg  Val  Leu  Asp  Ala
```

195                           200                           205
Leu  Val  Phe  His  Phe  Leu  Gly  Phe  Arg  Thr  Glu  Lys  Arg  Glu  Leu  Pro
     210                      215                      220

Val  Leu  Trp  His  Gln  Cys  Leu  Leu  Thr  Leu  Val  Gln  Arg  Tyr  Lys  Ala
225                      230                      235                      240

Asp  Leu  Ala  Thr  Asp  Gln  Lys  Glu  Ala  Leu  Leu  Glu  Leu  Leu  Arg  Leu
               245                      250                      255

Gln  Pro  His  Pro  Gln  Leu  Ser  Pro  Glu  Ile  Arg  Arg  Glu  Leu  Gln  Ser
               260                      265                      270

Ala  Ala  Pro  Ala  Cys  Gly  Arg  Cys  Ser  His  His  Arg  Gly  Val  Arg  Lys
               275                      280                      285

Thr  Val  Ser  Leu  Ser  Trp  Pro  Lys  Gly  Phe  Gly  Arg  Thr  Pro  Arg  Pro
     290                      295                      300

Arg  Trp
305

( 2 ) INFORMATION FOR SEQ ID NO:8:

( i ) SEQUENCE CHARACTERISTICS:
        ( A ) LENGTH: 2223 base pairs
        ( B ) TYPE: nucleic acid
        ( C ) STRANDEDNESS: single
        ( D ) TOPOLOGY: linear ( i x ) FEATURE:
        ( A ) NAME/KEY: CDS
        ( B ) LOCATION: 199..2223

( x i ) SEQUENCE DESCRIPTION: SEQ ID NO:8:

CACCTCTGTC  GTTCCCCAGT  GTTCCACAAG  AAGAAACCTT  ACGTCAGGCC  CCTGCTGGAC        60

TCCCCCGAGA  AACTCTGTTC  CAATCCCGCG  TTCTTCCTCC  CAAAGAAATT  CCTTCTTTGT       120

CTCCACCAT   TCCCCGTCAA  GGCTCCCTGC  CCCAAACTTC  CAGTGCTCCC  AAGCAAGAGA       180

CTTCTGGCTG  GATGCCAC  ATG  TGC  TCC  AGA  AGG  GAC  CCT  CAC  TCC  TGT  GTT  231
                      Met  Cys  Ser  Arg  Arg  Asp  Pro  His  Ser  Cys  Val
                      1                  5                        10

CTG  CCG  CTT  CTG  AGC  AAG  AGA  CTT  CTC  TCC  AGG  GCC  CCC  TGG  CTT  CCC  279
Leu  Pro  Leu  Leu  Ser  Lys  Arg  Leu  Leu  Ser  Arg  Ala  Pro  Trp  Leu  Pro
               15                       20                       25

AGG  AAG  GGA  CCC  AGT  ATC  CAC  CCC  CAG  CTG  GTG  GTG  AAC  AAG  AAG  CCT  327
Arg  Lys  Gly  Pro  Ser  Ile  His  Pro  Gln  Leu  Val  Val  Asn  Lys  Lys  Pro
               30                       35                       40

CCC  TTC  TCT  CCC  ACT  CCC  CCC  ACC  ACC  AGG  AAG  CCC  CCG  CTC  ACT  CCC  375
Pro  Phe  Ser  Pro  Thr  Pro  Pro  Thr  Thr  Arg  Lys  Pro  Pro  Leu  Thr  Pro
          45                       50                       55

CTG  AAG  CTC  CTG  AGA  AAG  ACC  CCT  GAC  CCT  TCC  CCA  ACA  GTT  CCC  GAG  423
Leu  Lys  Leu  Leu  Arg  Lys  Thr  Pro  Asp  Pro  Ser  Pro  Thr  Val  Pro  Glu
60                       65                       70                       75

ACT  GAC  ATG  GAC  CCG  CTG  CTC  CAG  AGC  CCG  GTT  TCC  CAA  AAG  GAC  ACC  471
Thr  Asp  Met  Asp  Pro  Leu  Leu  Gln  Ser  Pro  Val  Ser  Gln  Lys  Asp  Thr
               80                       85                       90

CCT  TTC  CAG  ATC  TCT  TCT  GGA  GTC  CAG  AAG  GAA  CAG  CCG  CTC  CCC  ACG  519
Pro  Phe  Gln  Ile  Ser  Ser  Gly  Val  Gln  Lys  Glu  Gln  Pro  Leu  Pro  Thr
               95                       100                      105

GGA  GAG  ATC  ACC  CGC  TTG  GGT  GTG  TGG  GCT  GCC  GTC  CAA  GCA  GTG  GAG  567
Gly  Glu  Ile  Thr  Arg  Leu  Gly  Val  Trp  Ala  Ala  Val  Gln  Ala  Val  Glu
          110                      115                      120

AGG  AAG  CTG  GAG  GCC  CAG  GCC  ATG  AGG  CTA  CTG  ACC  CTG  GAA  GGC  AGG  615
Arg  Lys  Leu  Glu  Ala  Gln  Ala  Met  Arg  Leu  Leu  Thr  Leu  Glu  Gly  Arg
          125                      130                      135

| | | | | | | | | | | | | | | | | |
|---|---|---|---|---|---|---|---|---|---|---|---|---|---|---|---|---|
| ACG | GGG | ACA | AAT | GAA | AAG | AAG | ATA | GCC | GAC | TGC | GAG | AAG | ACA | GCC | GTG | 663 |
| Thr | Gly | Thr | Asn | Glu | Lys | Lys | Ile | Ala | Asp | Cys | Glu | Lys | Thr | Ala | Val | |
| 140 | | | | 145 | | | | 150 | | | | | | | 155 | |
| GAG | TTC | GCG | AAC | CAT | CTG | GAG | AGC | AAG | TGG | GTC | GTG | TTG | GGG | ACC | CTG | 711 |
| Glu | Phe | Ala | Asn | His | Leu | Glu | Ser | Lys | Trp | Val | Val | Leu | Gly | Thr | Leu | |
| | | | | 160 | | | | 165 | | | | | | 170 | | |
| CTG | CAG | GAG | TAT | GGG | CTG | CAG | CAG | AGG | CGG | CTG | GAG | AAC | ATG | GAG | AAC | 759 |
| Leu | Gln | Glu | Tyr | Gly | Leu | Gln | Gln | Arg | Arg | Leu | Glu | Asn | Met | Glu | Asn | |
| | | | 175 | | | | 180 | | | | | 185 | | | | |
| CTG | CTG | AAA | AAC | AGA | AAT | TTC | TGG | ATC | CTG | CGG | CTG | CCC | CCC | GGC | AGC | 807 |
| Leu | Leu | Lys | Asn | Arg | Asn | Phe | Trp | Ile | Leu | Arg | Leu | Pro | Pro | Gly | Ser | |
| | | 190 | | | | | 195 | | | | 200 | | | | | |
| AAT | GGA | GAA | GTT | CCC | AAG | GTC | CCT | GTC | ACA | TTT | GAT | GAT | GTT | GCT | GTG | 855 |
| Asn | Gly | Glu | Val | Pro | Lys | Val | Pro | Val | Thr | Phe | Asp | Asp | Val | Ala | Val | |
| | 205 | | | | | 210 | | | | | 215 | | | | | |
| CAC | TTC | TCG | GAG | CAG | GAG | TGG | GGA | AAC | CTG | TCT | GAG | TGG | CAG | AAG | GAG | 903 |
| His | Phe | Ser | Glu | Gln | Glu | Trp | Gly | Asn | Leu | Ser | Glu | Trp | Gln | Lys | Glu | |
| 220 | | | | 225 | | | | | 230 | | | | | | 235 | |
| CTC | TAC | AAG | AAC | GTG | ATG | AGG | GGC | AAC | TAC | GAG | TCC | CTG | GTT | TCC | ATG | 951 |
| Leu | Tyr | Lys | Asn | Val | Met | Arg | Gly | Asn | Tyr | Glu | Ser | Leu | Val | Ser | Met | |
| | | | | 240 | | | | 245 | | | | | | 250 | | |
| GAC | TAT | GCA | ATT | TCC | AAA | CCA | GAC | CTC | ATG | TCA | CAG | ATG | GAG | CGC | GGG | 999 |
| Asp | Tyr | Ala | Ile | Ser | Lys | Pro | Asp | Leu | Met | Ser | Gln | Met | Glu | Arg | Gly | |
| | | | 255 | | | | 260 | | | | | 265 | | | | |
| GAG | CGG | CCC | ACC | ATG | CAG | GAG | CAG | GAA | GAC | TCT | GAG | GAG | GGC | GAA | ACG | 1047 |
| Glu | Arg | Pro | Thr | Met | Gln | Glu | Gln | Glu | Asp | Ser | Glu | Glu | Gly | Glu | Thr | |
| | | 270 | | | | 275 | | | | | 280 | | | | | |
| CCG | ACA | GAT | CCC | AGT | GCT | GCG | CAC | GAT | GGG | ATC | GTG | ATT | AAG | ATC | GAG | 1095 |
| Pro | Thr | Asp | Pro | Ser | Ala | Ala | His | Asp | Gly | Ile | Val | Ile | Lys | Ile | Glu | |
| | 285 | | | | 290 | | | | 295 | | | | | | | |
| GTA | CAG | ACC | AAC | GAC | GAG | GGC | TCA | GAA | AGT | TTG | GAG | ACA | CCT | GAG | CCC | 1143 |
| Val | Gln | Thr | Asn | Asp | Glu | Gly | Ser | Glu | Ser | Leu | Glu | Thr | Pro | Glu | Pro | |
| 300 | | | | | 305 | | | | | 310 | | | | | 315 | |
| CTG | ATG | GGA | CAG | GTG | GAA | GAG | CAC | GGC | TTC | CAG | GAC | TCA | GAG | CTG | GGT | 1191 |
| Leu | Met | Gly | Gln | Val | Glu | Glu | His | Gly | Phe | Gln | Asp | Ser | Glu | Leu | Gly | |
| | | | | 320 | | | | 325 | | | | | | 330 | | |
| GAN | CCC | TGT | GGG | GAA | CAG | CCA | GAC | CTG | GAC | ATG | CAG | GAG | CCA | GAG | AAC | 1239 |
| Xaa | Pro | Cys | Gly | Glu | Gln | Pro | Asp | Leu | Asp | Met | Gln | Glu | Pro | Glu | Asn | |
| | | | 335 | | | | 340 | | | | | 345 | | | | |
| ACG | CTG | GAG | GAG | TCC | ACG | GAA | GGC | TCC | AGC | GAG | TTC | AGC | GAA | CTG | AAG | 1287 |
| Thr | Leu | Glu | Glu | Ser | Thr | Glu | Gly | Ser | Ser | Glu | Phe | Ser | Glu | Leu | Lys | |
| | | 350 | | | | 355 | | | | | 360 | | | | | |
| CAG | ATG | CTG | GTG | CAG | CAG | AGG | AAC | TGC | ACG | GAG | GGG | ATC | GTG | ATC | AAG | 1335 |
| Gln | Met | Leu | Val | Gln | Gln | Arg | Asn | Cys | Thr | Glu | Gly | Ile | Val | Ile | Lys | |
| | 365 | | | | | 370 | | | | | 375 | | | | | |
| ACA | GAG | GAA | CAA | GAC | GAG | GAG | GAA | GAG | GAG | GAG | GAG | GAT | GAG | CTG | 1383 |
| Thr | Glu | Glu | Gln | Asp | Glu | Glu | Glu | Glu | Glu | Glu | Glu | Asp | Glu | Leu | |
| 380 | | | | | 385 | | | | | 390 | | | | | 395 | |
| CCG | CAG | CAC | TTG | CAA | TCC | CTT | GGG | CAG | CTG | TCC | GGG | AGA | TAT | GAG | GCC | 1431 |
| Pro | Gln | His | Leu | Gln | Ser | Leu | Gly | Gln | Leu | Ser | Gly | Arg | Tyr | Glu | Ala | |
| | | | | 400 | | | | 405 | | | | | | 410 | | |
| AGT | ATG | TAC | CAG | ACC | CCG | CTG | CCC | GGG | GAG | ATG | TCC | CCC | GAG | GGC | GAG | 1479 |
| Ser | Met | Tyr | Gln | Thr | Pro | Leu | Pro | Gly | Glu | Met | Ser | Pro | Glu | Gly | Glu | |
| | | | 415 | | | | 420 | | | | | 425 | | | | |
| GAG | AGC | CCC | CCG | CCC | CTG | CAG | GTT | GGA | AAC | CCC | GCA | GTG | AAA | AGG | CTG | 1527 |
| Glu | Ser | Pro | Pro | Pro | Leu | Gln | Val | Gly | Asn | Pro | Ala | Val | Lys | Arg | Leu | |
| | | | 430 | | | | 435 | | | | | 440 | | | | |
| GCG | CCC | TCC | GTG | CAC | GGT | GAG | CGG | GAC | CTG | AGC | GAG | AAC | CGC | GGG | GGC | 1575 |
| Ala | Pro | Ser | Val | His | Gly | Glu | Arg | Asp | Leu | Ser | Glu | Asn | Arg | Gly | Gly | |
| | | 445 | | | | 450 | | | | | 455 | | | | | |

| | | | | | | | | | | | | | | | | |
|---|---|---|---|---|---|---|---|---|---|---|---|---|---|---|---|---|
| TCG | AGC | CAG | CAG | AGT | GGG | AAC | CGG | CGC | GGC | GAG | CGG | CCC | TTC | ACA | TGC | 1623 |
| Ser | Ser | Gln | Gln | Ser | Gly | Asn | Arg | Arg | Gly | Glu | Arg | Pro | Phe | Thr | Cys | |
| 460 | | | | | 465 | | | | 470 | | | | | | 475 | |
| ATG | GAG | TGC | GGC | AAG | AGC | TTC | CGC | CTG | AAG | ATC | AAC | CTC | ATC | ATC | CAC | 1671 |
| Met | Glu | Cys | Gly | Lys | Ser | Phe | Arg | Leu | Lys | Ile | Asn | Leu | Ile | Ile | His | |
| | | | | 480 | | | | | 485 | | | | | 490 | | |
| CAC | CAG | CGC | AAC | CAA | CAT | CAA | GGA | GGG | GGC | CCT | ACG | AGT | GCG | CCG | AAT | 1719 |
| His | Gln | Arg | Asn | Gln | His | Gln | Gly | Gly | Gly | Pro | Thr | Ser | Ala | Pro | Asn | |
| | | | 495 | | | | | 500 | | | | | 505 | | | |
| GTG | AGA | TCA | GCT | TTC | CGG | CAC | AAG | CAA | CAG | CTC | ACG | CTG | CAC | CAG | CGC | 1767 |
| Val | Arg | Ser | Ala | Phe | Arg | His | Lys | Gln | Gln | Leu | Thr | Leu | His | Gln | Arg | |
| | | 510 | | | | | 515 | | | | | 520 | | | | |
| ATC | CAC | CGC | GTG | CGC | GGA | GGC | TGC | GTC | TCA | CCC | GAA | CGC | GGG | CCC | ACG | 1815 |
| Ile | His | Arg | Val | Arg | Gly | Gly | Cys | Val | Ser | Pro | Glu | Arg | Gly | Pro | Thr | |
| | 525 | | | | | 530 | | | | | 535 | | | | | |
| TTC | AAC | CCC | AAG | NAC | GCG | CTC | AAG | CCG | CGT | CCC | AAG | TCA | CCC | AGC | TCT | 1863 |
| Phe | Asn | Pro | Lys | Xaa | Ala | Leu | Lys | Pro | Arg | Pro | Lys | Ser | Pro | Ser | Ser | |
| 540 | | | | | 545 | | | | | 550 | | | | | 555 | |
| GGT | AGC | GGC | GGC | GGT | GGC | CCT | AAG | CCC | TAC | AAG | TGC | CCC | GAG | TGC | GAC | 1911 |
| Gly | Ser | Gly | Gly | Gly | Gly | Pro | Lys | Pro | Tyr | Lys | Cys | Pro | Glu | Cys | Asp | |
| | | | | 560 | | | | | 565 | | | | | 570 | | |
| AGC | AGC | TTC | AGC | CAC | AAG | TCC | AGC | CTG | ACT | AAA | CAC | CAG | ATC | ACG | CAC | 1959 |
| Ser | Ser | Phe | Ser | His | Lys | Ser | Ser | Leu | Thr | Lys | His | Gln | Ile | Thr | His | |
| | | | 575 | | | | | 580 | | | | | 585 | | | |
| ACG | GGT | GAG | CGG | CCC | TAC | ACG | TGC | CCC | GAG | TGC | AAG | AAG | AGC | TTC | CGC | 2007 |
| Thr | Gly | Glu | Arg | Pro | Tyr | Thr | Cys | Pro | Glu | Cys | Lys | Lys | Ser | Phe | Arg | |
| | | 590 | | | | | 595 | | | | | 600 | | | | |
| CTG | CAC | ATC | AGC | TTG | GTG | ATC | CAT | CAG | CGC | GTG | CAC | GCG | GGC | AAG | CAT | 2055 |
| Leu | His | Ile | Ser | Leu | Val | Ile | His | Gln | Arg | Val | His | Ala | Gly | Lys | His | |
| | 605 | | | | | 610 | | | | | 615 | | | | | |
| GAG | GTC | TCC | TTC | ATC | TGC | AGC | CTG | TGC | GGC | AAG | AGC | TTC | AGC | CGC | CCC | 2103 |
| Glu | Val | Ser | Phe | Ile | Cys | Ser | Leu | Cys | Gly | Lys | Ser | Phe | Ser | Arg | Pro | |
| 620 | | | | | 625 | | | | | 630 | | | | | 635 | |
| TCG | CAC | CTG | CTG | CGC | CAC | CAG | CGG | ACT | CAC | ACA | GGC | GAG | CGG | CCC | TTC | 2151 |
| Ser | His | Leu | Leu | Arg | His | Gln | Arg | Thr | His | Thr | Gly | Glu | Arg | Pro | Phe | |
| | | | | 640 | | | | | 645 | | | | | 650 | | |
| AAG | TGC | CCC | GAG | TGC | GAG | AAG | AGC | TTC | AGC | GAG | AAG | TCC | AAG | CTC | ACC | 2199 |
| Lys | Cys | Pro | Glu | Cys | Glu | Lys | Ser | Phe | Ser | Glu | Lys | Ser | Lys | Leu | Thr | |
| | | | 655 | | | | | 660 | | | | | 665 | | | |
| AAC | CAC | TGC | CGC | GTG | CAC | TCG | CGC | | | | | | | | | 2223 |
| Asn | His | Cys | Arg | Val | His | Ser | Arg | | | | | | | | | |
| | | 670 | | | | | 675 | | | | | | | | | |

(2) INFORMATION FOR SEQ ID NO:9:

(i) SEQUENCE CHARACTERISTICS:
        (A) LENGTH: 675 amino acids
        (B) TYPE: amino acid
        (D) TOPOLOGY: linear (ii) MOLECULE TYPE: protein (xi) SEQUENCE DESCRIPTION: SEQ ID NO:9:

| | | | | | | | | | | | | | | |
|---|---|---|---|---|---|---|---|---|---|---|---|---|---|---|
| Met | Cys | Ser | Arg | Arg | Asp | Pro | His | Ser | Cys | Val | Leu | Pro | Leu | Ser |
| 1 | | | | 5 | | | | | 10 | | | | | 15 |
| Lys | Arg | Leu | Leu | Ser | Arg | Ala | Pro | Trp | Leu | Pro | Arg | Lys | Gly | Pro | Ser |
| | | | | 20 | | | | 25 | | | | | 30 | | |
| Ile | His | Pro | Gln | Leu | Val | Val | Asn | Lys | Lys | Pro | Pro | Phe | Ser | Pro | Thr |
| | | | 35 | | | | | 40 | | | | | 45 | | |
| Pro | Pro | Thr | Thr | Arg | Lys | Pro | Pro | Leu | Thr | Pro | Leu | Lys | Leu | Leu | Arg |
| | | 50 | | | | | 55 | | | | | 60 | | | |

```
Lys  Thr  Pro  Asp  Pro  Ser  Pro  Thr  Val  Pro  Glu  Thr  Asp  Met  Asp  Pro
 65                 70                  75                  80

Leu  Leu  Gln  Ser  Pro  Val  Ser  Gln  Lys  Asp  Thr  Pro  Phe  Gln  Ile  Ser
                85                  90                       95

Ser  Gly  Val  Gln  Lys  Glu  Gln  Pro  Leu  Pro  Thr  Gly  Glu  Ile  Thr  Arg
               100                 105                      110

Leu  Gly  Val  Trp  Ala  Ala  Val  Gln  Ala  Val  Glu  Arg  Lys  Leu  Glu  Ala
               115                 120                      125

Gln  Ala  Met  Arg  Leu  Leu  Thr  Leu  Glu  Gly  Arg  Thr  Gly  Thr  Asn  Glu
          130                      135                 140

Lys  Lys  Ile  Ala  Asp  Cys  Glu  Lys  Thr  Ala  Val  Glu  Phe  Ala  Asn  His
145                      150                 155                           160

Leu  Glu  Ser  Lys  Trp  Val  Val  Leu  Gly  Thr  Leu  Leu  Gln  Glu  Tyr  Gly
                    165                      170                 175

Leu  Gln  Gln  Arg  Arg  Leu  Glu  Asn  Met  Glu  Asn  Leu  Leu  Lys  Asn  Arg
               180                      185                      190

Asn  Phe  Trp  Ile  Leu  Arg  Leu  Pro  Pro  Gly  Ser  Asn  Gly  Glu  Val  Pro
          195                      200                 205

Lys  Val  Pro  Val  Thr  Phe  Asp  Asp  Val  Ala  Val  His  Phe  Ser  Glu  Gln
     210                 215                      220

Glu  Trp  Gly  Asn  Leu  Ser  Glu  Trp  Gln  Lys  Glu  Leu  Tyr  Lys  Asn  Val
225                      230                 235                           240

Met  Arg  Gly  Asn  Tyr  Glu  Ser  Leu  Val  Ser  Met  Asp  Tyr  Ala  Ile  Ser
               245                 250                      255

Lys  Pro  Asp  Leu  Met  Ser  Gln  Met  Glu  Arg  Gly  Glu  Arg  Pro  Thr  Met
               260                 265                      270

Gln  Glu  Gln  Glu  Asp  Ser  Glu  Gly  Glu  Thr  Pro  Thr  Asp  Pro  Ser
          275                 280                      285

Ala  Ala  His  Asp  Gly  Ile  Val  Ile  Lys  Ile  Glu  Val  Gln  Thr  Asn  Asp
          290                 295                      300

Glu  Gly  Ser  Glu  Ser  Leu  Glu  Thr  Pro  Glu  Pro  Leu  Met  Gly  Gln  Val
305                      310                 315                           320

Glu  Glu  His  Gly  Phe  Gln  Asp  Ser  Glu  Leu  Gly  Xaa  Pro  Cys  Gly  Glu
               325                      330                      335

Gln  Pro  Asp  Leu  Asp  Met  Gln  Glu  Pro  Glu  Asn  Thr  Leu  Glu  Glu  Ser
               340                 345                      350

Thr  Glu  Gly  Ser  Ser  Glu  Phe  Ser  Glu  Leu  Lys  Gln  Met  Leu  Val  Gln
               355                 360                      365

Gln  Arg  Asn  Cys  Thr  Glu  Gly  Ile  Val  Ile  Lys  Thr  Glu  Glu  Gln  Asp
     370                 375                      380

Glu  Glu  Glu  Glu  Glu  Glu  Glu  Glu  Asp  Glu  Leu  Pro  Gln  His  Leu  Gln
385                      390                      395                      400

Ser  Leu  Gly  Gln  Leu  Ser  Gly  Arg  Tyr  Glu  Ala  Ser  Met  Tyr  Gln  Thr
                    405                 410                      415

Pro  Leu  Pro  Gly  Glu  Met  Ser  Pro  Glu  Gly  Glu  Glu  Ser  Pro  Pro  Pro
               420                 425                      430

Leu  Gln  Val  Gly  Asn  Pro  Ala  Val  Lys  Arg  Leu  Ala  Pro  Ser  Val  His
          435                 440                      445

Gly  Glu  Arg  Asp  Leu  Ser  Glu  Asn  Arg  Gly  Gly  Ser  Ser  Gln  Gln  Ser
          450                 455                      460

Gly  Asn  Arg  Arg  Gly  Glu  Arg  Pro  Phe  Thr  Cys  Met  Glu  Cys  Gly  Lys
465                      470                      475                      480

Ser  Phe  Arg  Leu  Lys  Ile  Asn  Leu  Ile  Ile  His  His  Gln  Arg  Asn  Gln
                    485                 490                      495
```

His Gln Gly Gly Gly Pro Thr Ser Ala Pro Asn Val Arg Ser Ala Phe
            500                 505                 510

Arg His Lys Gln Gln Leu Thr Leu His Gln Arg Ile His Arg Val Arg
        515                 520                 525

Gly Gly Cys Val Ser Pro Glu Arg Gly Pro Thr Phe Asn Pro Lys Xaa
    530                 535                 540

Ala Leu Lys Pro Arg Pro Lys Ser Pro Ser Ser Gly Ser Gly Gly Gly
545                 550                 555                 560

Gly Pro Lys Pro Tyr Lys Cys Pro Glu Cys Asp Ser Ser Phe Ser His
                565                 570                 575

Lys Ser Ser Leu Thr Lys His Gln Ile Thr His Thr Gly Glu Arg Pro
            580                 585                 590

Tyr Thr Cys Pro Glu Cys Lys Lys Ser Phe Arg Leu His Ile Ser Leu
        595                 600                 605

Val Ile His Gln Arg Val His Ala Gly Lys His Glu Val Ser Phe Ile
    610                 615                 620

Cys Ser Leu Cys Gly Lys Ser Phe Ser Arg Pro Ser His Leu Leu Arg
625                 630                 635                 640

His Gln Arg Thr His Thr Gly Glu Arg Pro Phe Lys Cys Pro Glu Cys
                645                 650                 655

Glu Lys Ser Phe Ser Glu Lys Ser Lys Leu Thr Asn His Cys Arg Val
            660                 665                 670

His Ser Arg
        675

( 2 ) INFORMATION FOR SEQ ID NO:10:

( i ) SEQUENCE CHARACTERISTICS:
        ( A ) LENGTH: 9 amino acids
        ( B ) TYPE: amino acid
        ( D ) TOPOLOGY: linear ( x i ) SEQUENCE DESCRIPTION: SEQ ID NO:10:

Phe Glu Ile Glu Ala Arg Ala Gln Glu
    1               5

( 2 ) INFORMATION FOR SEQ ID NO:11:

( i ) SEQUENCE CHARACTERISTICS:
        ( A ) LENGTH: 9 amino acids
        ( B ) TYPE: amino acid
        ( D ) TOPOLOGY: linear ( x i ) SEQUENCE DESCRIPTION: SEQ ID NO:11:

Asp Gln Glu Asn Gln Asp Pro Arg Arg
1               5

( 2 ) INFORMATION FOR SEQ ID NO:12:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:12:

GGAATTCATG AGCGATGGCT TTGGCAGTAG                    30

( 2 ) INFORMATION FOR SEQ ID NO:13:

( i ) SEQUENCE CHARACTERISTICS:

( A ) LENGTH: 33 base pairs
( B ) TYPE: nucleic acid
( C ) STRANDEDNESS: single
( D ) TOPOLOGY: linear ( x i ) SEQUENCE DESCRIPTION: SEQ ID NO:13:

CGTCGACTCA GTTTGGTCCA CCGCCGAAGC CAG 33

( 2 ) INFORMATION FOR SEQ ID NO:14:

( i ) SEQUENCE CHARACTERISTICS:
( A ) LENGTH: 32 base pairs
( B ) TYPE: nucleic acid
( C ) STRANDEDNESS: single
( D ) TOPOLOGY: linear ( x i ) SEQUENCE DESCRIPTION: SEQ ID NO:14:

GGAATTCATG GATGGCTCTC CCAGCACTGG TG 32

( 2 ) INFORMATION FOR SEQ ID NO:15:

( i ) SEQUENCE CHARACTERISTICS:
( A ) LENGTH: 31 base pairs
( B ) TYPE: nucleic acid
( C ) STRANDEDNESS: single
( D ) TOPOLOGY: linear ( x i ) SEQUENCE DESCRIPTION: SEQ ID NO:15:

GCAGCTGAGT GCTGGTGCTT AGTGTACCAC C 31

( 2 ) INFORMATION FOR SEQ ID NO:16:

( i ) SEQUENCE CHARACTERISTICS:
( A ) LENGTH: 28 base pairs
( B ) TYPE: nucleic acid
( C ) STRANDEDNESS: single
( D ) TOPOLOGY: linear ( x i ) SEQUENCE DESCRIPTION: SEQ ID NO:16:

GGAATTCATG CCCAGCAACA GCATTGGC 28

( 2 ) INFORMATION FOR SEQ ID NO:17:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO:17:

GCAGCTGAGT ACTGGTGCTG GGTCCATCAC AAAAAC 36

( 2 ) INFORMATION FOR SEQ ID NO:18:

( i ) SEQUENCE CHARACTERISTICS:
( A ) LENGTH: 25 base pairs
( B ) TYPE: nucleic acid
( C ) STRANDEDNESS: single
( D ) TOPOLOGY: linear ( x i ) SEQUENCE DESCRIPTION: SEQ ID NO:18:

GGAATTCATG GATATCGACT GCCTA 25

( 2 ) INFORMATION FOR SEQ ID NO:19:

( i ) SEQUENCE CHARACTERISTICS:
( A ) LENGTH: 29 base pairs
( B ) TYPE: nucleic acid (C) STRANDEDNESS: single
(D) TOPOLOGY: linear (xi) SEQUENCE DESCRIPTION: SEQ ID NO:19:

GCAGCTGAGT CTGGAGCTGG GTGCACCAT    29

(2) INFORMATION FOR SEQ ID NO:20:

(i) SEQUENCE CHARACTERISTICS:
(A) LENGTH: 87 amino acids
(B) TYPE: amino acid
(D) TOPOLOGY: linear (xi) SEQUENCE DESCRIPTION: SEQ ID NO:20:

```
Asp Gly Ser Pro Ser Thr Gly Ala Gly Phe Gly Gly Ala Leu Asn Thr
 1               5                  10                  15
Ser Ala Ser Phe Gly Ser Val Leu Asn Thr Ser Thr Gly Phe Gly Gly
                20                  25                  30
Ala Met Ser Thr Ser Ala Asp Phe Gly Gly Thr Leu Ser Thr Ser Val
            35                  40                  45
Cys Phe Gly Gly Ser Pro Gly Thr Ser Val Ser Phe Gly Ser Ala Leu
        50                  55                  60
Asn Thr Asn Ala Gly Tyr Gly Gly Ala Val Ser Thr Asn Thr Asp Phe
65                  70                  75                  80
Gly Gly Thr Leu Ser Thr Ser
                85
```

(2) INFORMATION FOR SEQ ID NO:21:

(i) SEQUENCE CHARACTERISTICS:
(A) LENGTH: 72 amino acids
(B) TYPE: amino acid
(D) TOPOLOGY: linear (xi) SEQUENCE DESCRIPTION: SEQ ID NO:21:

```
Pro Ser Asn Ser Ile Gly Phe Gly Ala Ala Pro Ser Thr Ser Val Ser
 1               5                  10                  15
Phe Gly Gly Ala His Gly Thr Ser Leu Cys Phe Gly Gly Ala Pro Ser
                20                  25                  30
Thr Ser Leu Cys Phe Gly Ser Ala Ser Asn Thr Asn Leu Cys Phe Gly
            35                  40                  45
Gly Pro Pro Ser Thr Ser Ala Cys Phe Ser Gly Ala Thr Ser Pro Ser
        50                  55                  60
Phe Cys Asp Gly Pro Ser Thr Ser
65                  70
```

(2) INFORMATION FOR SEQ ID NO:22:

(i) SEQUENCE CHARACTERISTICS:
(A) LENGTH: 86 amino acids
(B) TYPE: amino acid
(D) TOPOLOGY: linear (xi) SEQUENCE DESCRIPTION: SEQ ID NO:22:

```
Ser Asp Gly Phe Gly Ser Arg Pro Asn Ala Ser Phe Asp Arg Gly Leu
 1               5                  10                  15
Ser Thr Ile Ile Gly Phe Gly Ser Gly Ser Asn Thr Ser Thr Gly Phe
                20                  25                  30
Thr Gly Glu Pro Ser Thr Ser Thr Gly Phe Ser Ser Gly Pro Ser Ser
            35                  40                  45
Ile Val Gly Phe Ser Gly Gly Pro Ser Thr Gly Val Gly Phe Cys Ser
```

-continued

```
                50                          55                          60
Gly  Pro  Ser  Thr  Ser  Gly  Phe  Ser  Gly  Gly  Pro  Ser  Thr  Gly  Ala  Gly
 65                           70                           75                           80

Phe  Gly  Gly  Gly  Pro  Asn
                     85
```